(12) United States Patent
Pathak et al.

(10) Patent No.: US 11,932,626 B2
(45) Date of Patent: *Mar. 19, 2024

(54) 2-PYRIMIDONE ANALOGS AS POTENT ANTIVIRAL AGENTS AGAINST ALPHAVIRUSES

(71) Applicants: Southern Research Institute, Birmingham, AL (US); Oregon Health and Science University, Portland, OR (US)

(72) Inventors: Ashish Kumar Pathak, Birmingham, AL (US); Corinne E. Augelli-Szafran, Homewood, AL (US); Atefeh Garzan, Hoover, AL (US); Daniel Steblow, Banks, OR (US); Nicole Haese, Beaverton, OR (US)

(73) Assignees: Southern Research Institute, Birmingham, AL (US); Oregon Health and Science University, Portland, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 18/080,692

(22) Filed: Dec. 13, 2022

(65) Prior Publication Data

US 2023/0120566 A1 Apr. 20, 2023

Related U.S. Application Data

(63) Continuation of application No. 17/221,666, filed on Apr. 2, 2021, now Pat. No. 11,566,019.

(60) Provisional application No. 63/004,487, filed on Apr. 2, 2020.

(51) Int. Cl.
| | |
|---|---|
| *C07D 403/04* | (2006.01) |
| *C07D 213/69* | (2006.01) |
| *C07D 213/70* | (2006.01) |
| *C07D 213/74* | (2006.01) |
| *C07D 491/052* | (2006.01) |
| *C07D 498/08* | (2006.01) |

(52) U.S. Cl.
CPC ......... *C07D 403/04* (2013.01); *C07D 213/69* (2013.01); *C07D 213/70* (2013.01); *C07D 213/74* (2013.01); *C07D 491/052* (2013.01); *C07D 498/08* (2013.01)

(58) Field of Classification Search
CPC .. C07D 403/04; C07D 213/69; C07D 213/70; C07D 213/74; C07D 491/052; C07D 498/08; A61K 31/167; A61K 31/505
See application file for complete search history.

(56) References Cited

U.S. PATENT DOCUMENTS

| | | | |
|---|---|---|---|
| 7,968,601 B2 | 6/2011 | Linders et al. | |
| 8,008,488 B2 | 8/2011 | Geneste et al. | |
| 11,566,019 B2* | 1/2023 | Pathak | ............... C07D 239/96 |
| 2018/0000824 A1 | 1/2018 | Hoffmann | |

FOREIGN PATENT DOCUMENTS

| | | |
|---|---|---|
| WO | WO2000/041531 | 7/2000 |
| WO | WO2011/154677 | 12/2011 |

OTHER PUBLICATIONS

Morrison (1987), "Aromaticity," *Organic Chemistry*, 5th Ed., Chapter 13, pp. 477-497.
Alexander (1988) "(Acyloxy)alkyl Carbamates as Novel Bioreversible Prodrugs for Amines: Increased Premeation through Biological Membranes," *J. Med. Chem.* 31, pp. 318-322.
Almarasson (2004) "Crystal Engineering of the Composition of Pharmaceutical Phases. Do Pharmaceutical Co-crystals Represent a New Path to Improved Medicines?" *The Royal Society of Chemistry*, pp. 1889-1896.
Pubchem SID 371521474 Deposit Date May 25, 2018, pp. 1-5.
International Search Report and Written Opinion were dated Aug. 9, 2021 by the International Searching Authority for International Application No. PCT/US2021/25645, filed on Apr. 2, 2021 (Applicant—Southern Research Institute) ( 11 Pages).

* cited by examiner

*Primary Examiner* — Deepak R Rao
(74) *Attorney, Agent, or Firm* — Ballard Spahr LLP

(57) ABSTRACT

The present disclosure is concerned with 2-pyrimidone compounds that are capable of inhibiting a viral infection and methods of treating alphavirus viral infections such as, for example, chikungunya, Eastern equine encephalitis (EEEV), Western equine encephalitis (WEEV), and Venezuelan equine encephalitis using these compounds. This abstract is intended as a scanning tool for purposes of searching in the particular art and is not intended to be limiting of the present invention.

20 Claims, 2 Drawing Sheets

2-PYRIMIDONE ANALOGS AS POTENT ANTIVIRAL AGENTS AGAINST ALPHAVIRUSES

CROSS-REFERENCE TO RELATED APPLICATIONS

This Application is a Continuation of U.S. application Ser. No. 17/221,666, filed Apr. 2, 2021, which claims the benefit of U.S. Application No. 63/004,487, filed on Apr. 2, 2020, the contents of which are hereby incorporated by reference in their entirety.

STATEMENT REGARDING FEDERALLY SPONSORED RESEARCH

This invention was made with government support under grants number 1U19AI09680-01 and 1U19AI142759-01 awarded by the National Institutes of Health and the National Institute of Allergy and Infectious Diseases. The government has certain rights in the invention.

BACKGROUND

Arthropod borne viruses have developed a complex life cycle adapted to alternate between insect and vertebrate hosts. These arthropod-borne viruses belong mainly to the families Togaviridae, Flaviviridae, and Bunyaviridae. Alphavirus is a genus of the family Togaviridae. This genus includes such viral infections as chikungunya virus (CHIKV), Venezuelan Equine Encephalitis virus (VEEV), Western Equine Encephalitis virus (WEEV), and Eastern Equine Encephalitis virus (EEEV).

Originally isolated in Tanzania, sporadic outbreaks of CHIKV have continued to plague Asia and Africa. In 2007, the first outbreak in Europe was documented with over 200 confirmed cases. To date, CHIKV has been identified in over 40 countries including the United States of America. The symptoms of CHIKV include fever, rash, and severe joint pain. While most patients usually recover after days to weeks, some may develop chronic arthritis. Additionally, death related to Chikungunya infection has been reported in older patients or patients with weakened immune systems.

VEEV, which was originally isolated from the brains of dead horses, emerges during epizootic outbreaks to infect horses and humans via bridge vectors such as *Aedes taeniorhynchus*. Epidemics typically occur in northern South America but have extended as far north as Mexico and Texas. During an outbreak in Venezuela and Colombia in 1995, approximately 3000 cases of neurologic disease were reported, resulting in 300 deaths.

WEEV causes asymptomatic or mild infections in humans, with non-specific symptoms such as sudden onset of fever, headache, nausea, vomiting, anorexia, and malaise. In rare cases, WEEV infection may also cause encephalitis or encephalomyelitis. Fifteen to fifty percent of the encephalitis survivors, especially young children, suffer from permanent neurological damage (mental retardation, emotional instability, and spastic paresis). WEEV has a mortality range of three to seven percent.

EEEV is the most severe of the arboviral encephalitides and has a mortality of 50 to 75%. Symptoms of this disease include fever, headache, vomiting, respiratory symptoms, leucocytosis, dizziness, decreasing level of consciousness, tremors, seizures, and focal neurological signs. Death can occur within 3 to 5 days of infection. Those who survive suffer from neurological sequel, including convulsions, paralysis, and mental retardation.

Currently, there are no approved treatments for CHIKV, VEEV, WEEEV, or EEEV. Despite the widespread distribution and severity of the effects of these viral infections, a treatment for alphaviruses has remained elusive. Thus, there remains a need for antiviral agents capable of targeting these viruses and methods of making and using same.

SUMMARY

In accordance with the purpose(s) of the invention, as embodied and broadly described herein, the invention, in one aspect, relates to compositions and methods for use in the prevention and treatment of viral infections such as, for example, chikungunya (CHIKV), Western Equine Encephalitis virus (WEEV), Eastern Equine Encephalitis virus (EEEV) and Venezuelan equine encephalitis (VEEV).

Disclosed are compounds having a structure represented by a formula:

wherein n is 0, 1, or 2; wherein p is or 1; wherein A is O, S or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —$OCy^2$, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when Cy$^1$ is C2-C9 heteroaryl, then either (i) p is 1 and A is O or (ii) n is 1 or 2 and each of R$^{3a}$ and R$^{3b}$ are not hydrogen; provided that when Cy$^1$ is C6 aryl, then p is 1 and either (i) A is O or (ii) each of R$^{2a}$ and R$^{2b}$ is hydrogen and at least one of R$^{3a}$ and R$^{3b}$ is not hydrogen; and provided that when Cy$^1$ is

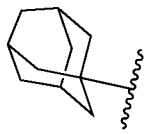 [SMILES: *C12CC3CC(CC(C3)C1)C2]

and p is 0, then n is 0 or 2, or a pharmaceutically acceptable salt thereof.

Also disclosed are compounds having a structure represented by a formula:

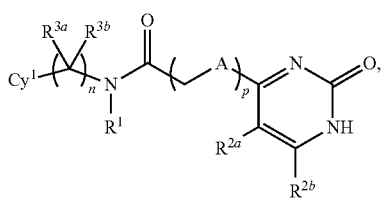

wherein n is 0, 1, or 2; wherein p is 0 or 1; wherein A is O, S, or NH; wherein R$^1$ is selected from hydrogen and C1-C4 alkyl; wherein each of R$^{2a}$ and R$^{2b}$ is independently selected from hydrogen, halogen, C1-C6 alkyl, C1-C4 haloalkyl, C1-C4 alkoxy, —OAr$^1$, —O(C1-C4 alkyl)OR$^{10}$, —O(C1-C4 alkyl)Ar$^1$, —CO$_2$R$^{10}$, and Cy$^2$; wherein each occurrence of R$^{10}$, when present, is independently selected from hydrogen and C1-C4 alkyl; wherein each occurrence of Ar$^1$, when present, is independently selected from C2-C5 heteroaryl and C6-C12 aryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of Cy$^2$, when present, is independently selected from C3-C6 cycloalkyl, C3-C6 heterocycloalkyl, and phenyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ and R$^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of R$^{3a}$ and R$^{3b}$, when present, is independently selected from hydrogen, halogen, C1-C4 alkyl, and C1-C4 haloalkyl; or wherein R$^{3a}$ and R$^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when Cy$^1$ is C2-C9 heteroaryl, then either (i) p is 1 and A is O or (ii) n is 1 or 2 and each of R$^{3a}$ and R$^{3b}$ are not hydrogen; provided that when Cy$^1$ is C6 aryl, then p is 1 and either (i) A is O or (ii) each of R$^{2a}$ and R$^{2b}$ is hydrogen and at least one of R$^{3a}$ and R$^{3b}$ is not hydrogen; and provided that when Cy, is

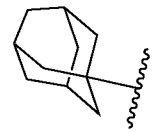 [SMILES: *C12CC3CC(CC(C3)C1)C2]

and p is 0, then n is 0 or 2, or a pharmaceutically acceptable salt thereof.

Also disclosed are compounds having a structure selected from:

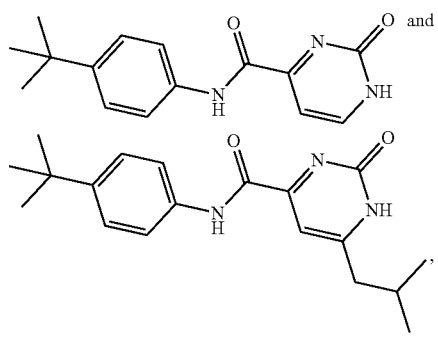

or a pharmaceutically acceptable salt thereof.

Also disclosed are pharmaceutical compositions comprising a therapeutically effective amount of a disclosed compound, and a pharmaceutically acceptable carrier.

Also disclosed are methods for treating a viral infection in a subject, the method comprising administering to the subject an effective amount of a compound having a structure represented by a formula:

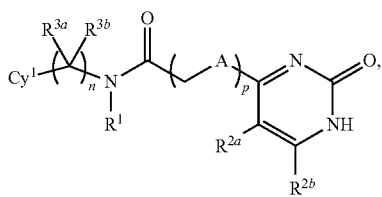

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C4 alkoxy, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of Art, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when p is 1, A is S, and $Cy^1$ is C6 aryl, then $Cy^1$ is not substituted with a halogen group, or a pharmaceutically acceptable salt thereof, wherein the viral infection is due to an Alphavirus, thereby treating the viral infection.

Also disclosed are kits comprising a compound having a structure represented by a formula:

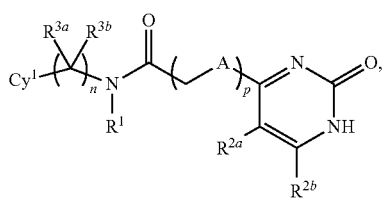

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C4 alkoxy, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when p is 1, A is S, and $Cy^1$ is C6 aryl, then $Cy^1$ is not substituted with a halogen group, or a pharmaceutically acceptable salt thereof, and one or more of: (a) at least one antiviral agent; (b) instructions for administering the compound in connection with treating a viral infection; (c) instructions for administering the compound in connection with reducing the risk of viral infection; or (d) instructions for treating a viral infection.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figures 1A, 1B:
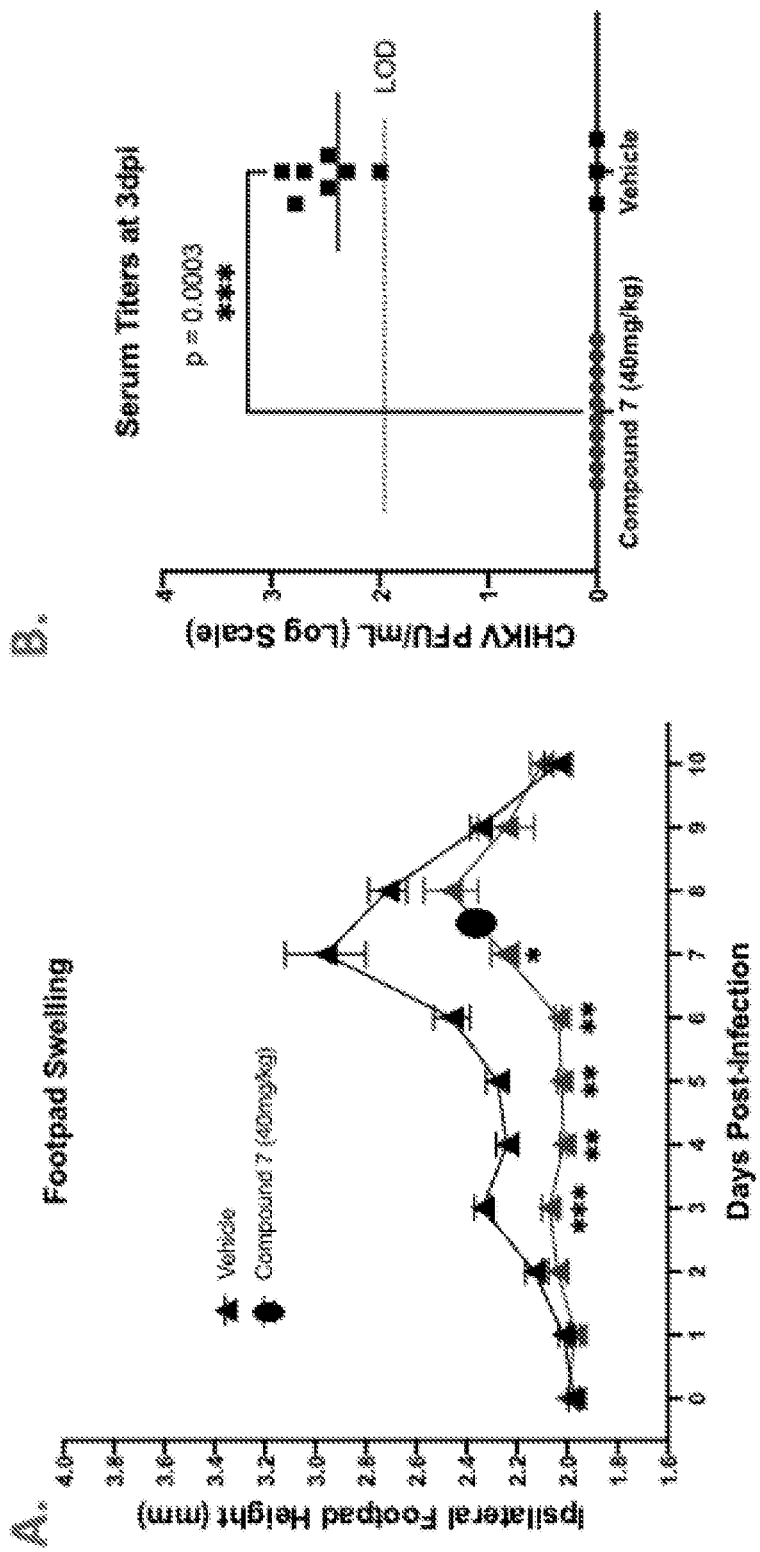
FIG. 1A and FIG. 1B show representative data illustrating that Compound No. 7 reduces CHIKV disease and viremia in mice.
Figure 2:
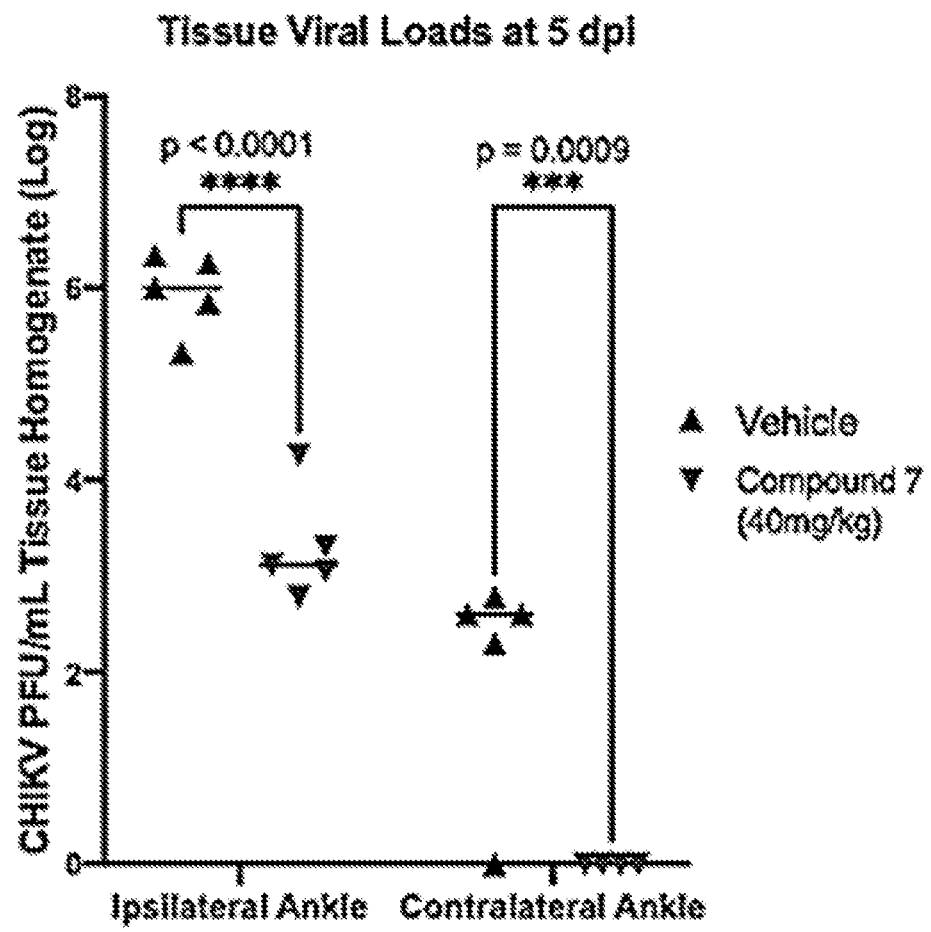
FIG. 2 shows representative data illustrating that Compound No. 7 reduces tissue viral loads in CHIKV-infected mice.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$EC_{50}$," is intended to refer to the effective concentration of a substance (e.g., a compound or a drug) that is required for 50% inhibition of a biological process, or component of a process, including a protein, subunit, organelle, ribonucleoprotein, etc. In one aspect, an $EC_{50}$ can refer to the concentration of a substance that is required for 50% inhibition in vivo, as further defined elsewhere herein.

As used herein, "$EC_{90}$," is intended to refer to the effective concentration of a substance (e.g., a compound or a drug) that is required for 90% inhibition of a biological process, or component of a process, including a protein, subunit, organelle, ribonucleoprotein, etc. In one aspect, an $EC_{50}$ can refer to the concentration of a substance that is required for 90% inhibition in vivo, as further defined elsewhere herein.

As used herein, "$CC_{50}$," is intended to refer to the effective toxicity concentration of a substance (e.g., a compound or a drug) that is required for 50% inhibition of a biological process, or component of a process, including a protein, subunit, organelle, ribonucleoprotein, etc.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), anti-foaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form, which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions that can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a non-aromatic carbon-based ring type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or (A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein, can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein, refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein, refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein, can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group that has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein, refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula CN.

The term "silyl" as used herein is represented by the formula -$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A'S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O$(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —OC(O)$(CH_2)_{0-4}SR$—, SC(S)$SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR˙, or —SSR˙ wherein each R˙ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙—NR˙$_2$, or —NO$_2$, wherein each R˙ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

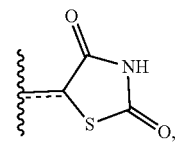

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

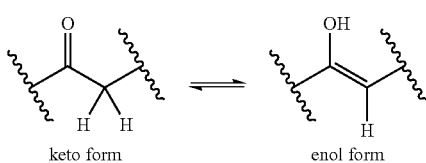

keto form    enol form

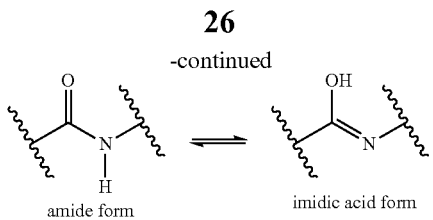

amide form    imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

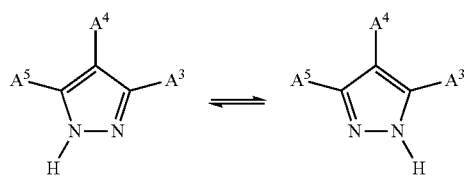

Unless stated to the contrary, the invention includes all such possible tautomers.

It is known that chemical substances form solids that are present in different states of order that are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

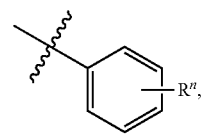

which is understood to be equivalent to a formula:

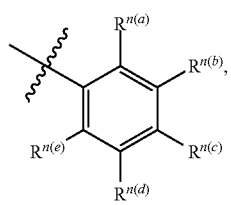

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful in treating disorders associated with a viral infection, in particular, CHIKV, WEEV, EEEV and VEEV. In a further aspect, the viral infection is due to an Alphavirus.

In one aspect, the disclosed compounds exhibit antiviral activity.

In one aspect, the compounds of the invention are useful in inhibiting viral activity in a mammal. In a further aspect, the compounds of the invention are useful in inhibiting viral activity in at least one cell.

In one aspect, the compounds of the invention are useful in the treatment of viral infections, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

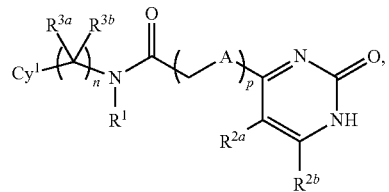

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —OCy², —OAr¹, —O(C1-C4 alkyl)OR¹⁰, —O(C1-C4 alkyl)Ar¹, —CO₂R¹⁰, and Cy²; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of Cy², when present, is independently selected from C3-C6 cycloalkyl, C3-C6 heterocycloalkyl, and phenyl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-

C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when $Cy^1$ is C2-C9 heteroaryl, then either (i) p is 1 and A is O or (ii) n is 1 or 2 and each of $R^{3a}$ and $R^{3b}$ are not hydrogen; provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

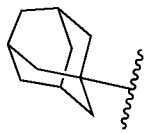

and p is 0, then n is 0 or 2, or a pharmaceutically acceptable salt thereof.

In one aspect, disclosed are compounds having a structure represented by a formula:

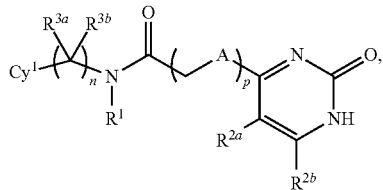

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C4 alkoxy, —OAr$^1$, —O(C1-C4 alkyl)OR$^{10}$, —O(C1-C4 alkyl)Ar$^1$, —CO$_2$R$^{10}$, and Cy$^2$; wherein each occurrence of $R^{10}$, when present, is independently selected from hydrogen and C1-C4 alkyl; wherein each occurrence of Ar$^1$, when present, is independently selected from C2-C5 heteroaryl and C6-C12 aryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of Cy$^2$, when present, is independently selected from C3-C6 cycloalkyl, C3-C6 heterocycloalkyl, and phenyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when $Cy^1$ is C2-C9 heteroaryl, then either (i) p is 1 and A is O or (ii) n is 1 or 2 and each of $R^{3a}$ and $R^{3b}$ are not hydrogen; provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

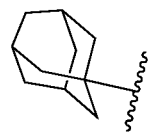 [SMILES: *C12CC3CC(CC(C3)C1)C2]

and p is 0, then n is 0 or 2, or a pharmaceutically acceptable salt thereof.

In one aspect, disclosed are compounds having a structure selected from:

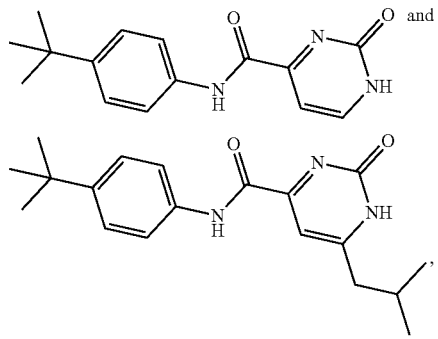

or a pharmaceutically acceptable salt thereof.

In various aspects, the compound has a structure represented by a formula:

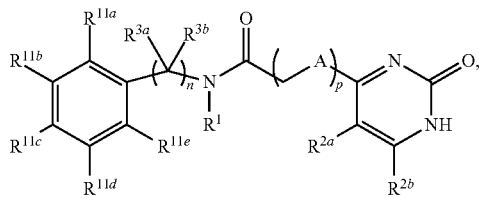

wherein each of $R^{11a}$, $R^{11b}$, $R^{11c}$, $R^{11d}$, and $R^{11e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl, provided that at least two of $R^{11a}$, $R^{11b}$, $R^{11c}$, $R^{11d}$, and $R^{11e}$ are hydrogen.

In various aspects, the compound has a structure represented by a formula:

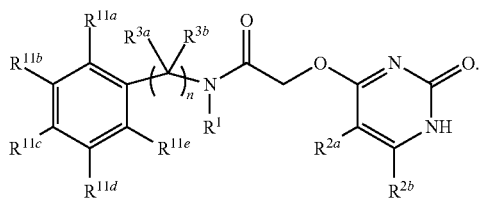

In various aspects, the compound has a structure represented by a formula:

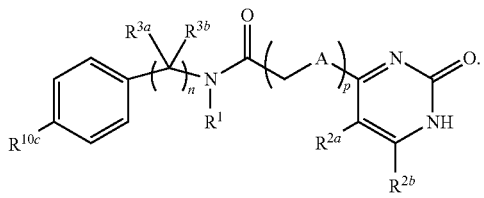

In various aspects, the compound has a structure represented by a formula selected from:

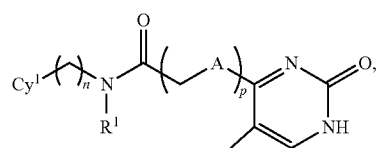

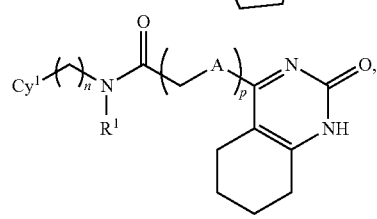

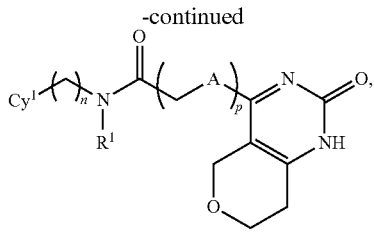

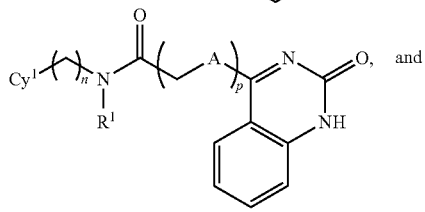

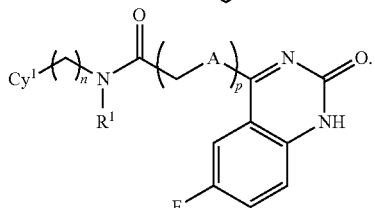

In various aspects, the compound has a structure represented by a formula:

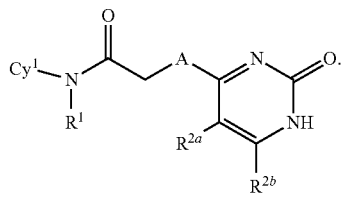

In various aspects, the compound has a structure represented by a formula:

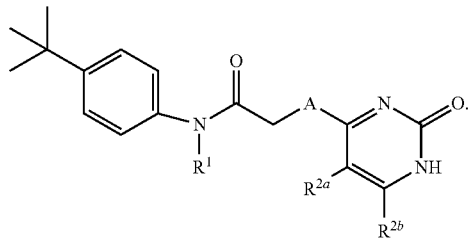

In various aspects, the compound has a structure represented by a formula:

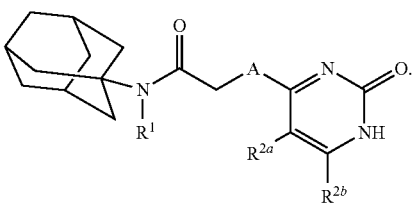

In various aspects, the compound has a structure represented by a formula:

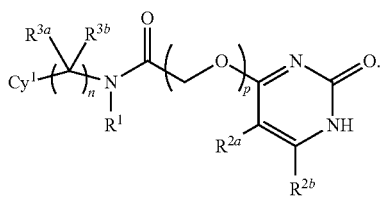

In various aspects, the compound has a structure represented by a formula:

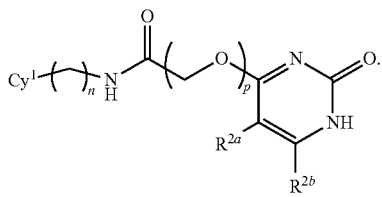

In various aspects, the compound has a structure represented by a formula:

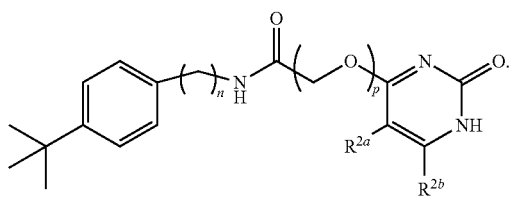

In various aspects, the compound has a structure represented by a formula:

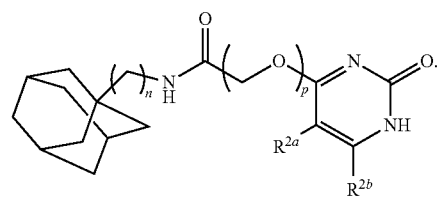

In various aspects, the compound has a structure represented by a formula:

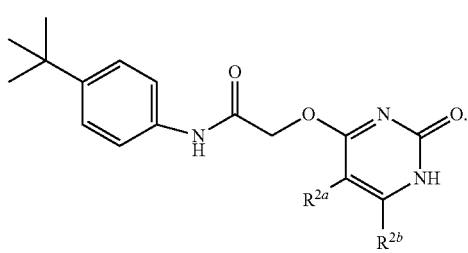

In various aspects, the compound has a structure represented by a formula:

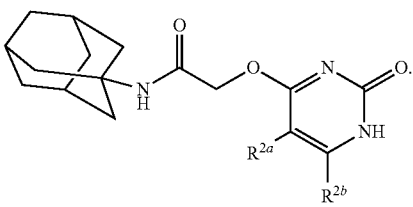

In various aspects, the compound has a structure represented by a formula:

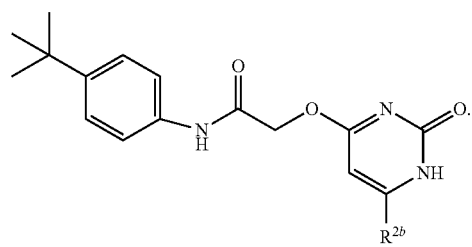

In various aspects, the compound has a structure represented by a formula:

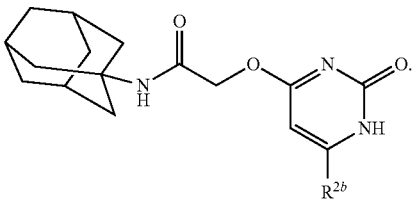

In various aspects, the compound has a structure represented by a formula:

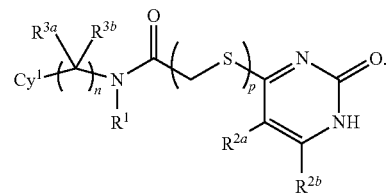

In various aspects, the compound has a structure represented by a formula:

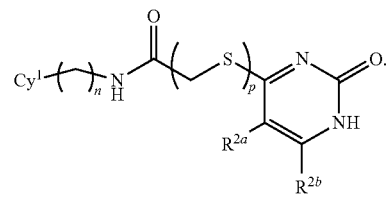

In various aspects, the compound has a structure represented by a formula:

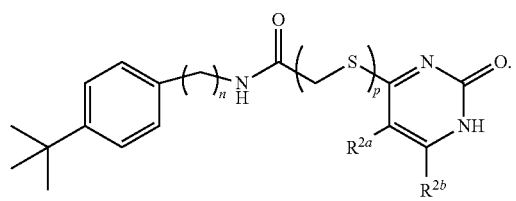

In various aspects, the compound has a structure represented by a formula:

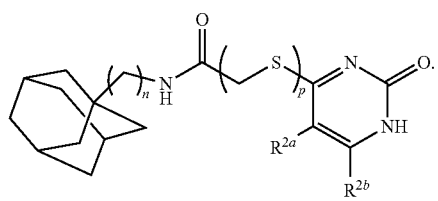

In various aspects, the compound has a structure represented by a formula:

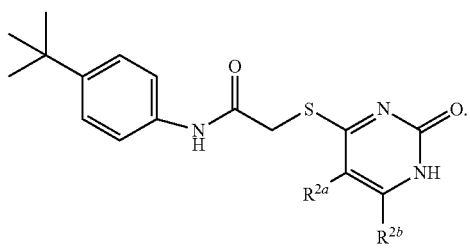

In various aspects, the compound has a structure represented by a formula:

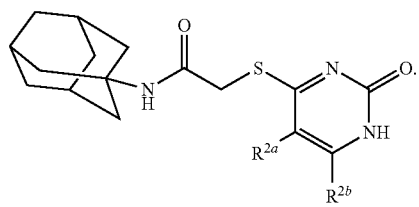

In various aspects, the compound has a structure represented by a formula:

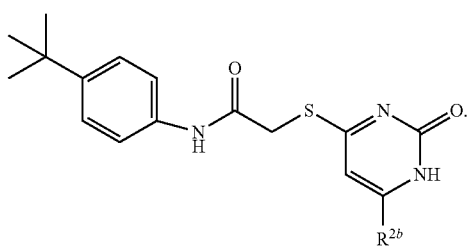

In various aspects, the compound has a structure represented by a formula:

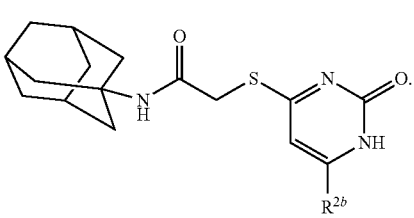

In various aspects, the compound is selected from:

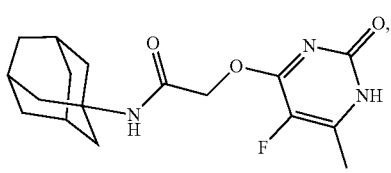

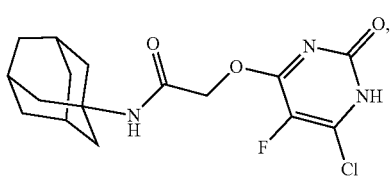

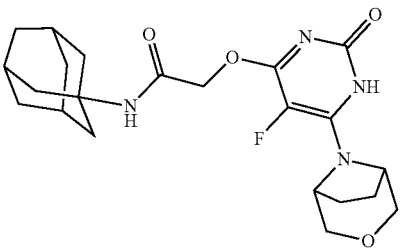

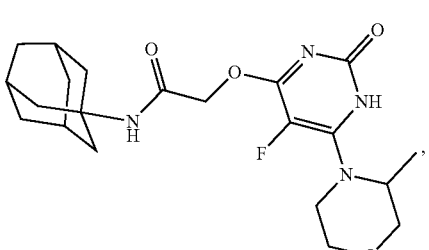

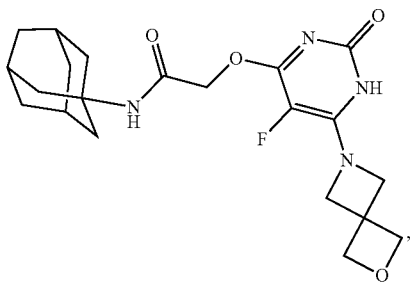

37
-continued
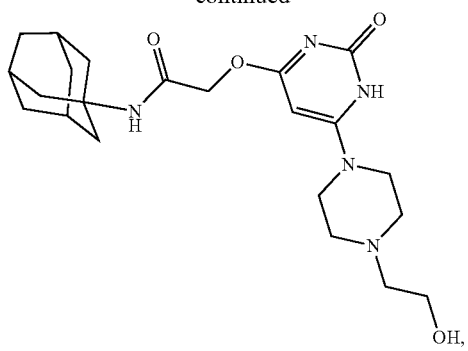
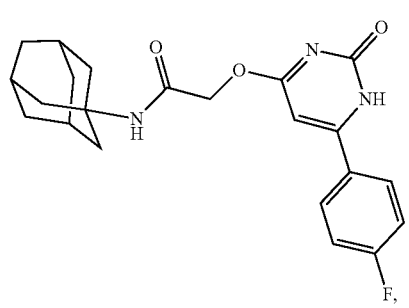
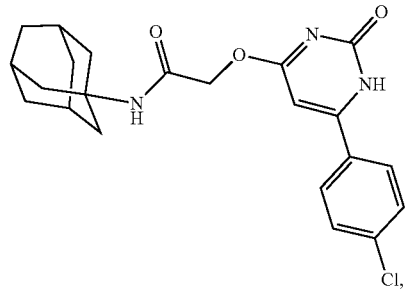
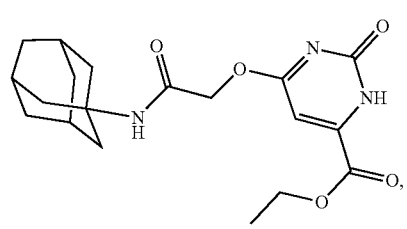
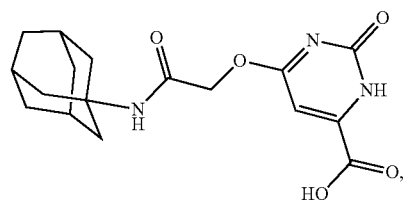
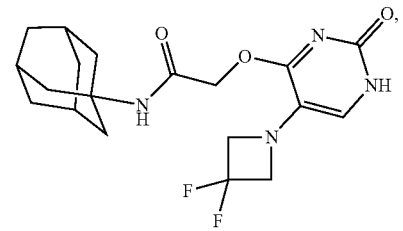
38
-continued
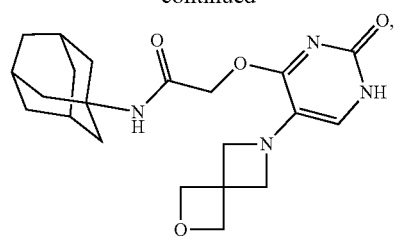
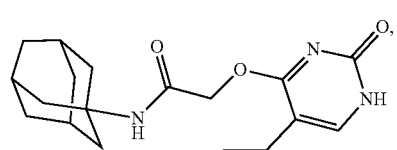
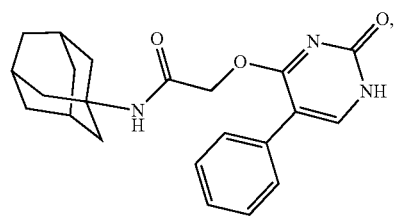
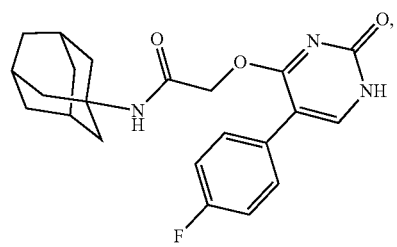
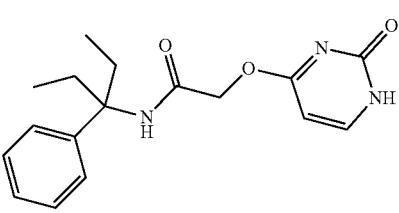
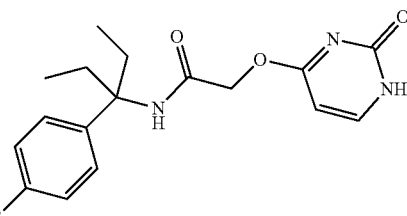
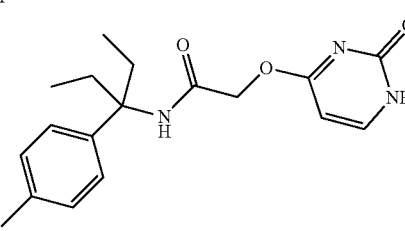

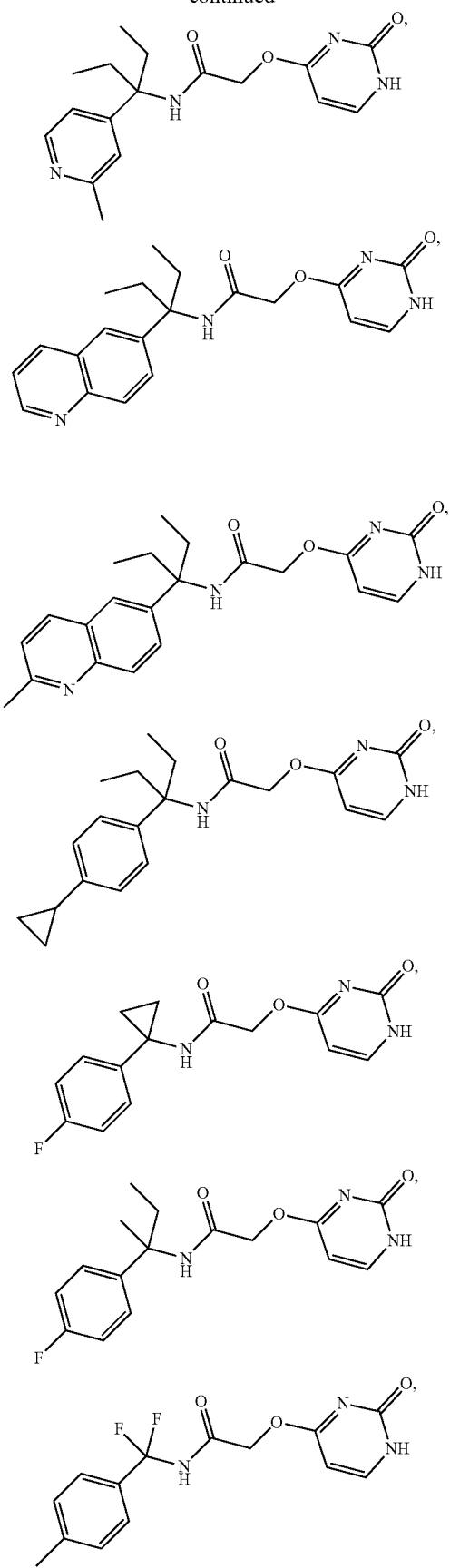
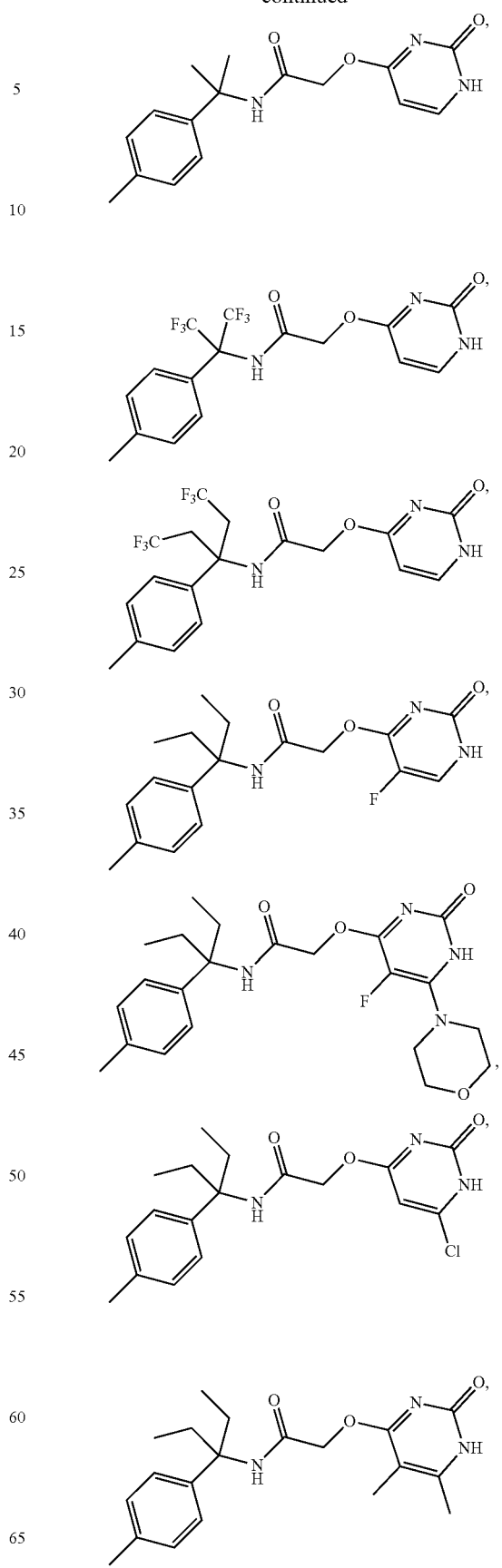

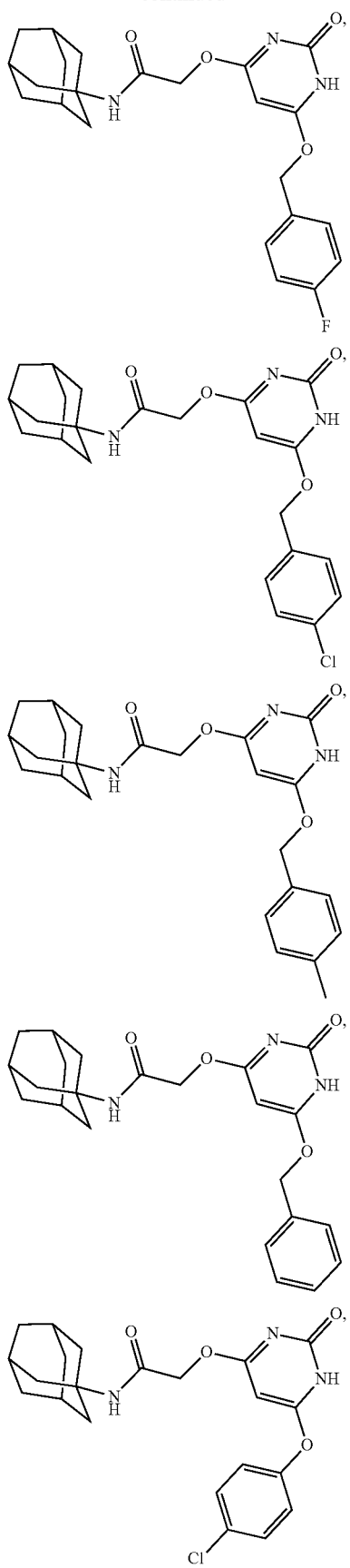
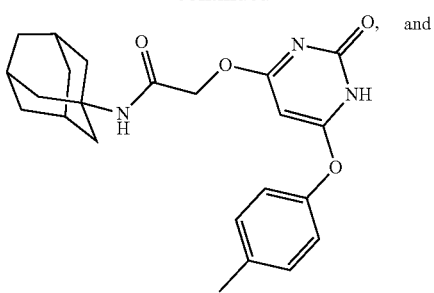
In various aspects, the compound is selected from:

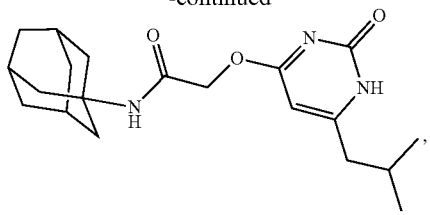
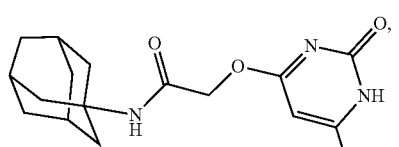
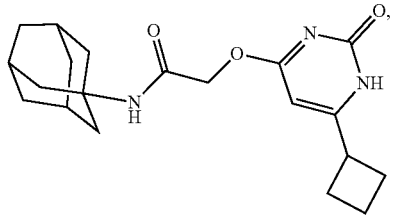
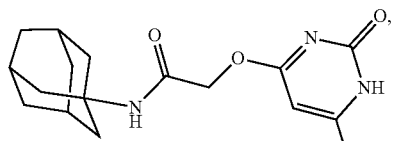
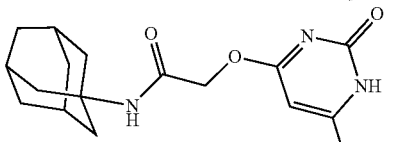
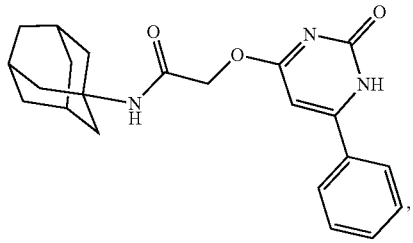
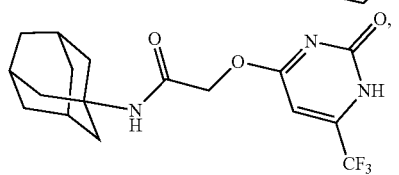
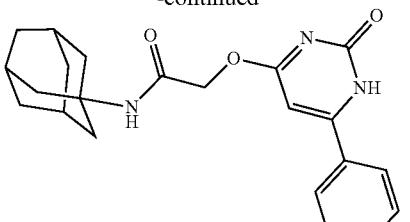
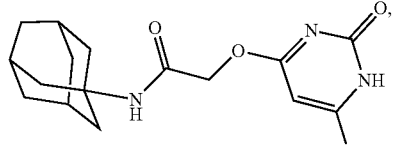
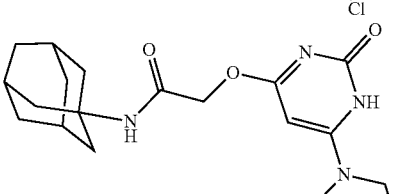
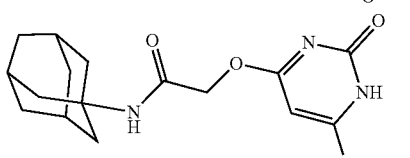
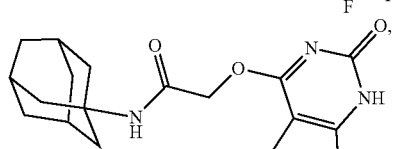
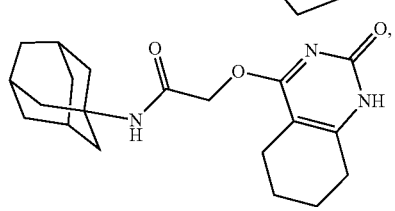
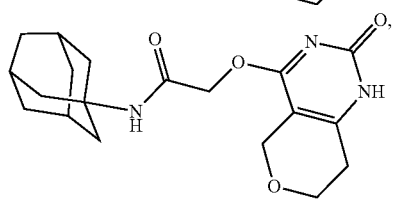
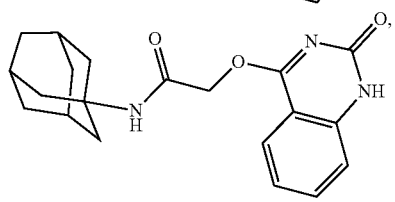

-continued
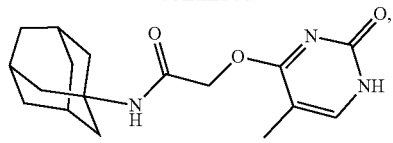
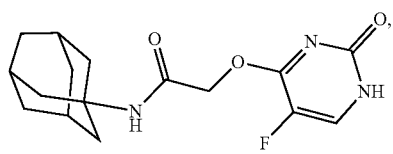
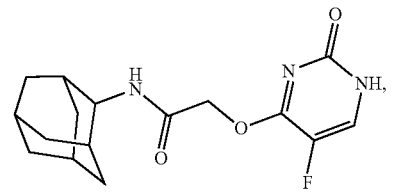
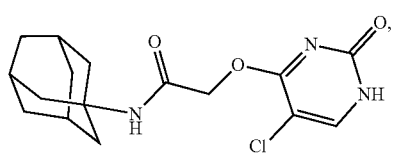
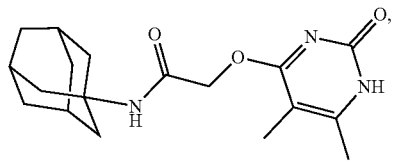
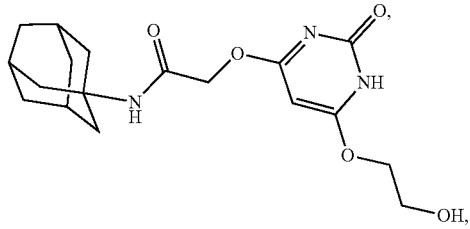
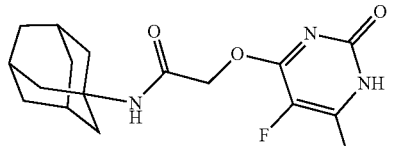
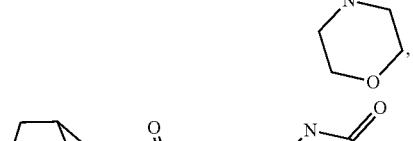
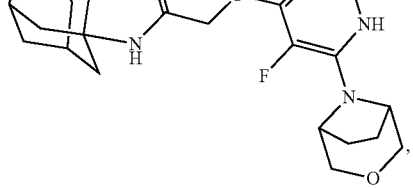
-continued
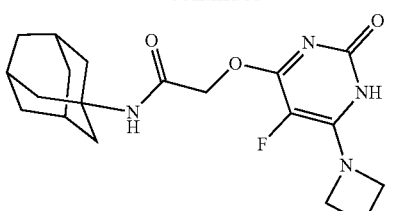
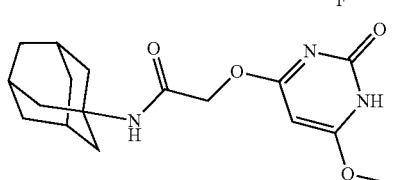
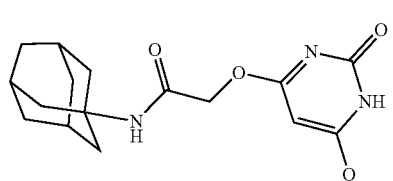
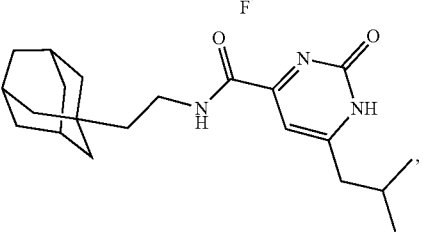
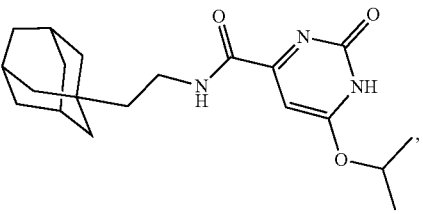
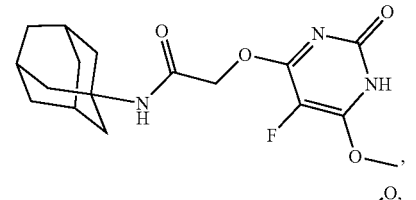
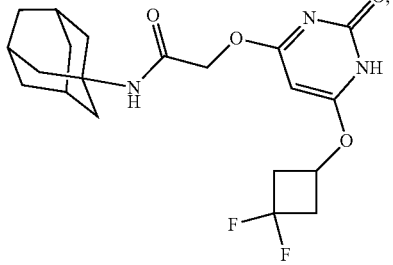

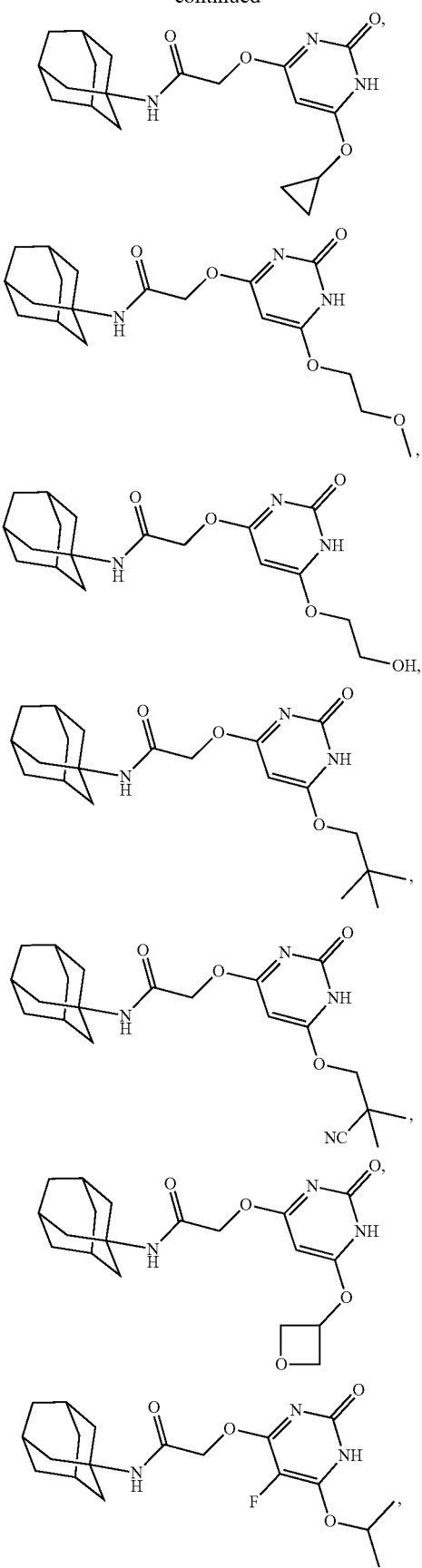

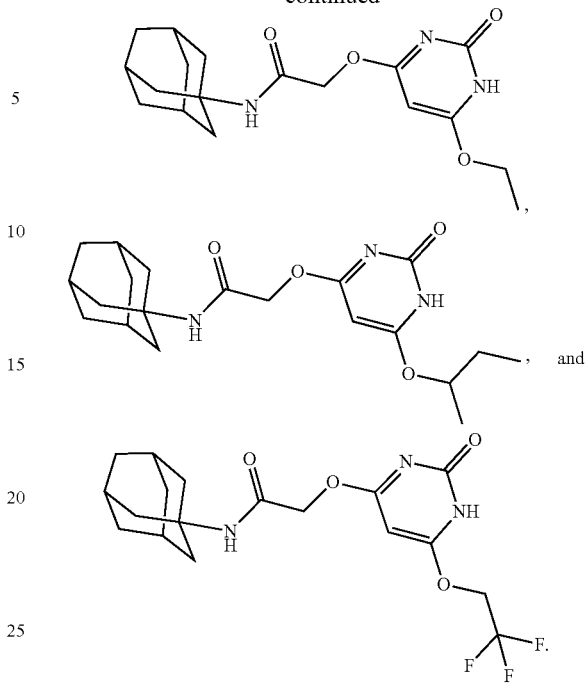

In various aspects, the compound is:

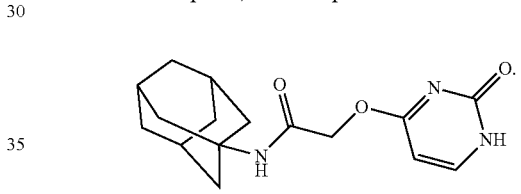

In one aspect, n is 0, 1, or 2. In a further aspect, n is 0 or 1. In yet a further aspect, n is 1 or 2. In a still further aspect, n is 0 or 2. In yet a further aspect, n is 2. In an even further aspect, n is 1. In a still further aspect, n is 0.

In one aspect p is 0 or 1. In a further aspect, p is 0. In a still further aspect, p is 1.

a. A Groups

In one aspect, A, is O, S, or NH. In a further aspect, A is O or S. In a still further aspect, A is O or NH. In yet a further aspect, A is S or NH. In an even further aspect, A is O. In a still further aspect, A is S. In yet a further aspect, A is NH.

b. $R^1$ Groups

In one aspect, $R^1$ is selected from hydrogen and C1-C4 alkyl. In a further aspect, $R^1$ is selected from hydrogen, methyl, ethyl, n-propyl, and isopropyl. In a still further aspect, $R^1$ is selected from hydrogen, methyl, and ethyl. In yet a further aspect, $R^1$ is selected from hydrogen and ethyl. In an even further aspect, $R^1$ is selected from hydrogen and methyl.

In various aspects, $R^1$ is C1-C4 alkyl. In a further aspect, $R^1$ is selected from methyl, ethyl, n-propyl, and isopropyl. In a still further aspect, $R^1$ is selected from methyl and ethyl. In yet a further aspect, $R^1$ is ethyl. In an even further aspect, $R^1$ is methyl.

c. $R^{2A}$ and $R^{2B}$ Groups

In one aspect, each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —$OCy^2$, —$OAr^1$, —O(C1-C4 alkyl)$OR^{10}$, —O(C1-

C4 alkyl)Ar$^1$, —CO$_2$R$^{10}$, and Cy$^2$. In a further aspect, each of R$^{2a}$ and R$^{2b}$ is independently selected from hydrogen, halogen, C1-C4 alkyl, C1-C4 haloalkyl, C1-C4 alkoxy, C1-C4 haloalkoxy, C1-C4 cyanoalkoxy, —OCy$^2$, —OAr$^1$, —O(C1-C4 alkyl)OR$^{10}$, —O(C1-C4 alkyl)Ar$^1$, —CO$_2$R$^{10}$, and Cy$^2$. In a still further aspect, each of R$^{2a}$ and R$^{2b}$ is independently selected from hydrogen, —F, —Cl, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, methoxy, ethoxy, n-propoxy, isopropoxy, —OCH$_2$F, —OCH$_2$Cl, —OCH$_2$CH$_2$F, —OCH$_2$CH$_2$Cl, —OCH$_2$CH$_2$CH$_2$F, —OCH$_2$CH$_2$CH$_2$Cl, —OCH(CH$_3$)CH$_2$F, —OCH(CH$_3$)CH$_2$Cl, —OCH$_2$CN, —OCH$_2$CH$_2$CN, —OCH$_2$CH$_2$CH$_2$CN, —OCH(CH$_3$)CH$_2$CN, —OCy$^2$, —OAr$^1$, —OCH$_2$OR$^{10}$, —OCH$_2$CH$_2$OR$^{10}$, —OCH$_2$CH$_2$CH$_2$OR$^{10}$, —OCH(CH$_3$)CH$_2$OR$^{10}$, —OCH$_2$Ar$^1$, —OCH$_2$CH$_2$Ar$^1$, —OCH$_2$CH$_2$CH$_2$Ar$^1$, —OCH(CH$_3$)CH$_2$Ar$^1$, —CO$_2$R$^{10}$, and Cy$^2$. In yet a further aspect, each of R$^{2a}$ and R$^{2b}$ is independently selected from hydrogen, —F, —Cl, methyl, ethyl, —CH$_2$F, —CH$_2$Cl, —CH$_2$CH$_2$F, —CH$_2$CH$_2$Cl, methoxy, ethoxy, —OCH$_2$F, —OCH$_2$Cl, —OCH$_2$CH$_2$F, —OCH$_2$CH$_2$Cl, —OCH$_2$CN, —OCH$_2$CH$_2$CN, —OCy$^2$, —OAr$^1$, —OCH$_2$OR$^{10}$, —OCH$_2$CH$_2$OR$^{10}$, —OCH$_2$CH$_2$CH$_2$OR$^{10}$, —OCH(CH$_3$)CH$_2$OR$^{10}$, —OCH$_2$Ar$^1$, —OCH$_2$CH$_2$Ar$^1$, —OCH$_2$CH$_2$CH$_2$Ar$^1$, —OCH(CH$_3$)CH$_2$Ar$^1$, —CO$_2$R$^{10}$, and Cy$^2$. In an even further aspect, each of R$^{2a}$ and R$^{2b}$ is independently selected from hydrogen, —F, —Cl, methyl, —CH$_2$F, —CH$_2$Cl, methoxy, —OCH$_2$F, —OCH$_2$Cl, —OCH$_2$CN, —OCy$^2$, —OAr$^1$, —OCH$_2$OR$^{10}$, —OCH$_2$CH$_2$OR$^{10}$, —OCH$_2$CH$_2$CH$_2$OR$^{10}$, —OCH(CH$_3$)CH$_2$OR$^{10}$, —OCH$_2$Ar$^1$, —OCH$_2$CH$_2$Ar$^1$, —OCH$_2$CH$_2$CH$_2$Ar$^1$, —OCH(CH$_3$)CH$_2$Ar$^1$, —CO$_2$R$^{10}$, and Cy$^2$.

In one aspect, each of R$^{2a}$ and R$^{2b}$ is independently selected from hydrogen, halogen, C1-C6 alkyl, C1-C4 haloalkyl, C1-C4 alkoxy, —OAr$^1$, —O(C1-C4 alkyl)OR$^{10}$, —O(C1-C4 alkyl)Ar$^1$, —CO$_2$R$^{10}$, and Cy$^2$, or R$^{2a}$ and R$^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, CJ-C4 haloalkyl, CJ-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In one aspect, each of R$^{2a}$ and R$^{2b}$ is independently selected from hydrogen, halogen, C1-C6 alkyl, C1-C4 haloalkyl, C1-C4 alkoxy, —OAr$^1$, —O(C1-C4 alkyl)OR$^{10}$, —O(C1-C4 alkyl)Ar$^1$, —CO$_2$R$^{10}$, and Cy$^2$. In a further aspect, each of R$^{2a}$ and R$^{2b}$) is independently selected from hydrogen, halogen, C1-C4 alkyl, C1-C4 haloalkyl, C1-C4 alkoxy, —OAr$^1$, —O(C1-C4 alkyl)OR$^{10}$, —O(C1-C4 alkyl) Ar$^1$, —CO$_2$R$^{10}$, and Cy$^2$. In a still further aspect, each of R$^{2a}$ and R$^{2b}$ is independently selected from hydrogen, —F, —Cl, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, methoxy, ethoxy, n-propoxy, isopropoxy, —OAr$^1$, —OCH$_2$OR$^{10}$, —OCH$_2$CH$_2$OR$^{10}$, —OCH$_2$CH$_2$CH$_2$OR$^{10}$, —OCH(CH$_3$)CH$_2$OR$^{10}$, —OCH$_2$Ar$^1$, —OCH$_2$CH$_2$Ar$^1$, —OCH$_2$CH$_2$CH$_2$Ar$^1$, —OCH(CH$_3$)CH$_2$Ar$^1$, —CO$_2$R$^{10}$, and Cy$^2$. In yet a further aspect, each of R$^{2a}$ and R$^{2b}$ is independently selected from hydrogen, —F, —Cl, methyl, ethyl, —CH$_2$F, —CH$_2$Cl, —CH$_2$CH$_2$F, —CH$_2$CH$_2$CJ, methoxy, ethoxy, —OAr$^1$, —OCH$_2$OR$^{10}$, —OCH$_2$CH$_2$OR$^{10}$, —OCH$_2$Ar$^1$, —OCH$_2$CH$_2$Ar$^1$, —CO$_2$R$^{10}$, and Cy$^2$. In an even further aspect, each of R$^{2a}$ and R$^{2b}$ is independently selected from hydrogen, —F, —Cl, methyl, —CH$_2$F, —CH$_2$Cl, methoxy, —OAr$^1$, —OCH$_2$OR$^{10}$, —OCH$_2$Ar$^1$, —CO$_2$R$^{10}$, and Cy$^2$.

In one aspect, each of R$^{2a}$ and R$^{2b}$ is independently selected from hydrogen, halogen, C1-C6 alkyl, C1-C4 haloalkyl, —CO$_2$R$^{10}$, and Cy$^2$. In a further aspect, each of R$^{2a}$ and R$^{2b}$ is independently selected from hydrogen, halogen, C1-C4 alkyl, C1-C4 haloalkyl, —CO$_2$R$^{10}$, and Cy$^2$. In a still further aspect, each of R$^{2a}$ and R$^{2b}$ is independently selected from hydrogen, —F, —Cl, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CO$_2$R$^{10}$, and Cy$^2$. In yet a further aspect, each of R$^{2a}$ and R$^{2b}$ is independently selected from hydrogen, —F, —Cl, methyl, ethyl, —CH$_2$F, —CH$_2$Cl, —CH$_2$CH$_2$F, —CH$_2$CH$_2$Cl, —CO$_2$R$^{10}$, and Cy$^2$. In an even further aspect, each of R$^{2a}$ and R$^{2b}$ is independently selected from hydrogen, —F, —Cl, methyl, —CH$_2$F, —CH$_2$Cl, —CO$_2$R$^{10}$, and Cy$^2$.

In various aspects, each of R$^{2a}$ and R$^{2b}$ is independently selected from hydrogen, C1-C4 alkoxy, —OAr$^1$, —O(C1-C4 alkyl)OR$^{10}$, and —O(C1-C4 alkyl)Ar$^1$. In a further aspect, each of R$^{2a}$ and R$^{2b}$ is independently selected from hydrogen, C1-C4 alkoxy, —OAr$^1$, —O(C1-C4 alkyl)OR$^{10}$, and —O(C1-C4 alkyl)Ar$^1$. In a still further aspect, each of R$^{2a}$ and R$^{2b}$ is independently selected from hydrogen, methoxy, ethoxy, n-propoxy, isopropoxy, —OAr$^1$, —OCH$_2$OR$^{10}$, —OCH$_2$CH$_2$OR$^{10}$, —OCH$_2$CH$_2$CH$_2$OR$^{10}$, —OCH(CH$_3$)CH$_2$OR$^{10}$, —OCH$_2$Ar$^1$, —OCH$_2$CH$_2$Ar$^1$, —OCH$_2$CH$_2$CH$_2$Ar$^1$, and —OCH(CH$_3$)CH$_2$Ar$^1$. In yet a further aspect, each of R$^{2a}$ and R$^{2b}$ is independently selected from hydrogen, methoxy, ethoxy, —OAr$^1$, —OCH$_2$OR$^{10}$, —OCH$_2$CH$_2$OR$^{10}$, —OCH$_2$Ar$^1$, and —OCH$_2$CH$_2$Ar$^1$. In an even further aspect, each of R$^{2a}$ and R$^{2b}$ is independently selected from hydrogen, methoxy, —OAr$^1$, —OCH$_2$OR$^{10}$, and —OCH$_2$Ar$^1$.

In various aspects, each of R$^{2a}$ and R$^{2b}$ is independently selected from hydrogen, halogen, C1-C6 alkyl, and C1-C4 haloalkyl. In a further aspect, each of R$^{2a}$ and R$^{2b}$ is independently selected from hydrogen, halogen, C1-C4 alkyl, and C1-C4 haloalkyl. In a still further aspect, each of R$^{2a}$ and R$^{2b}$ is independently selected from hydrogen, —F, —Cl, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, and —CH(CH$_3$)CH$_2$Cl. In yet a further aspect, each of R$^{2a}$ and R$^{2b}$ is independently selected from hydrogen, —F, —Cl, methyl, ethyl, —CH$_2$F, —CH$_2$Cl, —CH$_2$CH$_2$F, and —CH$_2$CH$_2$Cl. In an even further aspect, each of R$^{2a}$ and R$^{2b}$ is independently selected from hydrogen, —F, —Cl, methyl, —CH$_2$F, and —CH$_2$Cl.

In various aspects, each of R$^{2a}$ and R$^{2b}$ is independently selected from hydrogen, halogen, and C1-C4 haloalkyl. In a still further aspect, each of R$^{2a}$ and R$^{2b}$ is independently selected from hydrogen, —F, —Cl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, and —CH(CH$_3$)CH$_2$Cl. In yet a further aspect, each of R$^{2a}$ and R$^{2b}$ is independently selected from hydrogen, —F, —Cl, —CH$_2$F, —CH$_2$Cl, —CH$_2$CH$_2$F, and —CH$_2$CH$_2$Cl. In an even further aspect, each of R$^{2a}$ and R$^{2b}$ is independently selected from hydrogen, —F, —Cl, —CH$_2$F, and —CH$_2$Cl.

In various aspects, each of R$^{2a}$ and R$^{2b}$ is independently selected from hydrogen and C1-C4 haloalkyl. In a still further aspect, each of $R^{2a}$ and $R^{2b}$ is independently selected from hydrogen, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, and —CH(CH$_3$)CH$_2$Cl. In yet a further aspect, each of $R^{2a}$ and $R^{2b}$ is independently selected from hydrogen, —CH$_2$F, —CH$_2$Cl, —CH$_2$CH$_2$F, and —CH$_2$CH$_2$Cl. In an even further aspect, each of $R^{2a}$ and $R^{2b}$ is independently selected from hydrogen, —CH$_2$F, and —CH$_2$Cl.

In various aspects, each of $R^{2a}$ and $R^{2b}$ is independently selected from hydrogen and halogen. In a still further aspect, each of $R^{2a}$ and $R^{2b}$ is independently selected from hydrogen, —F, —Cl, and —Br. In yet a further aspect, each of $R^{2a}$ and $R^{2b}$ is independently selected from hydrogen, —F, and —Cl. In an even further aspect, each of $R^{2a}$ and $R^{2b}$ is independently selected from hydrogen and —Cl. In a still further aspect, each of $R^{2a}$ and $R^{2b}$ is independently selected from hydrogen and —F.

In various aspects, each of $R^{2a}$ and $R^{2b}$ is independently selected from hydrogen and C1-C6 alkyl. In a further aspect, each of $R^{2a}$ and $R^{2b}$ is independently selected from hydrogen and C1-C4 alkyl. In a still further aspect, each of $R^{2a}$ and $R^{2b}$ is independently selected from hydrogen, methyl, ethyl, n-propyl, and i-propyl. In yet a further aspect, each of $R^{2a}$ and $R^{2b}$ is independently selected from hydrogen and methyl, ethyl. In an even further aspect, each of $R^{2a}$ and $R^{2b}$ is independently selected from hydrogen and methyl.

In a further aspect, $R^{2a}$ is hydrogen. In a still further aspect, $R^{2b}$ is hydrogen. In yet a further aspect, each of $R^{2a}$ and $R^{2b}$ is hydrogen.

In a further aspect, $R^{2b}$ is C1-C4 alkyl. In a still further aspect, $R^{2b}$ is selected from methyl, ethyl, n-propyl, and isopropyl. In yet a further aspect, $R^{2b}$ is selected from methyl and ethyl. In an even further aspect, $R^{2b}$ is ethyl. In a still further aspect, $R^{2b}$ is methyl.

In one aspect, $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, or 2 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0 or 1 group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with a group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are unsubstituted.

In various aspects, $R^{2a}$ and $R^{2b}$ are covalently bonded and, together with the intermediate atoms, comprise a C5-C6 cycloalkyl or a C2-C5 heterocycloalkyl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{2a}$ and $R^{2b}$ are covalently bonded and, together with the intermediate atoms, comprise a C5-C6 cycloalkyl or a C2-C5 heterocycloalkyl, and are substituted with 0, 1, or 2 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{2a}$ and $R^{2b}$ are covalently bonded and, together with the intermediate atoms, comprise a C5-C6 cycloalkyl or a C2-C5 heterocycloalkyl, and are substituted with 0 or 1 group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{2a}$ and $R^{2b}$ are covalently bonded and, together with the intermediate atoms, comprise a C5-C6 cycloalkyl or a C2-C5 heterocycloalkyl, and are substituted with a group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{2a}$ and $R^{2b}$ are covalently bonded and, together with the intermediate atoms, comprise a C5-C6 cycloalkyl or a C2-C5 heterocycloalkyl, and are unsubstituted.

In various aspects, $R^{2a}$ and $R^{2b}$ are covalently bonded and, together with the intermediate atoms, comprise a C5-C6 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{2a}$ and $R^{2b}$ are covalently bonded and, together with the intermediate atoms, comprise a C5-C6 cycloalkyl substituted with 0, 1, or 2 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{2a}$ and $R^{2b}$ are covalently bonded and, together with the intermediate atoms, comprise a C5-C6 cycloalkyl substituted with 0 or 1 group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{2a}$ and $R^{2b}$ are covalently bonded and, together with the intermediate atoms, comprise a C5-C6 cycloalkyl substituted with a group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, R$^{2a}$ and R$^{2b}$ are covalently bonded and, together with the intermediate atoms, comprise an unsubstituted C5-C6 cycloalkyl.

In various aspects, R$^{2a}$ and R$^{2b}$ are covalently bonded and, together with the intermediate atoms, comprise a C2-C5 heterocycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C5 heterocycloalkyls include, but are not limited to, thiirane, oxirane, aziridine, thietane, azetidine, oxetane, pyrrolidine, imidazolidine, tetrahydrothiophene, tetrahydrofuran, piperidine, piperazine, thiane, and morpholine. In a further aspect, R$^{2a}$ and R$^{2b}$ are covalently bonded and, together with the intermediate atoms, comprise a C2-C5 heterocycloalkyl substituted with 0, 1, or 2 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, R$^{2a}$ and R$^{2b}$ are covalently bonded and, together with the intermediate atoms, comprise a C2-C5 heterocycloalkyl substituted with 0 or 1 group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, R$^{2a}$ and R$^{2b}$ are covalently bonded and, together with the intermediate atoms, comprise a C2-C5 heterocycloalkyl substituted with a group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, R$^{2a}$ and R$^{2b}$ are covalently bonded and, together with the intermediate atoms, comprise an unsubstituted C2-C5 heterocycloalkyl.

In various aspects, R$^{2a}$ and R$^{2b}$ are covalently bonded and, together with the intermediate atoms, comprise a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, R$^{2a}$ and R$^{2b}$ are covalently bonded and, together with the intermediate atoms, comprise a C6 aryl or a C2-C5 heteroaryl, and are substituted with 0, 1, or 2 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, R$^{2a}$ and R$^{2b}$ are covalently bonded and, together with the intermediate atoms, comprise a C6 aryl or a C2-C5 heteroaryl, and are substituted with 0 or 1 group selected from selected from halogen, —CN, —NH$_2$, —OH, —NO$_2$, C1-C4 alkyl, C2-C4 alkenyl, C1-C4 haloalkyl, C1-C4 cya-noalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, R$^{2a}$ and R$^{2b}$ are covalently bonded and, together with the intermediate atoms, comprise a C6 aryl or a C2-C5 heteroaryl, and are substituted with a group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, R$^{2a}$ and R$^{2b}$ are covalently bonded and, together with the intermediate atoms, comprise a C6 aryl or a C2-C5 heteroaryl, and are unsubstituted.

In various aspects, R$^{2a}$ and R$^{2b}$ are covalently bonded and, together with the intermediate atoms, comprise a C6 aryl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, R$^{2a}$ and R$^{2b}$ are covalently bonded and, together with the intermediate atoms, comprise a C6 aryl substituted with 0, 1, or 2 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, CJ-C4 hydroxyalkyl, C1-C4 haloalkoxy, C1-C4 alkoxy, C1-C4 alkylamino, (C1-C4)(C1-C4) dialkylamino, and CJ-C4 aminoalkyl. In a still further aspect, R$^{2a}$ and R$^{2b}$ are covalently bonded and, together with the intermediate atoms, comprise a C6 aryl substituted with 0 or 1 group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, R$^{2a}$ and R$^{2b}$ are covalently bonded and, together with the intermediate atoms, comprise a C6 aryl substituted with a group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, R$^{2a}$ and R$^{2b}$ are covalently bonded and, together with the intermediate atoms, comprise an unsubstituted C6 aryl.

In various aspects, R$^{2a}$ and R$^{2b}$ are covalently bonded and, together with the intermediate atoms, comprise a C2-C5 heteroaryl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C5 heteroaryls include, but are not limited to, furan, pyrrole, thiophene, oxazole, isothiazole, pyridine, and triazine. In a further aspect, R$^{2a}$ and R$^{2b}$ are covalently bonded and, together with the intermediate atoms, comprise a C2-C5 heteroaryl substituted with 0, 1, or 2 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, R$^{2a}$ and R$^{2b}$ are covalently bonded and, together with the intermediate atoms, comprise a C2-C5 heteroaryl substituted with 0 or 1 group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{2a}$ and $R^{2b}$ are covalently bonded and, together with the intermediate atoms, comprise a C2-C5 heteroaryl substituted with a group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{2a}$ and $R^{2b}$ are covalently bonded and, together with the intermediate atoms, comprise an unsubstituted C2-C5 heteroaryl.

D. $R^{3a}$ and $R^{3b}$ Groups

In one aspect, each of $R^{3a}$ and $R^{3b}$, when present, is independently selected from hydrogen, halogen, C1-C4 alkyl, and C1-C4 haloalkyl or $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In one aspect, each of $R^{3a}$ and $R^{3b}$, when present, is independently selected from hydrogen, halogen, C1-C4 alkyl, and C1-C4 haloalkyl. In a further aspect, each of $R^{3a}$ and $R^{3b}$, when present, is independently selected from hydrogen, —F, —Cl, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl. In a still further aspect, each of $R^{3a}$ and $R^{3b}$, when present, is independently selected from hydrogen, —F, —Cl, methyl, ethyl, —CH$_2$F, —CH$_2$Cl, —CH$_2$CH$_2$F, and —CH$_2$CH$_2$Cl. In yet a further aspect, each of $R^{3a}$ and $R^{3b}$, when present, is independently selected from hydrogen, —F, —Cl, methyl, —CH$_2$F, and —CH$_2$Cl.

In various aspects, each of $R^{3a}$ and $R^{3b}$, when present, is independently selected from hydrogen, halogen, and C1-C4 haloalkyl. In a further aspect, each of $R^{3a}$ and $R^{3b}$, when present, is independently selected from hydrogen, —F, —Cl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, and —CH(CH$_3$)CH$_2$Cl. In a still further aspect, each of $R^{3a}$ and $R^{3b}$, when present, is independently selected from hydrogen, —F, —Cl, —CH$_2$F, —CH$_2$Cl, —CH$_2$CH$_2$F, and —CH$_2$CH$_2$Cl. In yet a further aspect, each of $R^{3a}$ and $R^{3b}$, when present, is independently selected from hydrogen, —F, —Cl, —CH$_2$F, and —CH$_2$Cl.

In various aspects, each of $R^{3a}$ and $R^{3b}$, when present, is independently selected from hydrogen and C1-C4 haloalkyl. In a further aspect, each of $R^{3a}$ and $R^{3b}$, when present, is independently selected from hydrogen, —CH$_2$F, —CH$_2$Cl, —CH$_2$CH$_2$F, —CH$_2$CH$_2$CJ, —CH$_2$CH$_2$CH$_2$F, —CH$_2$CH$_2$CH$_2$Cl, —CH(CH$_3$)CH$_2$F, and —CH(CH$_3$)CH$_2$Cl. In a still further aspect, each of $R^{3a}$ and $R^{3b}$, when present, is independently selected from hydrogen, —CH$_2$F, —CH$_2$Cl, —CH$_2$CH$_2$F, and —CH$_2$CH$_2$Cl. In yet a further aspect, each of $R^{3a}$ and $R^{3b}$, when present, is independently selected from hydrogen, —CH$_2$F, and —CH$_2$Cl.

In various aspects, each of $R^{3a}$ and $R^{3b}$, when present, is independently selected from hydrogen and halogen. In a further aspect, each of $R^{3a}$ and $R^{3b}$, when present, is independently selected from hydrogen, —F, —Cl, and —Br. In a still further aspect, each of $R^{3a}$ and $R^{3b}$, when present, is independently selected from hydrogen, —F, and —Cl. In yet a further aspect, each of $R^{3a}$ and $R^{3b}$, when present, is independently selected from hydrogen and —Cl. In an even further aspect, each of $R^{3a}$ and $R^{3b}$, when present, is independently selected from hydrogen and —F.

In various aspects, each of $R^{3a}$ and $R^{3b}$, when present, is independently selected from hydrogen and C1-C4 alkyl. In a further aspect, each of $R^{3a}$ and $R^{3b}$, when present, is independently selected from hydrogen, methyl, ethyl, n-propyl, and i-propyl. In a still further aspect, each of $R^{3a}$ and $R^{3b}$, when present, is independently selected from hydrogen, methyl, and ethyl. In yet a further aspect, each of $R^{3a}$ and $R^{3b}$, when present, is independently selected from hydrogen and methyl.

In a further aspect, each of $R^{3a}$ and $R^{3b}$, when present, is hydrogen.

In a further aspect, one of $R^{3a}$ and $R^{3b}$, when present, is hydrogen and one of $R^{3a}$ and $R^{3b}$, when present, is selected from halogen, C1-C4 alkyl, and C1-C4 haloalkyl, or wherein $R^{3a}$ and $R^{3b}$, when present, are covalently bonded and, together with the intermediate atoms, comprise an unsubstituted C3 cycloalkyl.

In one aspect, $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{3a}$ and $R^{3b}$, when present, are covalently bonded and, together with the intermediate atoms, comprise a C3-C4 cycloalkyl substituted with 0, 1, or 2 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{3a}$ and $R^{3b}$, when present, are covalently bonded and, together with the intermediate atoms, comprise a C3-C4 cycloalkyl substituted with 0 or 1 group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{3a}$ and $R^{3b}$, when present, are covalently bonded and, together with the intermediate atoms, comprise a C3-C4 cycloalkyl substituted with a group selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{3a}$ and $R^{3b}$, when present, are covalently bonded and, together with the intermediate atoms, comprise an unsubstituted C3-C4 cycloalkyl.

In a further aspect, each of $R^{3a}$ and $R^{3b}$, when present, is independently selected from halogen, C1-C4 alkyl, and C1-C4 haloalkyl or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

e. $R^{10}$ Groups

In one aspect, each occurrence of $R^{10}$, when present, is independently selected from hydrogen and C1-C4 alkyl. In a further aspect, each occurrence of $R^{10}$, when present, is independently selected from hydrogen, methyl, ethyl, n-propyl, and isopropyl. In a still further aspect, each occurrence of $R^{10}$, when present, is independently selected from hydrogen, methyl, and ethyl. In yet a further aspect, each occurrence of $R^{10}$, when present, is independently selected from hydrogen and ethyl. In an even further aspect, each occurrence of $R^{10}$, when present, is independently selected from hydrogen and methyl.

In various aspects, each occurrence of $R^{10}$, when present, is independently selected from C1-C4 alkyl. In a further aspect, each occurrence of $R^{10}$, when present, is independently selected from methyl, ethyl, n-propyl, and isopropyl. In a still further aspect, each occurrence of $R^{10}$, when present, is independently selected from methyl and ethyl. In yet a further aspect, each occurrence of $R^{10}$, when present, is ethyl. In an even further aspect, each occurrence of $R^{10}$, when present, is methyl.

f. $R^{11A}$, $R^{11B}$, $R^{11C}$, $R^{11D}$, and $R^{11E}$

In one aspect, each of $R^{11a}$, $R^{11b}$, $R^{11c}$, $R^{11d}$, and $R^{11e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl, provided that at least two of $R^{11a}$, $R^{11b}$, $R^{11c}$, $R^{11d}$, and $R^{11e}$ are hydrogen. Thus, in various aspects, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, methyl, ethyl, n-propyl, i-propyl, ethenyl, propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, —CH(CH$_3$)CH$_2$NH$_2$, and C3-C6 cycloalkyl. In a further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, —CH$_2$CH$_2$NH$_2$, and C3-C6 cycloalkyl. In a still further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, methyl, —CH$_2$F, —CH$_2$Cl, —CH$_2$CN, —CH$_2$OH, —OCF$_3$, —OCH$_2$CF$_3$, —OCH$_3$, —NHCH$_3$, —N(CH$_3$)$_2$, —CH$_2$NH$_2$, and C3-C6 cycloalkyl.

In various aspects, each of $R^{11a}$, $R^{11b}$, $R^{11c}$, $R^{11d}$, and $R^{11e}$ is independently selected from hydrogen, halogen, —CN, —NH$_2$, —OH, —NO$_2$, C1-C4 alkyl, C2-C4 alkenyl, and C3-C6 cycloalkyl, provided that at least two of $R^{11a}$, $R^{11b}$, $R^{11c}$, $R^{11d}$ and $R^{11e}$ are hydrogen. Thus, in various further aspects, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, methyl, ethyl, n-propyl, i-propyl, ethenyl, propenyl, isopropenyl, and C3-C6 cycloalkyl. In a further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, methyl, ethyl, ethenyl, and C3-C6 cycloalkyl. In a still further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, methyl, and C3-C6 cycloalkyl.

In various aspects, each of $R^{11a}$, $R^{11b}$, $R^{11c}$, $R^{11d}$, and $R^{11e}$ is independently selected from hydrogen, C1-C4 alkyl, and C2-C4 alkenyl, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, methyl, ethyl, n-propyl, i-propyl, ethenyl, propenyl, and isopropenyl. In a further aspect, each of $R^{11a}$, $R^{11b}$, $R^{11c}$, $R^{11d}$, and $R^{11e}$ is independently selected from hydrogen, methyl, ethyl, and ethenyl. In a still further aspect, each of $R^{11a}$, $R^{11b}$, $R^{11c}$, $R^{11d}$, and $R^{11e}$ is independently selected from hydrogen and methyl.

In various aspects, each of $R^{11a}$, $R^{11b}$, $R^{11c}$, $R^{11d}$, and $R^{11e}$ is independently selected from hydrogen and C3-C6 cycloalkyl, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen and C3-C5 cycloalkyl. In a further aspect, each of $R^{11a}$, $R^{11b}$, $R^{11c}$, $R^{11d}$, and $R^{11e}$ is independently selected from hydrogen and C3-C4 cycloalkyl. In a still further aspect, each of $R^{11a}$, $R^{11b}$, $R^{11c}$, $R^{11d}$, and $R^{11e}$ is independently selected from hydrogen and C4-C6 cycloalkyl. In yet a further aspect, each of $R^{11a}$, $R^{11b}$, $R^{11c}$, $R^{11d}$, and $R^{11e}$ is independently selected from hydrogen and C5-C6 cycloalkyl.

In various aspects, each of $R^{11a}$, $R^{11b}$, $R^{11c}$, $R^{11d}$, and $R^{11e}$ is independently selected from hydrogen, halogen, —CN, —NH$_2$, —OH, —NO$_2$, C1-C4 haloalkyl, and C1-C4 haloalkoxy, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —CH$_2$F, —CH$_2$CJ, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —OCF$_3$, and —OCH$_2$CF$_3$. In a still further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —CH$_2$F, —CH$_2$Cl, —OCF$_3$, and —OCH$_2$CF$_3$.

In various aspects, each of $R^{11a}$, $R^{11b}$, $R^{11c}$, $R^{11d}$, and $R^{11e}$ is independently selected from hydrogen, halogen, C1-C4 haloalkyl, and C1-C4 haloalkoxy, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, —F, —Cl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, each of $R^{11a}$, $R^{11b}$, $R^{11c}$, $R^{11d}$, and $R^{11e}$ is independently selected from hydrogen, —F, —Cl, —CH$_2$F, —CH$_2$Cl, —CH$_2$CH$_2$F, —CH$_2$CH$_2$Cl, —OCF$_3$, and —OCH$_2$CF$_3$. In a still further aspect, each of $R^{11a}$, $R^{11b}$, $R^{11c}$, $R^{11d}$, and $R^{11e}$ is independently selected from hydrogen, —F, —Cl, —CH$_2$F, —CH$_2$Cl, —OCF$_3$, and —OCH$_2$CF$_3$.

In various aspects, each of $R^{11a}$, $R^{11b}$, $R^{11c}$, $R^{11d}$, and $R^{11e}$ is independently selected from hydrogen, halogen, —CN, —NH$_2$, —OH, —NO$_2$, and C1-C4 cyanoalkyl, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —CH$_2$CN, —CH$_2$CH$_2$CN, —CH$_2$CH$_2$CH$_2$CN, and —CH(CH$_3$)CH$_2$CN. In a further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —CH$_2$CN, and —CH$_2$CH$_2$CN. In a still further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, and —CH$_2$CN.

In various aspects, each of $R^{11a}$, $R^{11b}$, $R^{11c}$, $R^{11d}$, and $R^{11e}$ is independently selected from hydrogen and C1-C4 cyanoalkyl, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, —CH$_2$CN, —CH$_2$CH$_2$CN, —CH$_2$CH$_2$CH$_2$CN, and —CH(CH$_3$)CH$_2$CN. In a further aspect, each of $R^{11a}$, $R^{11b}$, $R^{11c}$, $R^{11d}$, and $R^{11e}$ is independently selected from hydrogen, —CH$_2$CN, and —CH$_2$CH$_2$CN. In a still further aspect, each of $R^{11a}$, $R^{11b}$, $R^{11c}$, $R^{11d}$, and $R^{11e}$ is independently selected from hydrogen and —CH$_2$CN.

In various aspects, each of $R^{11a}$, $R^{11b}$, $R^{11c}$, $R^{11d}$, and $R^{11e}$ is independently selected from hydrogen, halogen, —CN, —NH, —OH, —NO$_2$, C1-C4 hydroxyalkyl, and C1-C4 alkoxy, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —CH$_2$OH, —CH$_2$CH$_2$OH, —OCH$_3$, and —OCH$_2$CH$_3$. In a still further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —CH$_2$OH, and —OCH$_3$.

In various aspects, each of $R^{11a}$, $R^{11b}$, $R^{11c}$, $R^{11d}$, and $R^{11e}$ is independently selected from hydrogen, C1-C4 hydroxyalkyl, and C1-C4 alkoxy, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, each of $R^{11a}$, $R^{11b}$, $R^{11c}$, $R^{11d}$, and $R^{11e}$ is independently selected from hydrogen, —CH$_2$OH, —CH$_2$CH$_2$OH, —OCH$_3$, and —OCH$_2$CH$_3$. In a still further aspect, each of $R^{11a}$, $R^{11b}$, $R^{11c}$, $R^{11d}$, and $R^{11e}$ is independently selected from hydrogen, —CH$_2$OH, and —OCH$_3$.

In various aspects, each of $R^{11a}$, $R^{11b}$, $R^{11c}$, $R^{11d}$, and $R^{11e}$ is independently selected from hydrogen, halogen, —CN, —NH$_2$, —OH, —NO$_2$, C1-C4 alkylamino, (C1-C4)(C1-C4) dialkylamino, and C1-C4 aminoalkyl, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each of $R^{11a}$, $R^{11b}$, $R^{11c}$, $R^{11d}$, and $R^{11e}$ is independently selected from hydrogen, —F, —Cl, —NH$_2$, —CN, —OH, —NO$_2$, —NHCH$_3$, —N(CH$_3$)$_2$, and —CH$_2$NH$_2$.

In various aspects, each of $R^{11a}$, $R^{11b}$, $R^{11c}$, $R^{11d}$, and $R^{11e}$ is independently selected from hydrogen, C1-C4 alkylamino, (C1-C4)(C1-C4) dialkylamino, and C1-C4 aminoalkyl, provided that at least two of $R^{11a}$, $R^{11b}$, $R^{11c}$, $R^{11d}$, and $R^{11e}$ are hydrogen. Thus, in various further aspects, each of $R^{11a}$, $R^{11b}$, $R^{11c}$, $R^{11d}$, and $R^{11e}$ is independently selected from hydrogen, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each of $R^{11a}$, $R^{11b}$, $R^{11c}$, $R^{11d}$, and $R^{11e}$ is independently selected from hydrogen, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each of $R^{11a}$, $R^{11b}$, $R^{11c}$, $R^{11d}$, and $R^{11e}$ is independently selected from hydrogen, —NHCH$_3$, —N(CH$_3$)$_2$, and —CH$_2$NH$_2$.

g. $Ar^1$ groups

In one aspect, each occurrence of $Ar^1$, when present, is independently selected from C2-C5 heteroaryl and C6-C12 aryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each occurrence of $Ar^1$, when present, is independently selected from C2-C5 heteroaryl and C6-C12 aryl, and is substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of $Ar^1$, when present, is independently selected from C2-C5 heteroaryl and C6-C12 aryl, and is substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of $Ar^1$, when present, is independently selected from C2-C5 heteroaryl and C6-C12 aryl, and is monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each occurrence of $Ar^1$, when present, is independently selected from C2-C5 heteroaryl and C6-C12 aryl, and is unsubstituted.

In various aspects, each occurrence of $Ar^1$, when present, is C2-C5 heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of heteroaryls include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl. In a further aspect, each occurrence of $Ar^1$, when present, is C2-C5 heteroaryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of $Ar^1$, when present, is C2-C5 heteroaryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of $Ar^1$, when present, is C2-C5 heteroaryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each occurrence of $Ar^1$, when present, is unsubstituted C2-C5 heteroaryl.

In various aspects, each occurrence of $Ar^1$, when present, is C6-C12 aryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of aryls include, but are not limited to, phenyl, naphthyl, phenanthryl, and anthracenyl. In a further aspect, each occurrence of $Ar^1$, when present, is C6-C12 aryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of $Ar^1$, when present, is C6-C12 aryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of $Ar^1$, when present, is C6-C12 aryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each occurrence of $Ar^1$, when present, is unsubstituted C6-C12 aryl.

In various aspects, each occurrence of $Ar^1$, when present, is C6 aryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each occurrence of $Ar^1$, when present, is C6 aryl substituted with 0, 1, or 2 groups independently selected from halogen, CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of $Ar^1$, when present, is C6 aryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of $Ar^1$, when present, is C6 aryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each occurrence of $Ar^1$, when present, is unsubstituted C6 aryl.

h. $Cy^1$ Groups

In one aspect, $Cy^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In a further aspect, $Cy^1$ is selected from C2-C9 heteroaryl, C6 aryl, and adamantyl, and is substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In a still further aspect, $Cy^1$ is selected from C2-C9 heteroaryl, C6 aryl, and adamantyl, and is substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In yet a further aspect, $Cy^1$ is selected from C2-C9 heteroaryl, C6 aryl, and adamantyl, and is monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In an even further aspect, $Cy^1$ is selected from C2-C9 heteroaryl, C6 aryl, and adamantyl, and is unsubstituted.

In various aspects, $Cy^1$ is C2-C9 heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. Examples of C2-C9 heteroaryls include, but are not limited to, thiophene, furan, pyrrole, oxazole, isoxazole, isothiazole, pyridine, pyrimidine, pyridazine, pyrazine, triazine, indole, azaindole, purine, benzofuran, quinolone, isoquinoline, and quinoxaline. In a further aspect, $Cy^1$ is C2-C9 heteroaryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In a still further aspect, $Cy^1$ is C2-C9 heteroaryl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In yet a further aspect, Cy¹ is C2-C9 heteroaryl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In an even further aspect, Cy¹ is unsubstituted C2-C9 heteroaryl.

In various aspects, Cy¹ is C6 aryl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In a further aspect, Cy¹ is C6 aryl substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In a still further aspect, Cy¹ is C6 aryl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In yet a further aspect, Cy¹ is C6 aryl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In an even further aspect, Cy¹ is unsubstituted C6 aryl.

In various aspects, Cy¹ is C6 aryl substituted with 0, 1, 2, or 3 groups independently selected from halogen, C1-C4 alkyl, and C3-C6 cycloalkyl. In a further aspect, Cy¹ is C6 aryl substituted with 0, 1, or 2 groups independently selected from halogen, C1-C4 alkyl, and C3-C6 cycloalkyl. In a still further aspect, Cy¹ is C6 aryl substituted with 0 or 1 group selected from halogen, C1-C4 alkyl, and C3-C6 cycloalkyl. In yet a further aspect, Cy¹ is C6 aryl monosubstituted with a group selected from halogen, C1-C4 alkyl, and C3-C6 cycloalkyl.

In various aspects, Cy¹ is C6 aryl substituted with 0, 1, 2, or 3 groups independently selected from —F, methyl, tert-butyl, and cyclopropyl. In a further aspect, Cy¹ is C6 aryl substituted with 0, 1, or 2 groups independently selected from —F, methyl, tert-butyl, and cyclopropyl. In a still further aspect, Cy¹ is C6 aryl substituted with 0 or 1 group selected from —F, methyl, tert-butyl, and cyclopropyl. In yet a further aspect, Cy¹ is C6 aryl monosubstituted with a group selected from —F, methyl, tert-butyl, and cyclopropyl.

In a further aspect, Cy¹ is C6 aryl para-substituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl.

In a further aspect, Cy¹ is C6 aryl para-substituted with a group selected from halogen, C1-C4 alkyl, and C3-C6 cycloalkyl.

In a further aspect, Cy¹ is C6 aryl para-substituted with a group selected from —F, methyl, tert-butyl, and cyclopropyl.

In a further aspect, Cy¹ is a structure:

In various aspects, Cy¹ is adamantyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In a further aspect, Cy¹ is adamantyl substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In a still further aspect, Cy¹ is adamantyl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl. In yet a further aspect, Cy¹ is adamantyl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl.

In a further aspect, Cy¹ is unsubstituted adamantyl.
In a further aspect, Cy¹ is a structure:

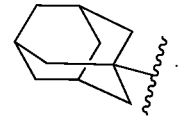

i. Cy² Groups

In one aspect, each occurrence of Cy², when present, is independently selected from C3-C6 cycloalkyl, C3-C6 heterocycloalkyl, and phenyl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each occurrence of Cy², when present, is independently selected from C3-C6 cycloalkyl, C3-C6 heterocycloalkyl, and phenyl, and is substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of Cy², when present, is independently selected from C3-C6 cycloalkyl, C3-C6 heterocycloalkyl, and phenyl, and is substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of Cy², when present, is independently selected from C3-C6 cycloalkyl, C3-C6 heterocycloalkyl, and phenyl, and is monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkyl, C1-C4 alkoxy, C1-C4 alkylamino, (C1-C4)(C1-C4) dialkylamino, and C1-C4 aminoalkyl. In an even further aspect, each occurrence of Cy$^2$, when present, is independently selected from C3-C6 cycloalkyl, C3-C6 heterocycloalkyl, and phenyl, and is unsubstituted.

In various aspects, each occurrence of Cy$^2$, when present, is independently selected from C3-C6 cycloalkyl and C3-C6 heterocycloalkyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each occurrence of Cy$^2$, when present, is independently selected from C3-C6 cycloalkyl and C3-C6 heterocycloalkyl, and is substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of Cy$^2$, when present, is independently selected from C3-C6 cycloalkyl and C3-C6 heterocycloalkyl, and is substituted with 0 or 1 group selected from halogen, —CN, —NH, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of Cy$^2$, when present, is independently selected from C3-C6 cycloalkyl and C3-C6 heterocycloalkyl, and is monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each occurrence of Cy$^2$, when present, is independently selected from C3-C6 cycloalkyl and C3-C6 heterocycloalkyl, and is unsubstituted.

In various aspects, each occurrence of Cy$^2$, when present, is independently C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each occurrence of Cy$^2$, when present, is independently C3-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of Cy$^2$, when present, is independently C3-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of Cy$^2$, when present, is independently C3-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each occurrence of Cy$^2$, when present, is independently unsubstituted C3-C6 cycloalkyl.

In various aspects, each occurrence of Cy$^2$, when present, is independently C3-C6 heterocycloalkyl substituted with 0, 1, 2, or 3 groups independently selected from halogen, —CN, —NH, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls include, but are not limited to, thietane, azetidine, oxetane, pyrrolidine, imidazolidine, tetrahydrothiophene, tetrahydrofuran, piperidine, piperazine, thiane, morpholine, and azaindole. In a further aspect, each occurrence of Cy$^2$, when present, is independently C3-C6 heterocycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of Cy$^2$, when present, is independently C3-C6 heterocycloalkyl substituted with 0 or 1 group selected from halogen, —CN, —NH, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of Cy$^2$, when present, is independently C3-C6 heterocycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each occurrence of Cy$^2$, when present, is independently unsubstituted C3-C6 heterocycloalkyl.

In various aspects, each occurrence of Cy$^2$, when present, is independently phenyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each occurrence of Cy$^2$, when present, is independently phenyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each occurrence of Cy$^2$, when present, is independently phenyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, each occurrence of Cy$^2$, when present, is independently phenyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each occurrence of Cy$^2$, when present, is unsubstituted phenyl.

2. Example Compounds
In one aspect, a compound can be present as one or more of the following structures:
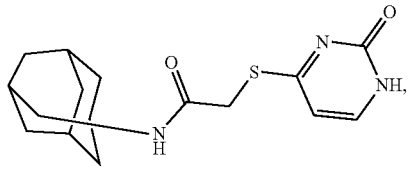
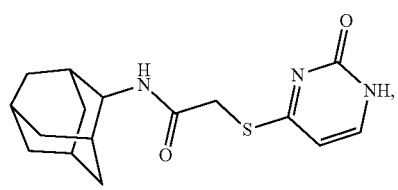
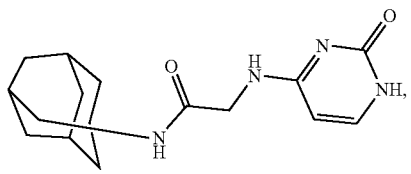
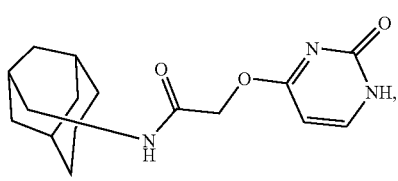
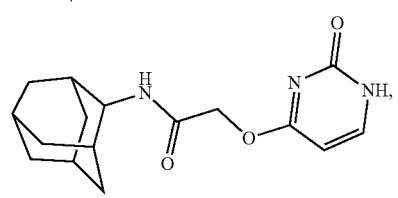
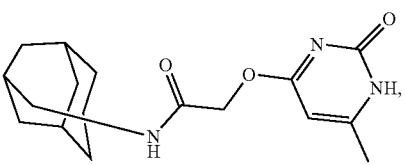
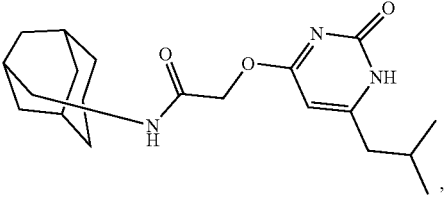
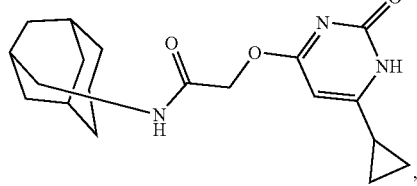
-continued
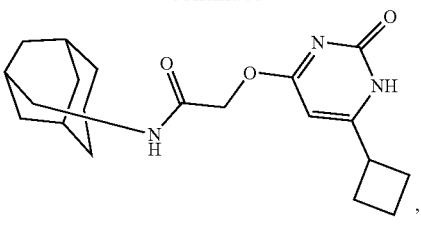
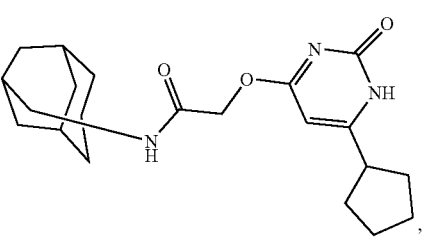
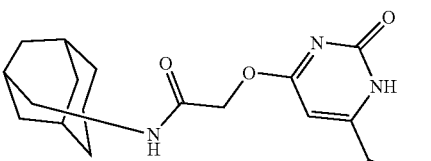
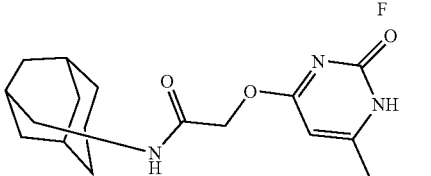
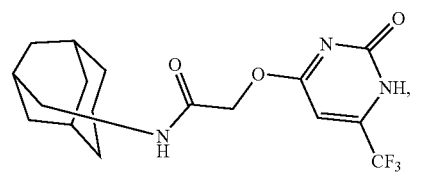
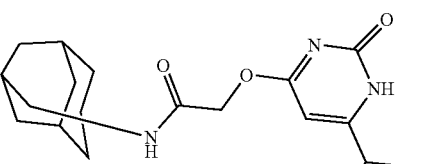
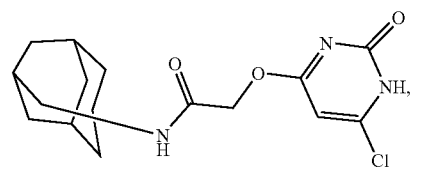

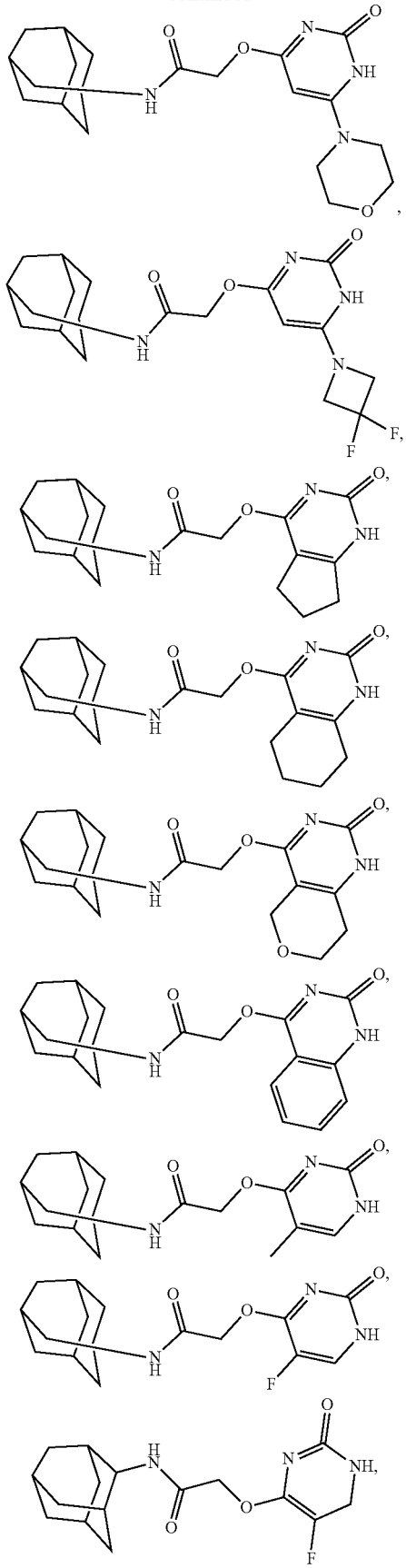
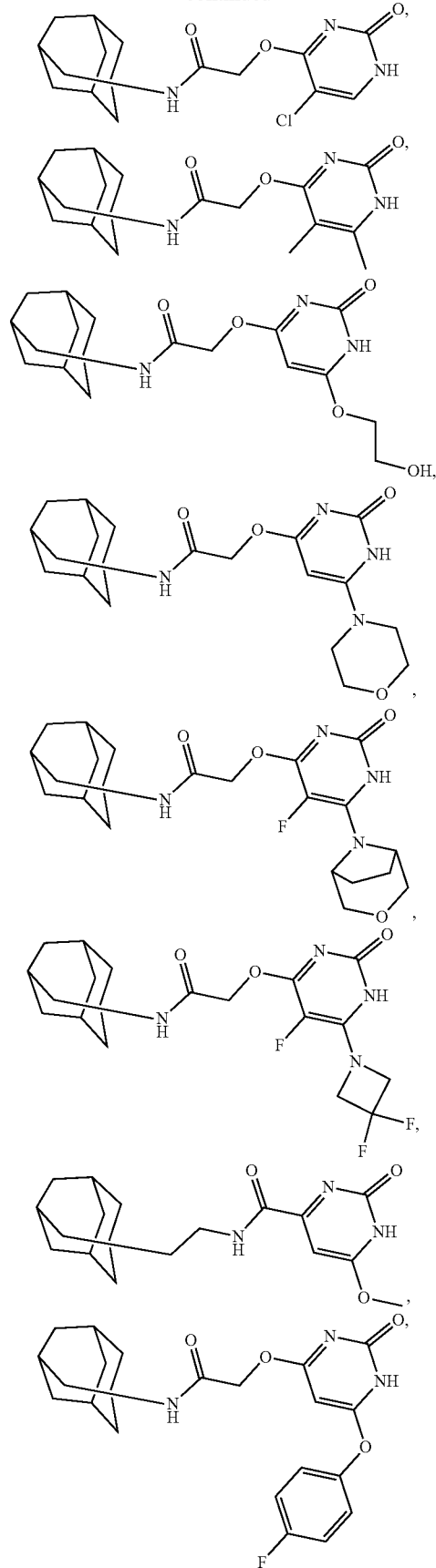

71
-continued
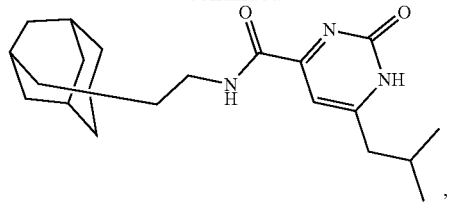
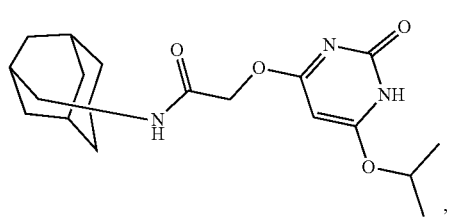
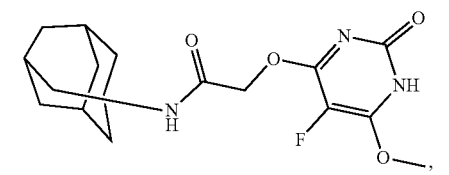
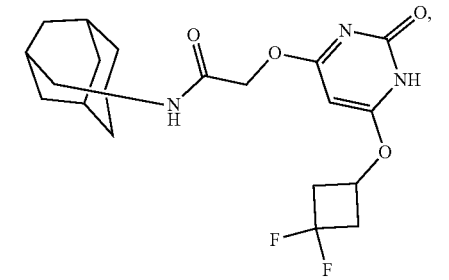
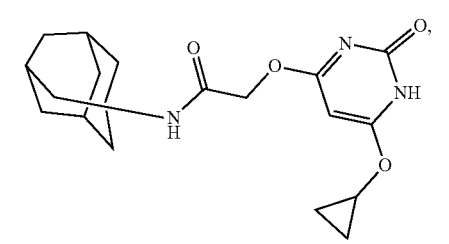
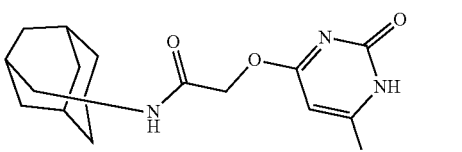
72
-continued
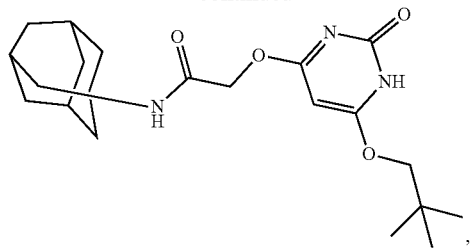
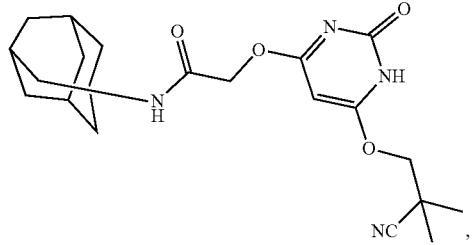
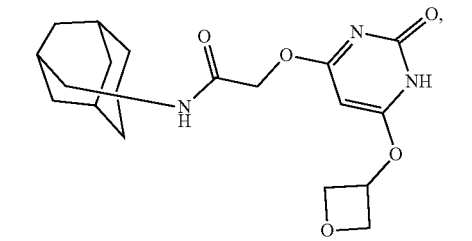
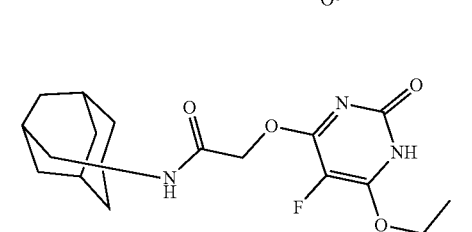
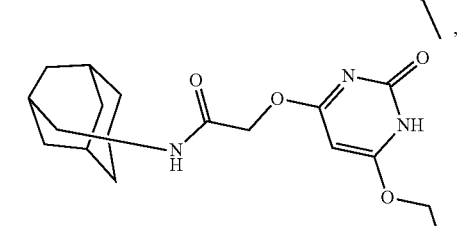
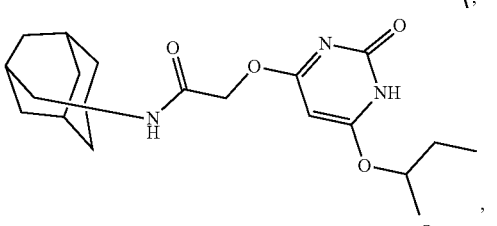
, and
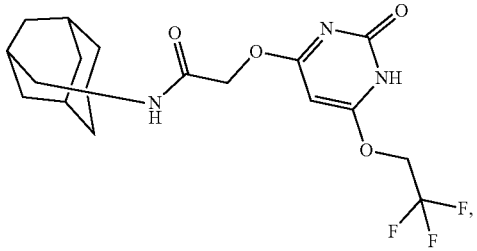
or a pharmaceutically acceptable salt thereof.

In one aspect, a compound can be present as the following structure:

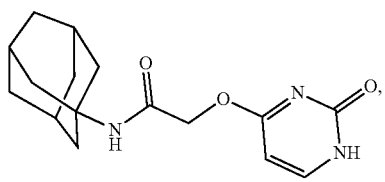 [SMILES: O=C(COc1cc[nH]c(=O)n1)NC12CC3CC(CC(C3)C1)C2]

or a pharmaceutically acceptable salt thereof.

In one aspect, a compound can be present as one or more of the following structures:

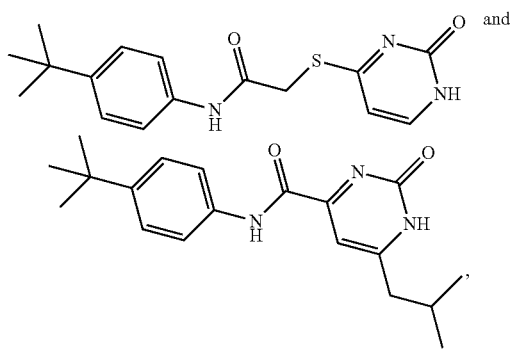

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as antiviral agents, and such activity can be determined using the assay methods described herein below.

In one aspect, a compound can be selected from:

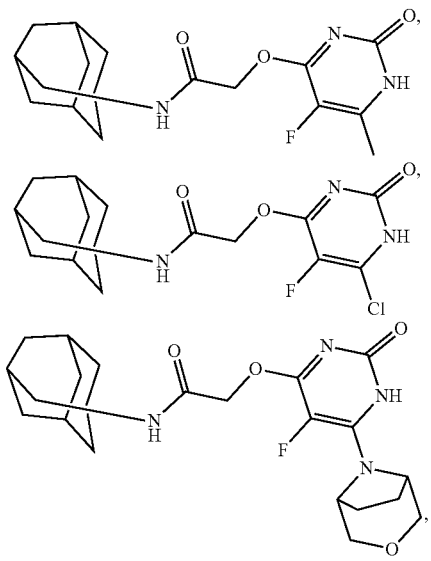

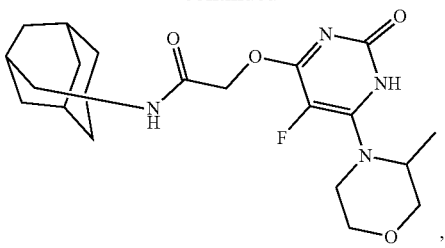

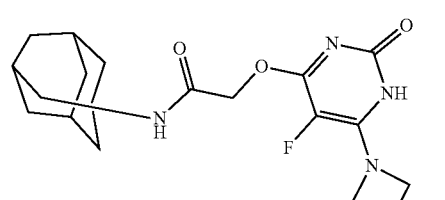

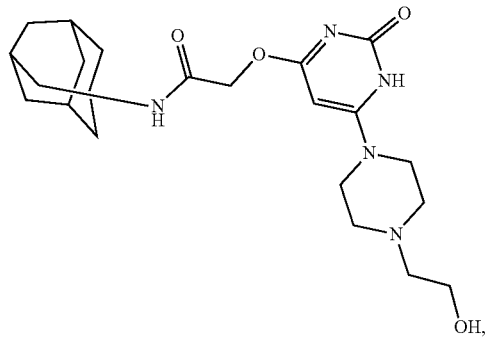

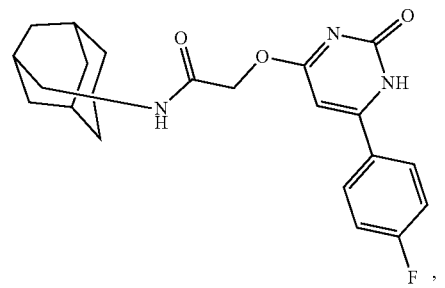

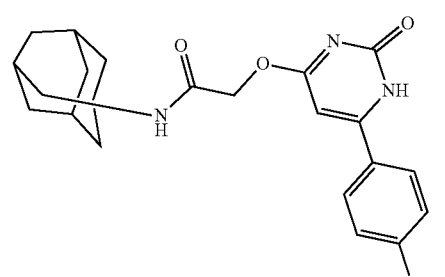

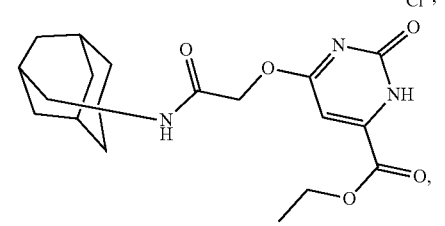

-continued
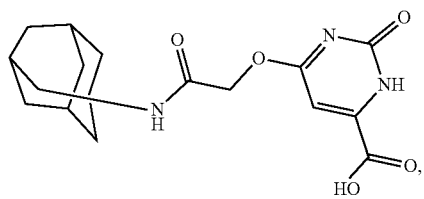
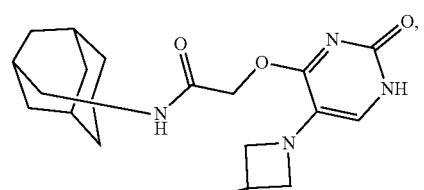
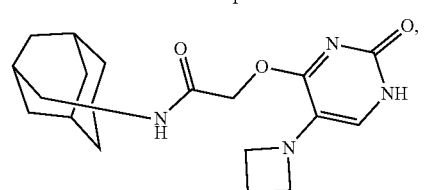
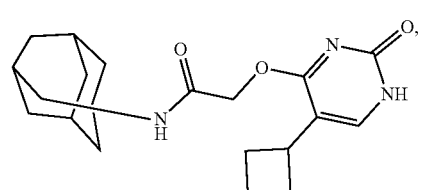
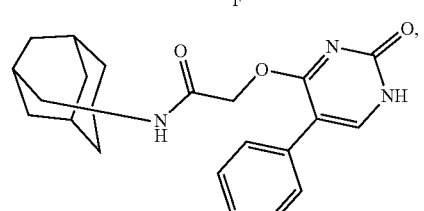
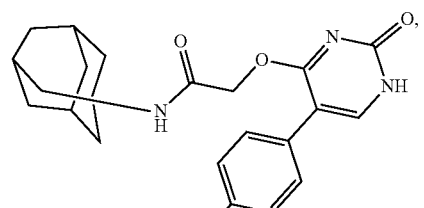
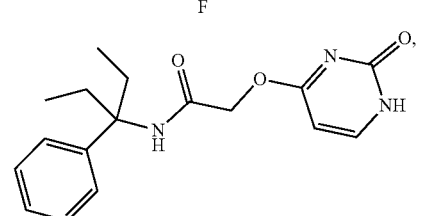
-continued
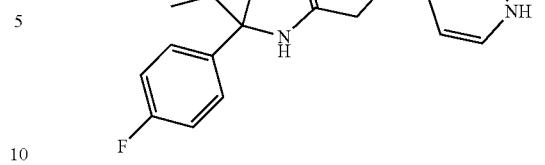
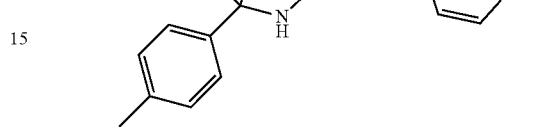
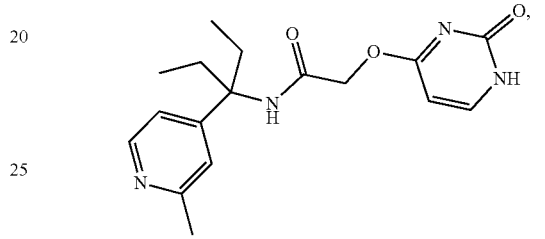
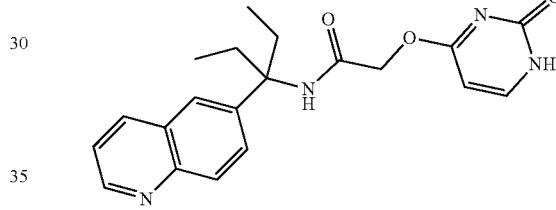
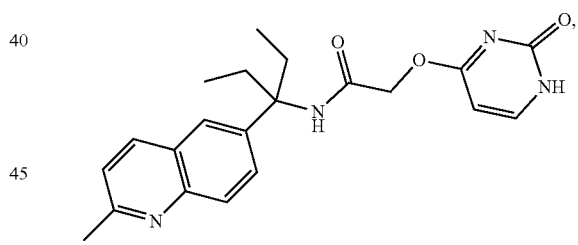
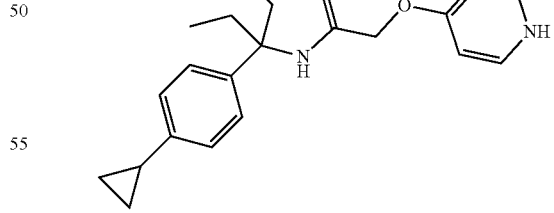
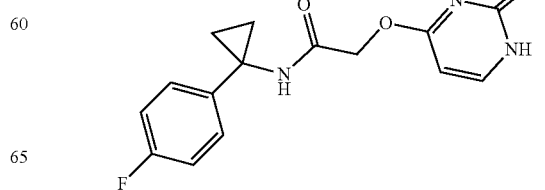

77
-continued
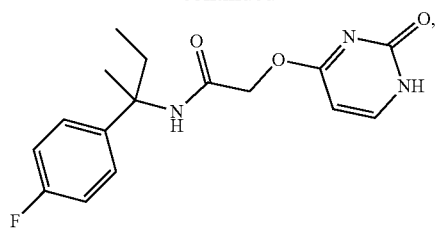
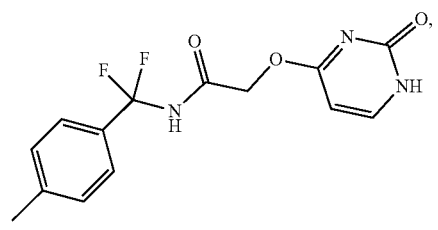
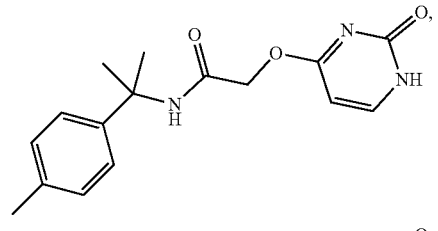
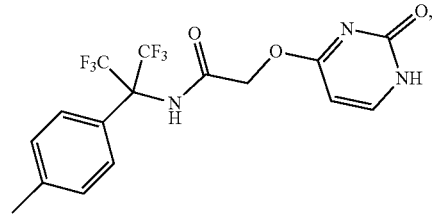
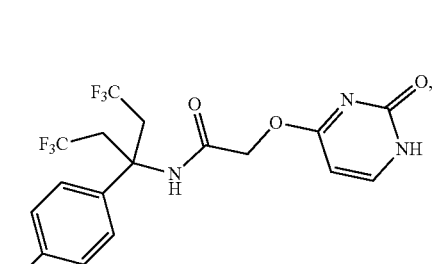
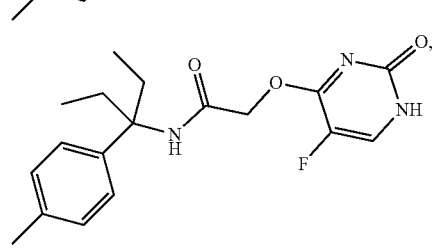
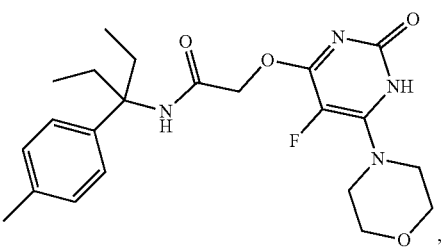
78
-continued
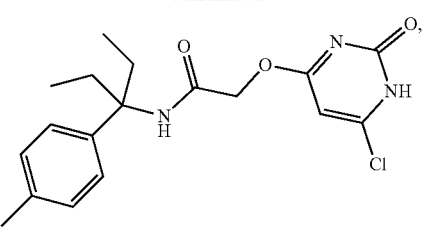
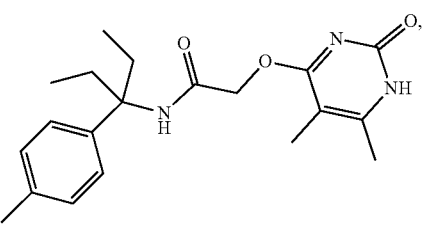
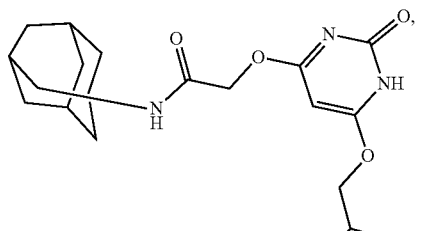
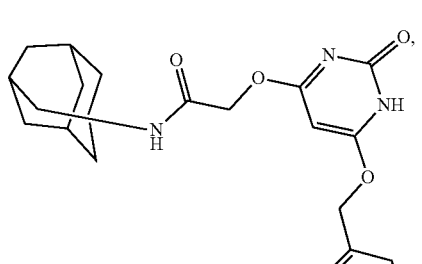
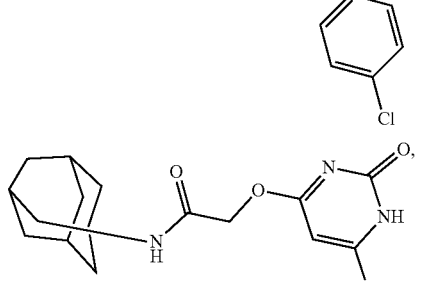

-continued

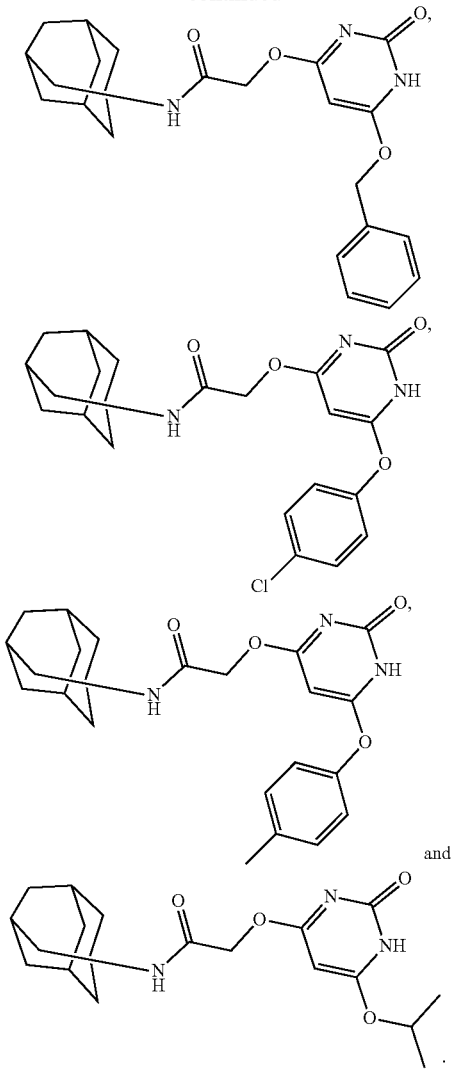

and

C. PHARMACEUTICAL COMPOSITIONS

In one aspect, disclosed are pharmaceutical compositions comprising a disclosed compound, or a pharmaceutically acceptable salt thereof and a pharmaceutically acceptable carrier.

In one aspect, disclosed are pharmaceutical compositions comprising a pharmaceutically acceptable carrier and a therapeutically effective amount of at least one compound having a structure represented by a formula:

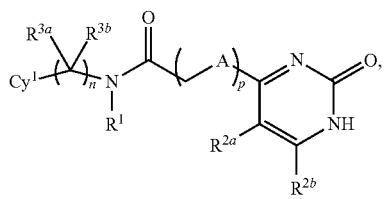

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —$OCy^2$, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when $Cy^1$ is C2-C9 heteroaryl, then either (i) p is 1 and A is O or (ii) n is 1 or 2 and each of $R^{3a}$ and $R^{3b}$ are not hydrogen; provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

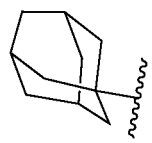

and p is 0, then n is 0 or 2, or a pharmaceutically acceptable salt thereof.

In one aspect, disclosed are pharmaceutical compositions comprising a pharmaceutically acceptable carrier and a therapeutically effective amount of at least one compound having a structure represented by a formula:

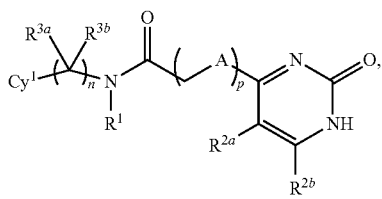

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C4 alkoxy, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of Art, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when $Cy^1$ is C2-C9 heteroaryl, then either (i) p is 1 and A is O or (ii) n is 1 or 2 and each of $R^{3a}$ and $R^{3b}$ are not hydrogen; provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

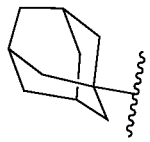

and p is 0, then n is 0 or 2, or a pharmaceutically acceptable salt thereof.

In one aspect, disclosed are pharmaceutical compositions comprising a pharmaceutically acceptable carrier and a therapeutically effective amount of at least one compound having a structure selected from:

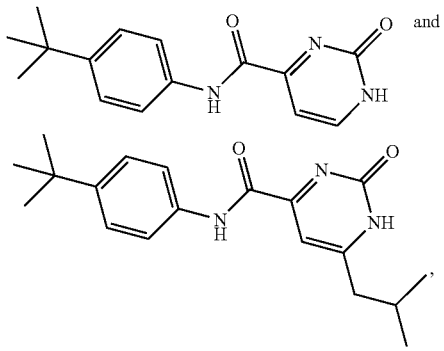

or a pharmaceutically acceptable salt thereof.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouthwashes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a viral infection such as, for example, chikungunya, Venezuelan equine encephalitis, Eastern equine encephalitis, and Western equine encephalitis.

It is understood that the disclosed compositions can be prepared from the disclosed compounds. It is also understood that the disclosed compositions can be employed in the disclosed methods of using.

D. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-VI, as described and exemplified below. The following examples are provided so that the invention might be more fully understood, are illustrative only, and should not be construed as limiting.

1. Route I

In one aspect, substituted 2-pyrimidone analogs can be prepared as shown below.

SCHEME 1A.

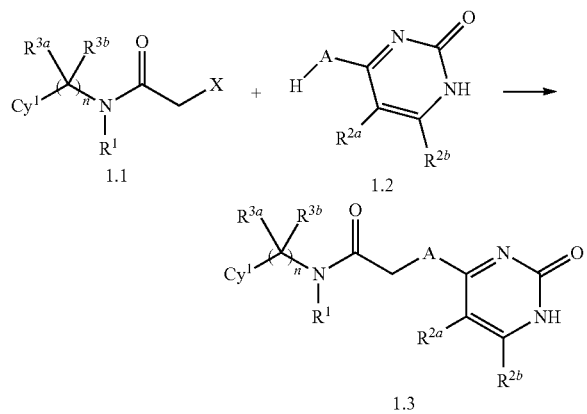

Compounds are represented in generic form, wherein X is a halogen and with substituents as noted in compound descriptions elsewhere herein. A more specific example is set forth below.

SCHEME 1B.

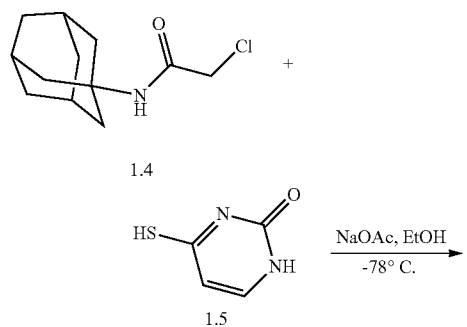

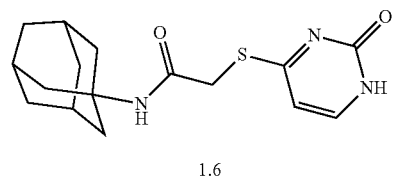

1.6

In one aspect, compounds of type 1.6 and similar compounds can be prepared according to reaction Scheme 1B above. Thus, compounds of type 1.6 can be prepared by reacting an appropriate nucleophilic compound, e.g., 1.5 as shown above, with an appropriate electrophilic compound, e.g., 1.4 as shown above. Appropriate nucleophilic compounds and appropriate electrophilic compounds are commercially available or prepared by methods known to one skilled in the art. The reaction is carried out in the presence of a suitable base, e.g., sodium acetate, in a suitable solvent, e.g., anhydrous ethanol, at a suitable temperature, e.g., 78° C. As can be appreciated by one skilled in the art, the above reaction provides an example of a generalized approach wherein compounds similar in structure to the specific reactants above (compounds similar to compounds of type 1.1 and 1.2) can be substituted in the reaction to provide substituted 2-pyrimidone analogs similar to Formula 1.3.

2. Route II

In another aspect, substituted 2-pyrimidone analogs can be prepared as shown below.

SCHEME 2A.

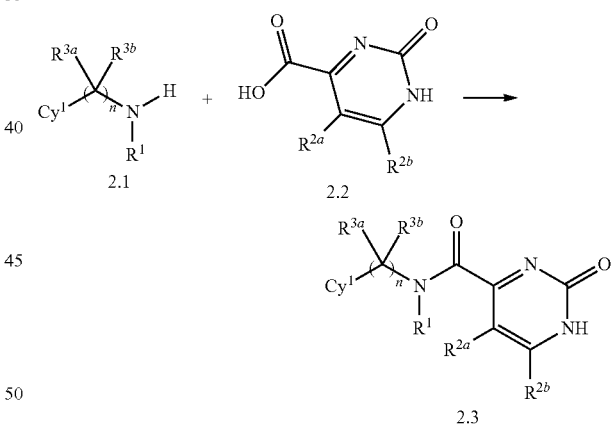

Compounds are represented in generic form with substituents as noted in compound descriptions elsewhere herein. A more specific example is set forth below.

SCHEME 2B.

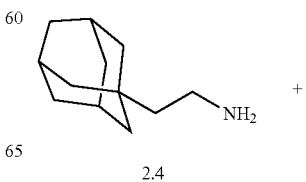

2.4

-continued

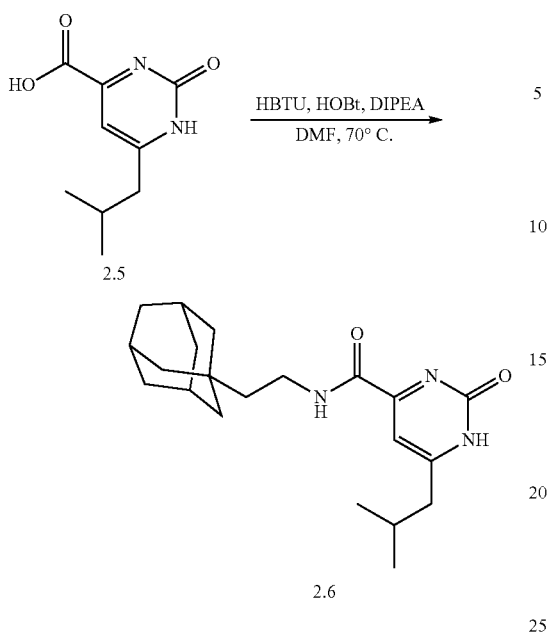

2.5

2.6

In one aspect, compounds of type 2.6 and similar compounds can be prepared according to reaction Scheme 2B above. Thus, compounds of type 2.6 can be prepared by a coupling reaction between an appropriate carboxylic acid, e.g., 2.5 as shown above, with an appropriate amine, e.g., 2.4 as shown above. Appropriate carboxylic acids and appropriate amines are commercially available or prepared by methods known to one skilled in the art. The coupling reaction is carried out in the presence of a suitable coupling agent, e.g., 2-(1H-benzotriazol-1-yl)-1,1,3,3-tetramethyluronium hexafluorophosphate (HBTU) as shown above, and a suitable additive, e.g., hydroxybenzotriazole (HOBt), in a suitable solvent, e.g., dimethylformamide (DMF), at a suitable temperature, e.g., 70° C. As can be appreciated by one skilled in the art, the above reaction provides an example of a generalized approach wherein compounds similar in structure to the specific reactants above (compounds similar to compounds of type 2.1 and 2.2) can be substituted in the reaction to provide substituted 2-pyrimidone analogs similar to Formula 2.3.

3. Route III

In a further aspect, substituted 2-pyrimidone analogs can be prepared as shown below.

SCHEME 3A.

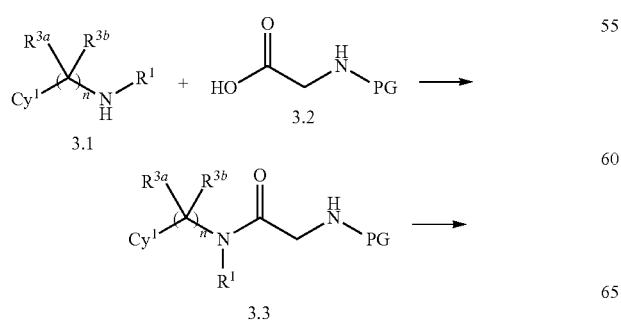

-continued

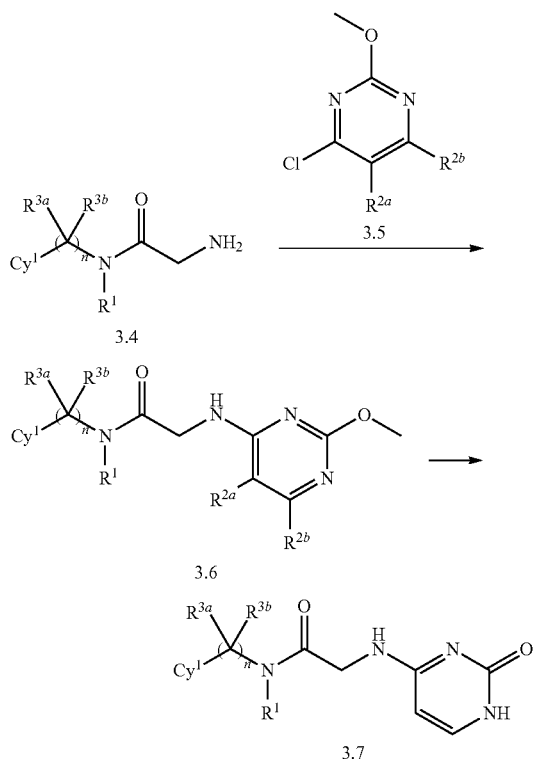

Compounds are represented in generic form, wherein PG is an amine protecting group and with other substituents as noted in compound descriptions elsewhere herein. A more specific example is set forth below.

SCHEME 3B.

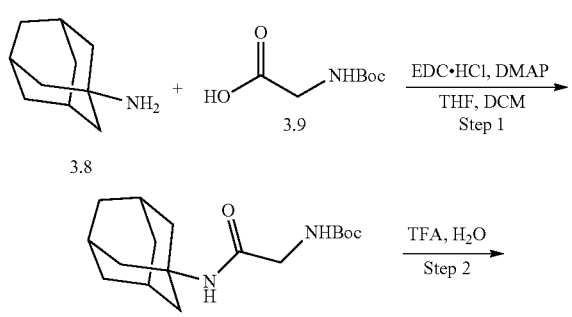

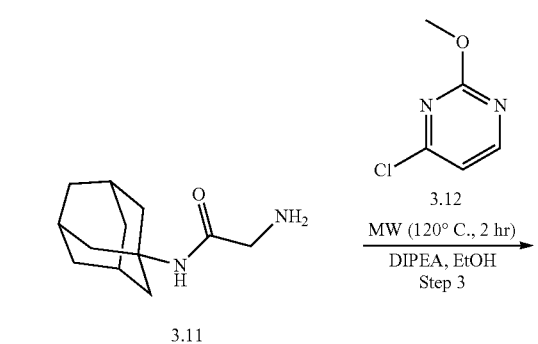

-continued

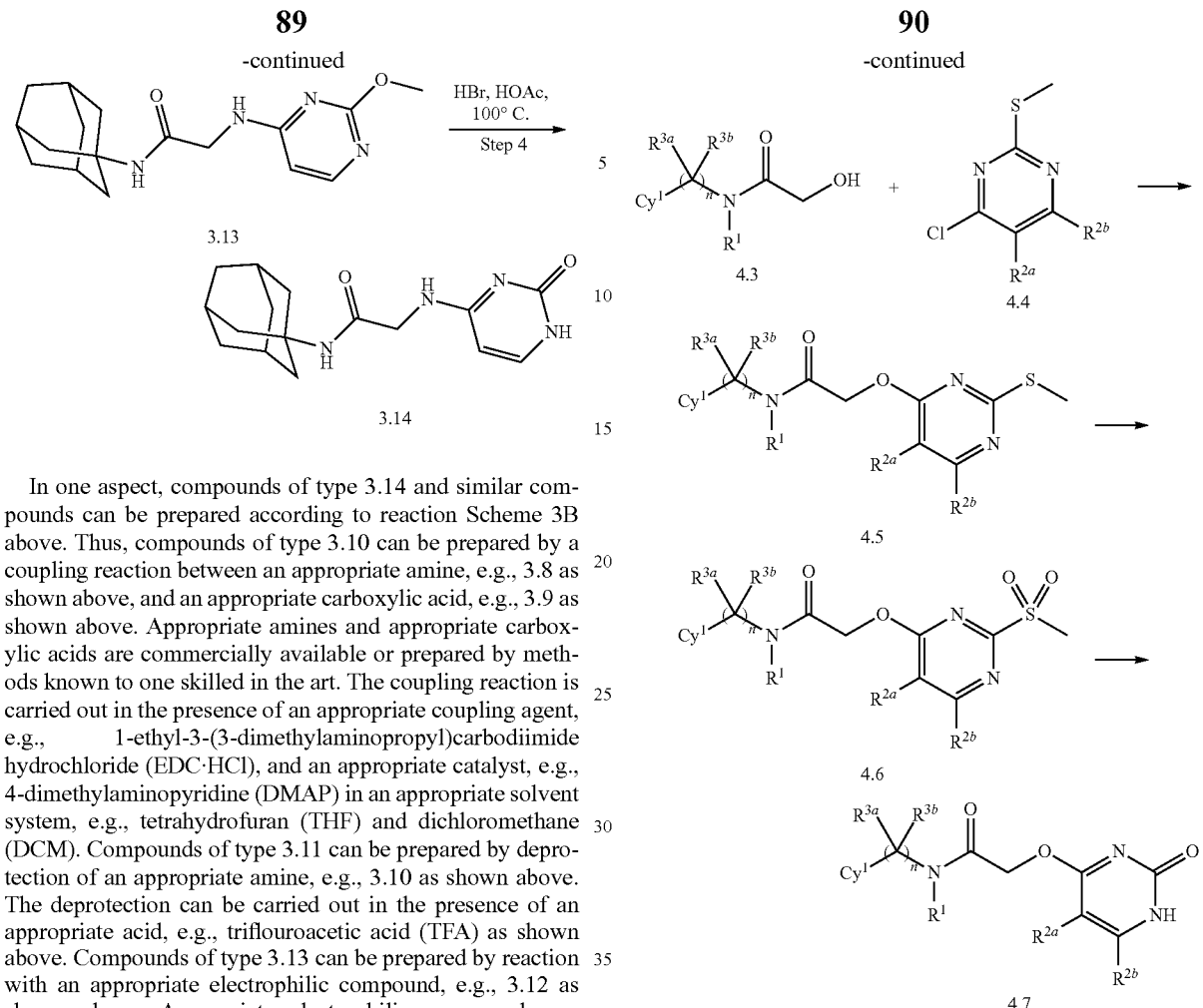

In one aspect, compounds of type 3.14 and similar compounds can be prepared according to reaction Scheme 3B above. Thus, compounds of type 3.10 can be prepared by a coupling reaction between an appropriate amine, e.g., 3.8 as shown above, and an appropriate carboxylic acid, e.g., 3.9 as shown above. Appropriate amines and appropriate carboxylic acids are commercially available or prepared by methods known to one skilled in the art. The coupling reaction is carried out in the presence of an appropriate coupling agent, e.g., 1-ethyl-3-(3-dimethylaminopropyl)carbodiimide hydrochloride (EDC·HCl), and an appropriate catalyst, e.g., 4-dimethylaminopyridine (DMAP) in an appropriate solvent system, e.g., tetrahydrofuran (THF) and dichloromethane (DCM). Compounds of type 3.11 can be prepared by deprotection of an appropriate amine, e.g., 3.10 as shown above. The deprotection can be carried out in the presence of an appropriate acid, e.g., triflouroacetic acid (TFA) as shown above. Compounds of type 3.13 can be prepared by reaction with an appropriate electrophilic compound, e.g., 3.12 as shown above. Appropriate electrophilic compounds are commercially available or prepared by methods known to one skilled in the art. The reaction is carried out in the presence of a suitable base, e.g., N,N-diisopropylethylamine (DIPEA), in an appropriate solvent, e.g., ethanol, at a suitable temperature, e.g., 120° C. in a microwave reactor, for a suitable time, e.g., two hours. Compounds of type 3.14 can be prepared by subjecting an appropriate primidine, e.g., 3.13, to an appropriate acid, e.g., hydrobromic acid, in an appropriate protic solvent, e.g., acetic acid, at a suitable temperature, e.g., 100° C. As can be appreciated by one skilled in the art, the above reaction provides an example of a generalized approach wherein compounds similar in structure to the specific reactants above (compounds similar to compounds of type 3.1, 3.2, 3.3, 3.4, 3.5, and 3.6) can be substituted in the reaction to provide substituted 2-pyrimidone analogs similar to Formula 3.7.

4. Route IV

In another aspect, substituted 2-pyrimidone analogs can be prepared as shown below.

SCHEME 4A.

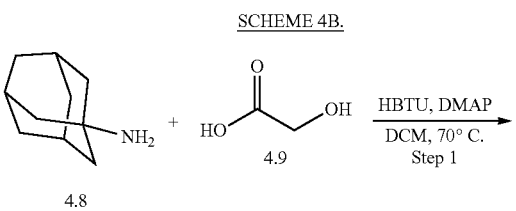

Compounds are represented in generic form with substituents as noted in compound descriptions elsewhere herein. A more specific example is set forth.

SCHEME 4B.

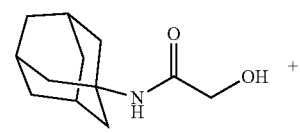

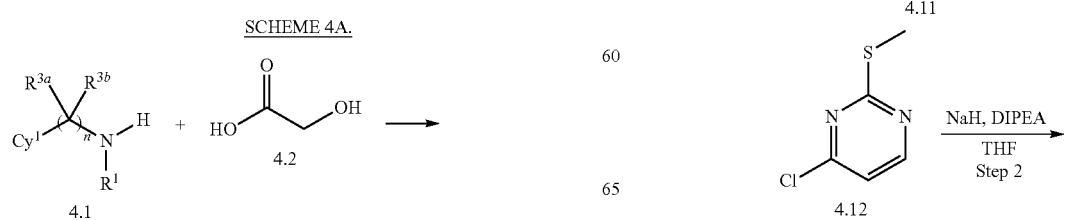

-continued

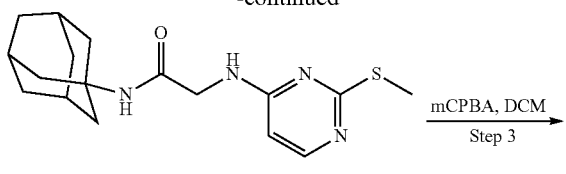

4.13

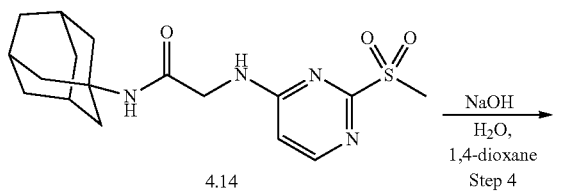

4.14

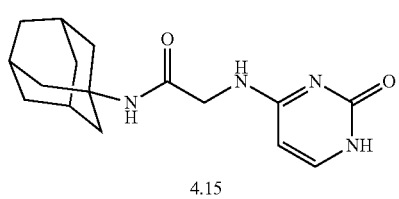

4.15

In one aspect, compounds of type 4.15 and similar compounds can be prepared according to reaction Scheme 4B above. Thus, compounds of type 4.11 and similar compounds can be prepared by a coupling reaction between an appropriate carboxylic acid, e.g., 4.9 as shown above, with an appropriate amine, e.g., 4.8 as shown above. Appropriate carboxylic acids and appropriate amines are commercially available or prepared by methods known to one skilled in the art. The coupling reaction can be carried out in the presence of a suitable coupling reagent, e.g., 2-(1H-benzotriazol-1-yl)-1,1,3,3-tetramethyluronium hexafluorophosphate (HBTU) as shown above, and a suitable base, e.g., N,N-diisopropylethylamine (DIPEA), in the presence of a suitable solvent, e.g., DMF, at a suitable temperature, e.g., 70° C. Compounds of type 4.13 can be prepared by reaction with an appropriate electrophilic compound, e.g., 4.12 as shown above. Suitable electrophilic compounds are commercially available or prepared by methods known to one skilled in the art. The reaction is carried out in the presence of an appropriate base, e.g., N,N-diisopropylethylamine (DIPEA), and an appropriate hydride source, e.g., sodium hydride, in an appropriate solvent, e.g., THF. Compounds of type 4.14 can be prepared by oxidation of a compound of type 4.13. The oxidation is carried out in the presence of a suitable oxidant, e.g., meta-chloroperoxybenzoic acid as shown above, in a suitable solvent, e.g., methylene chloride. Compounds of type 4.15 can be prepared by subjecting an appropriate pyrimidine, e.g., 4.14, to an appropriate base, e.g., sodium hydroxide, in a suitable solvent, e.g., anhydrous 1,4-dioxane. As can be appreciated by one skilled in the art, the above reaction provides an example of a generalized approach wherein compounds similar in structure to the specific reactants above (compounds similar to compounds of type 4.1, 4.2, 4.3, 4.4, 4.5, and 4.6) can be substituted in the reaction to provide substituted 2-pyrimidone analogs similar to Formula 4.7.

5. Route V

In a further aspect, substituted 2-pyrimidone analogs can be prepared as shown below.

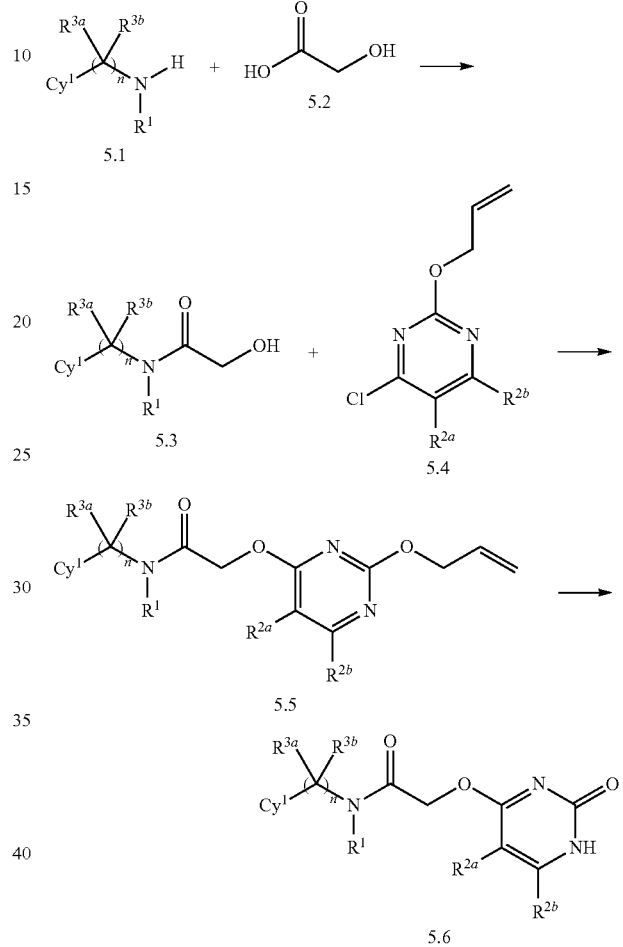

Compounds are represented in generic form with substituents as noted in compound descriptions elsewhere herein. A more specific example is set forth below in Scheme 5B.

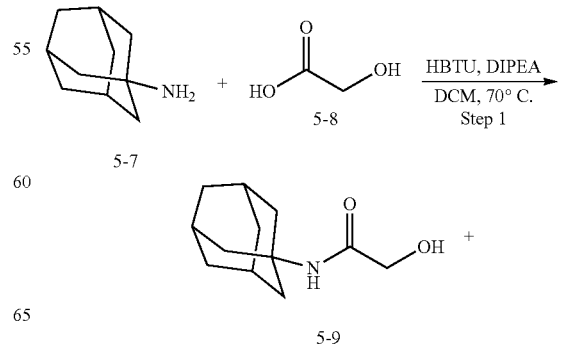

93

-continued

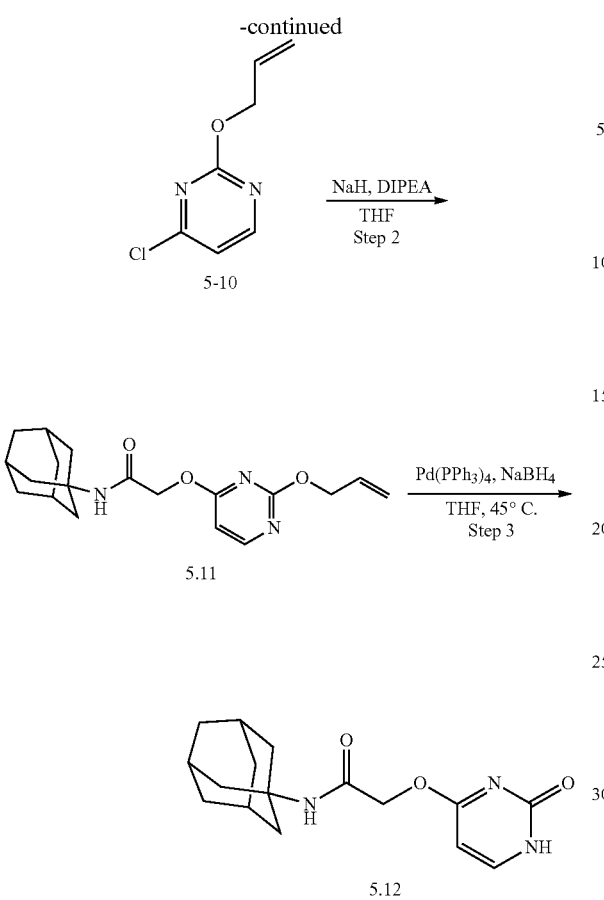

5-10

5.11

5.12

In one aspect, compounds of type 5.12 and similar compounds can be prepared according to reaction Scheme 5B above. Thus, compounds of type 5.9 and similar compounds can be prepared by a coupling reaction between an appropriate carboxylic acid, e.g., 5.8 as shown above, with an appropriate amine, e.g., 5.7 as shown above. Appropriate carboxylic acids and appropriate amines are commercially available or prepared by methods known to one skilled in the art. The coupling reaction is carried out in the presence of a suitable coupling reagent, e.g., HBTU as shown above, and a suitable base, e.g., DIPEA, in a suitable solvent, e.g., DMF, at a suitable temperature, e.g., 70° C. Compounds of type 5.11 can be prepared by reaction with an appropriate electrophilic compound, e.g., 5.10 as shown above. Suitable electrophilic compounds are commercially available or prepared by methods known to one skilled in the art. The reaction is carried out in the presence of an appropriate base, e.g., DIPEA, and an appropriate hydride source, e.g., sodium hydride, in an appropriate solvent, e.g., THF. Compounds of type 5.12 can be prepared by subjecting an appropriate pyrimidine, e.g., 5.11 as shown above, to an appropriate catalyst, e.g., tetrakis(triphenylphosphine) palladium, and an appropriate salt, e.g., sodium borohydride, in an appropriate solvent, e.g., THF, at an appropriate temperature, e.g., 0° C. As can be appreciated by one skilled in the art, the above reaction provides an example of a generalized approach wherein compounds similar in structure to the specific reactants above (compounds similar to compounds of type 5.1, 5.2, 5.3, 5.4, and 5.5) can be substituted in the reaction to provide substituted 2-pyrimidone analogs similar to Formula 5.6.

94

6. Route VI

In another aspect, substituted 2-pyrimidone analogs can be prepared as shown below.

SCHEME 6A.

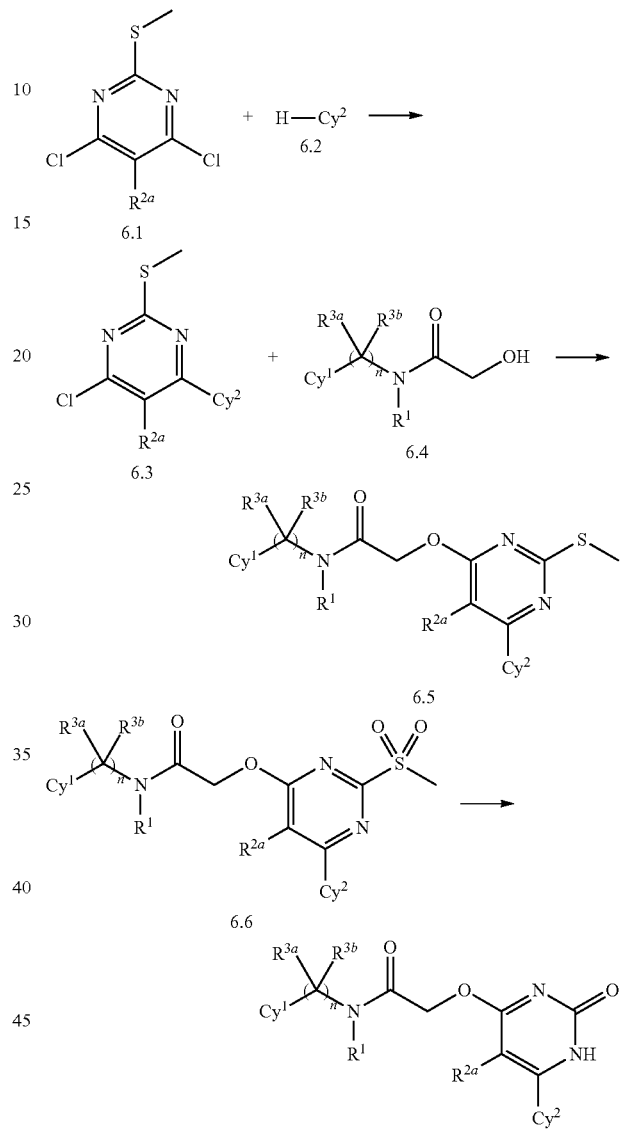

Compounds are represented in generic form with substituents as noted in compound descriptions elsewhere herein. A more specific example is set forth below.

SCHEME 6B.

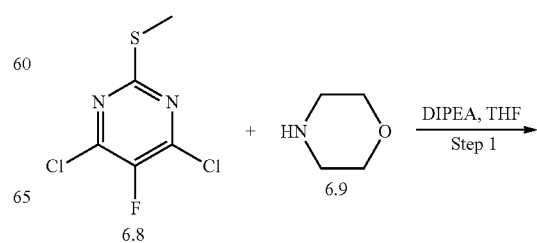

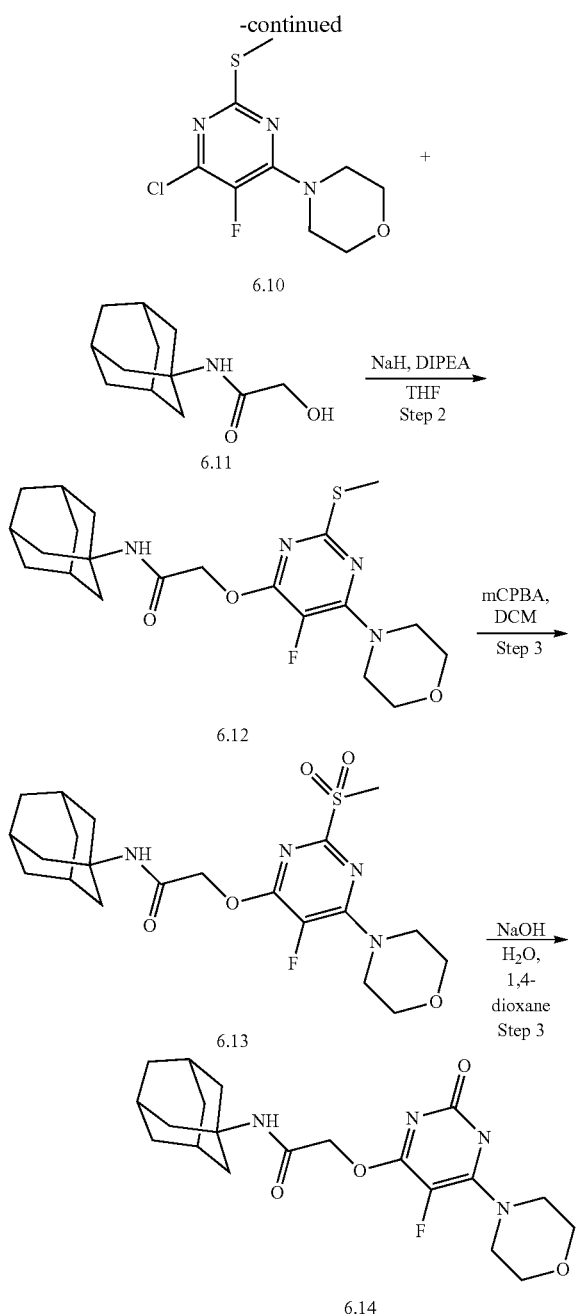

prepared by oxidation of an appropriate sulfane, e.g., 6.12 as shown above. The oxidation is carried out in the presence of an appropriate oxidizing agent, e.g., meta-chloroperoxybenzoic acid, in an appropriate solvent, e.g., DCM. Compounds of type 6.14 can be prepared by subjecting an appropriate pyrimidine, e.g., 6.13 as shown above, to a base, e.g., sodium hydroxide, in a suitable solvent, e.g., 1,4-dioxane. As can be appreciated by one skilled in the art, the above reaction provides an example of a generalized approach wherein compounds similar in structure to the specific reactants above (compounds similar to compounds of type 6.1, 6.2, 6.3, 6.4, 6.5, and 6.6) can be substituted in the reaction to provide substituted 2-pyrimidone analogs similar to Formula 6.7.

E. METHODS OF USING THE COMPOUNDS

The compounds and pharmaceutical compositions of the invention are useful in treating or controlling disorders associated with a viral infection, in particular, those due to an Alphavirus such as, for example, CHIKV, WEEV, EEEV, and VEEV. To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a viral infection, such as CHIKV, WEEV, EEEV, and VEEV.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a viral infection, such as CHIKV, WEEV, EEEV, and VEEV.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The In one aspect, compounds of type 6.14 and similar compounds can be prepared according to reaction Scheme 6B above. Thus, compounds of type 6.10 and similar compounds can be prepared by reacting an appropriate halide, e.g., 6.8, and an appropriate heterocycle, e.g., 6.9 as shown above. Appropriate halides and appropriate heterocycles are commercially available or prepared by methods known to one skilled in the art. The reaction is carried out in the presence of an appropriate base, e.g., DIPEA, in an appropriate solvent, e.g., THF. Compounds of type 6.12 can be prepared by reacting an appropriate electrophilic agent, e.g., 6.10 as shown above, and an appropriate nucleophilic agent, e.g., 6.11 as shown above. The reaction is carried out in the presence of an appropriate base, e.g., DIPEA, and an appropriate hydride source, e.g., sodium hydride, in an appropriate solvent, e.g., THF. Compounds of type 6.13 can be dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with a viral infection, in particular, CHIKV, WEEV, EEEV, and VEEV. Thus, provided is a method comprising administering a therapeutically effective amount of a disclosed compound to a subject. In a further aspect, the method can be a method for treating a viral infection.

a. Treating a Viral Infection

In one aspect, disclosed are methods of treating a viral infection in a subject having the viral infection, the method comprising the step of administering to the subject a therapeutically effective amount of at least one disclosed compound, or a pharmaceutically acceptable salt thereof.

In one aspect, disclosed are methods for the treatment of a viral infection in a subject having the viral infection, the method comprising the step of administering to the subject a therapeutically effective amount of at least one compound having a structure represented by a formula:

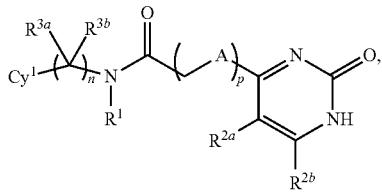

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —O$Cy^2$, —O$Ar^1$, —O(C1-C4 alkyl)O$R^{10}$, —O(C1-C4 alkyl)$Ar^1$, —CO$_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when $Cy^1$ is C2-C9 heteroaryl, then either (i) p is 1 and A is O or (ii) n is 1 or 2 and each of $R^{3a}$ and $R^{3b}$ are not hydrogen; provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

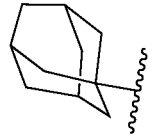 [SMILES: *C12CC3CC(CC(C3)C1)C2]

and p is 0, then n is 0 or 2, or a pharmaceutically acceptable salt thereof, wherein the viral infection is due to an Alphavirus, thereby treating the viral infection.

In one aspect, disclosed are methods for the treatment of a viral infection in a subject having the viral infection, the method comprising the step of administering to the subject a therapeutically effective amount of at least one compound having a structure represented by a formula:

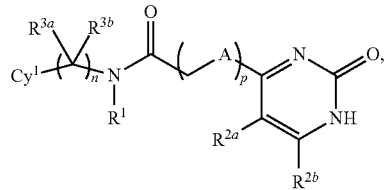

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C4 alkoxy, —O$Ar^1$, —O(C1-C4 alkyl)O$R^{10}$, —O(C1-C4 alkyl)$Ar^1$, —CO$_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ and R$^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of R$^{3a}$ and R$^{3b}$, when present, is independently selected from hydrogen, halogen, C1-C4 alkyl, and C1-C4 haloalkyl; or wherein R$^{3a}$ and R$^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when p is 1, A is S, and Cy$^1$ is C6 aryl, then Cy$^1$ is not substituted with a halogen group, or a pharmaceutically acceptable salt thereof, wherein the viral infection is due to an Alphavirus, thereby treating the viral infection.

Examples of viral infections include, but are not limited to, Chikungunya virus (CHIKV), Semliki Firest virus, Ross River virus, Venezuelan equine encephalitis (VEEV), Eastern equine encephalitis (EEEV), and Western equine encephalitis (WEEV). In a further aspect, the Alphavirus is selected from CHIKV and VEEV.

In a further aspect, the subject has been diagnosed with a need for treatment of the viral infection prior to the administering step.

In a further aspect, the subject is a mammal. In a still further aspect, the mammal is a human.

In a further aspect, the method further comprises the step of identifying a subject in need of treatment of the viral infection.

In a further aspect, the effective amount is a therapeutically effective amount. In a still further aspect, the effective amount is a prophylactically effective amount.

In a further aspect, the disorder is associated with a viral infection. In a still further aspect, the viral infection is due to an Alphavirus. In an even further aspect, the viral infection is selected from CHIKV, VEEV, WEEV, and EEEV.

In a further aspect, the method further comprises the step of administering a therapeutically effective amount of at least one antiviral agent. In a still further aspect, the at least one agent is selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods of Inhibiting a Viral Infection in a Mammal

In one aspect, disclosed are methods of inhibiting a viral infection in a mammal, the method comprising the step of administering to the mammal a therapeutically effective amount of at least one disclosed compound, or a pharmaceutically acceptable salt thereof.

Thus, in one aspect, disclosed are methods of inhibiting a viral infection in a mammal, the method comprising the step of administering to the mammal a therapeutically effective amount of at least one compound having a structure represented by a formula:

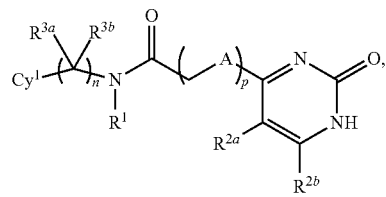

wherein n is 0, 1, or 2; wherein p is 0 or 1; wherein A is O, S, or NH; wherein R$^1$ is selected from hydrogen and C1-C4 alkyl; wherein each of R$^{2a}$ and R$^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —OCy$^2$, —OAr$^1$, —O(C1-C4 alkyl)OR$^{10}$, —O(C1-C4 alkyl)Ar$^1$, —CO$_2$R$^{10}$, and Cy$^2$; wherein each occurrence of R$^{10}$, when present, is independently selected from hydrogen and C1-C4 alkyl; wherein each occurrence of Ar$^1$, when present, is independently selected from C2-C5 heteroaryl and C6-C12 aryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of Cy$^2$, when present, is independently selected from C3-C6 cycloalkyl, C3-C6 heterocycloalkyl, and phenyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when $Cy^1$ is C2-C9 heteroaryl, then either (i) p is 1 and A is O or (ii) n is 1 or 2 and each of $R^{3a}$ and $R^{3b}$ are not hydrogen; provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

[adamantyl structure]

and p is 0, then n is 0 or 2, or a pharmaceutically acceptable salt thereof, wherein the viral infection is due to an Alphavirus, thereby inhibiting the viral infection in the mammal.

In one aspect, disclosed are methods of inhibiting a viral infection in a mammal, the method comprising the step of administering to the mammal a therapeutically effective amount of at least one compound having a structure represented by a formula:

[chemical structure with $R^{3a}$, $R^{3b}$, $Cy^1$, $R^1$, A, $R^{2a}$, $R^{2b}$]

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C4 alkoxy, —OAr$^1$, —O(C1-C4 alkyl)OR$^{10}$, —O(C1-C4 alkyl)Ar$^1$, —CO$_2$R$^{10}$, and Cy$^2$; wherein each occurrence of $R^{10}$, when present, is independently selected from hydrogen and C1-C4 alkyl; wherein each occurrence of Ar$^1$, when present, is independently selected from C2-C5 heteroaryl and C6-C12 aryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of Cy$^2$, when present, is independently selected from C3-C6 cycloalkyl, C3-C6 heterocycloalkyl, and phenyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when p is 1, A is S, and $Cy^1$ is C6 aryl, then $Cy^1$ is not substituted with a halogen group, or a pharmaceutically acceptable salt thereof, wherein the viral infection is due to an Alphavirus, thereby inhibiting the viral infection in the mammal.

In a further aspect, the compound exhibits inhibition of a viral infection. In a still further aspect, the compound exhibits a decrease in a viral infection. In yet a further aspect, the viral infection is CHIKV or VEEV.

In a further aspect, the compound exhibits inhibition of Alphavirus activity with an EC$_{90}$ of less than about 30 μM. In a still further aspect, the compound exhibits inhibition of Alphavirus activity with an EC$_{90}$ of less than about 25 μM. In yet a further aspect, the compound exhibits inhibition of Alphavirus activity with an EC$_{90}$ of less than about 20 μM. In an even further aspect, the compound exhibits inhibition of Alphavirus activity with an EC$_{90}$ of less than about 15 μM. In a still further aspect, the compound exhibits inhibition of Alphavirus activity with an EC$_{90}$ of less than about 10 μM. In yet a further aspect, the compound exhibits inhibition of Alphavirus activity with an EC$_{90}$ of less than about 5 μM. In an even further aspect, the compound exhibits inhibition of Alphavirus activity with an EC$_{90}$ of less than about 1 μM. In a still further aspect, the compound exhibits inhibition of Alphavirus activity with an $EC_{90}$ of less than about 0.5 μM.

In a further aspect, the subject is a mammal. In a still further aspect, the subject is a human.

In a further aspect, the subject has been diagnosed with a need for treatment of the viral infection prior to the administering step. In a still further aspect, the method further comprises the step of identifying a subject in need of treatment of the viral infection.

3. Methods of Inhibiting a Viral Infection in at Least One Cell

In one aspect, disclosed are methods for inhibiting a viral infection in at least one cell, the method comprising the step of contacting the at least one cell with an effective amount of at least one disclosed compound, or a pharmaceutically acceptable salt thereof.

Thus, in one aspect, disclosed are methods for inhibiting a viral infection in at least one cell, the method comprising the step of contacting the at least one cell with an effective amount of at least one compound having a structure represented by a formula:

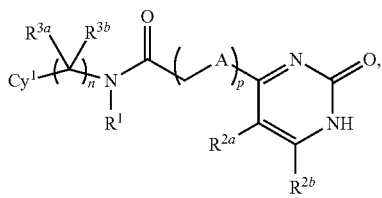

wherein n is 0, 1, or 2; wherein p is or; wherein A is O, S or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —$OCy^2$, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when $Cy^1$ is C2-C9 heteroaryl, then either (i) p is 1 and A is O or (ii) n is 1 or 2 and each of $R^{3a}$ and $R^{3b}$ are not hydrogen; provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

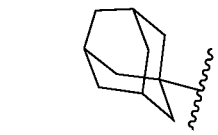 [SMILES: *C12CC3CC(CC(C3)C1)C2]

and p is 0, then n is 0 or 2, or a pharmaceutically acceptable salt thereof, wherein the viral infection is due to an Alphavirus, thereby inhibiting the viral infection in the at least one cell.

In one aspect, disclosed are methods for inhibiting a viral infection in at least one cell, the method comprising the step of contacting the at least one cell with an effective amount of at least one compound having a structure represented by a formula:

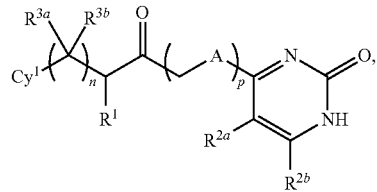

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C4 alkoxy, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ and R$^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of R$^{3a}$ and R$^{3b}$, when present, is independently selected from hydrogen, halogen, C1-C4 alkyl, and C1-C4 haloalkyl; or wherein R$^{3a}$ and R$^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when p is 1, A is S, and Cy$^1$ is C6 aryl, then Cy$^1$ is not substituted with a halogen group, or a pharmaceutically acceptable salt thereof, wherein the viral infection is due to an Alphavirus, thereby inhibiting the viral infection in the at least one cell.

In a further aspect, the cell is mammalian. In a still further aspect, the cell is human. In yet a further aspect, the cell has been isolated from a mammal prior to the contacting step.

In a further aspect, contacting is via administration to a mammal.

4. Use of Compounds

In one aspect, the invention relates to the use of a disclosed compound or a product of a disclosed method. In a further aspect, a use relates to the manufacture of a medicament for the treatment of a viral infection in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a viral infection in a subject. Also disclosed is the use of a compound for antagonism or inhibition of a viral infection. In one aspect, the use is characterized in that the subject is a human. In one aspect, the use is characterized in that the viral infection is due to an Alphavirus.

In a further aspect, the use relates to the manufacture of a medicament for the treatment of a viral infection in a subject.

In a further aspect, the use relates to antagonism or inhibition of a viral infection in a subject. In a further aspect, the use relates to modulating viral activity in a subject. In a still further aspect, the use relates to modulating viral activity in a cell. In yet a further aspect, the subject is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a viral infection in a mammal. In a further aspect, the viral infection is selected from Chikungunya virus (CHIKV), Ross River virus, Venezuelan equine encephalitis (VEEV), Eastern equine encephalitis (EEEV), and Western equine encephalitis (WEEV).

5. Manufacture of a Medicament

In one aspect, the invention relates to a method for the manufacture of a medicament for treating a viral infection in a subject having the viral infection, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of a viral infection. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, disclosed are kits comprising at least one disclosed compound and one or more of: (a) at least one antiviral agent; (b) instructions for administering the compound in connection with treating a viral infection; (c) instructions for administering the compound in connection with reducing the risk of viral infection; and (d) instructions for treating a viral infection.

In one aspect, disclosed are kits comprising a compound having a structure represented by a formula:

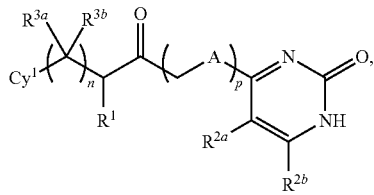

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —$OCy^2$, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl; or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^1$ is selected from C2-C9 heteroaryl, C6 aryl, and adamantyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when $Cy^1$ is C2-C9 heteroaryl, then either (i) p is 1 and A is O or (ii) n is 1 or 2 and each of $R^{3a}$ and $R^{3b}$ are not hydrogen; provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

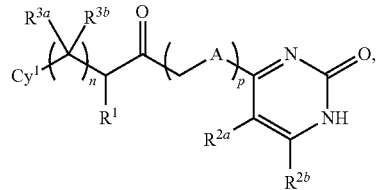

and p is 0, then n is 0 or 2, or a pharmaceutically acceptable salt thereof, and one or more of: (a) at least one antiviral agent; (b) instructions for administering the compound in connection with treating a viral infection; (c) instructions for administering the compound in connection with reducing the risk of viral infection; or (d) instructions for treating a viral infection.

In one aspect, disclosed are kits comprising a compound having a structure represented by a formula:

wherein n is 0, 1, or 2; wherein p is 0 or 1; wherein A is O, S, or NH; wherein $R^1$ is selected from hydrogen and C1-C4 alkyl; wherein each of $R^{2a}$ and $R^{2b}$ is independently selected from hydrogen, halogen, C1-C6 alkyl, C1-C4 haloalkyl, C1-C4 alkoxy, —$OAr^1$, —O(C1-C4 alkyl)$OR^{10}$, —O(C1-C4 alkyl)$Ar^1$, —$CO_2R^{10}$, and $Cy^2$; wherein each occurrence of $R^{10}$, when present, is independently selected from hydrogen and C1-C4 alkyl; wherein each occurrence of $Ar^1$, when present, is independently selected from C2-C5 heteroaryl and C6-C12 aryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of R$^{3a}$ and R$^{3b}$, when present, is independently selected from hydrogen, halogen, C1-C4 alkyl, and C1-C4 haloalkyl; or wherein R$^{3a}$ and R$^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl; provided that when p is 1, A is S, and Cy$^1$ is C6 aryl, then Cy$^1$ is not substituted with a halogen group, or a pharmaceutically acceptable salt thereof, and one or more of: (a) at least one antiviral agent; (b) instructions for administering the compound in connection with treating a viral infection; (c) instructions for administering the compound in connection with reducing the risk of viral infection; or (d) instructions for treating a viral infection.

In a further aspect, the viral infection is selected from CHIKV, VEEV, WEEV, and EEEV. In yet a further aspect, the viral infection is CHIKV or VEEV.

In a still further aspect, the antiviral agent is selected from selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are co-formulated. In a further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals
a. General Experimental Methods

The reactions were performed under a dry argon atmosphere and reaction temperatures were measured externally. Anhydrous solvents were purchased from Aldrich and used as such in reactions. Microwave (MW) reactions were performed in Biotage Initiator+. The reactions were monitored by thin-layer chromatography (TLC) on pre-coated silica gel (60F$_{254}$) glass plates and visualized using UV light (254 nm). Purification of compounds was performed on a Teledyne Isco Combiflash Rf 200 with UV detector. Universal RediSep solid sample loading pre-packed cartridges (12 or 25 g Silica) were used to absorb crude product and purified on 24 or 40 g silica RediSep Rf Gold Silica columns using appropriate solvent gradients. Pure samples were dried under high vacuum at 25-60° C. before analyses. The HR-mass spectral data were obtained on an Agilent LC- MSTOF by electrospray ionization (ESI). $^1$H NMR spectra were recorded at 400 MHz on Agilent/Varian MR-400 spectrometer in CDCl$_3$, CD$_3$OD or DMSO-d$_6$ as solvents. The chemical shifts (δ) are in ppm downfield from standard tetramethylsilane (TMS) and coupling constants (J) are reported in Hertz (Hz). Purity of final compounds was checked by HPLC using Waters HPLC equipped with a 3100 Mass Detector using Sunfire C18 column (5 μm, 4.6×150 mm) and Acetonitrile-H$_2$O (both containing 0.1% formic acid) 10-90% as solvent in 22 min.

b. Synthetic Procedure I

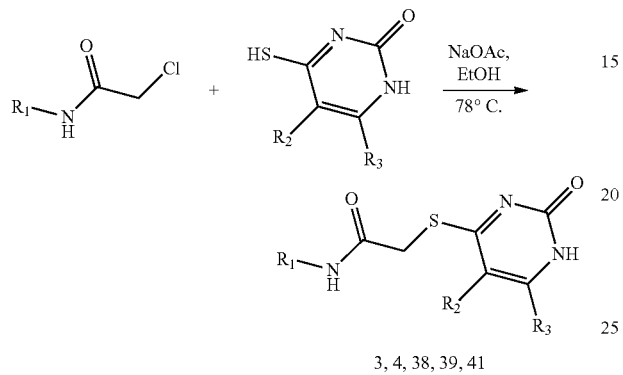

3, 4, 38, 39, 41

Corresponding chloroacetamide (1 mmol) was added to a solution of corresponding sulfanyl-pyrimidine-2-one (1 mmol) and sodium acetate (3 mmol) in anhydrous EtOH (9 mL). The reaction mixture was then stirred at 78° C. for 18 hrs. After cooling to room temperature, the solvent was evaporated, residue treated with H$_2$O (20 mL) and extracted with EtOAc (3×20 mL). The organic layer was collected, dried over anhydrous Na$_2$SO$_4$, filtered and evaporated to dryness under reduced pressure to give a residue, which was purified on pre-packed Silica gel column to yield the product.

i. N-(Adamantan-1-Yl)-2-((2-Oxo-1,2-Dihydropyrimidin-4-Yl)Thio)Acetamide (3)

Purification on pre-packed Silica gel column on ISCO using 0-10% MeOH in DCM (20 min). Yield: 75 mg (53%). $^1$H NMR (CDCl$_3$): δ 7.50 (d, J=6.7 Hz, 1H), 6.90 (s, 1H), 6.35 (d, J=6.7 Hz, 1H), 3.73 (s, 2H), 2.08-2.01 (m, 3H), 1.99-1.95 (m, 6H), 1.66-1.64 (m, 6H). HR-ESIMS: m/z 320.1433 [M+H]$^+$ calcd. for C$_{16}$H$_{22}$N$_3$O$_2$S, found 320.1426. HPLC purity: 98% (Retention Time=10.8 min).

ii. N-(Adamantan-2-Yl)-2-((2-Oxo-1,2-Dihydropyrimidin-4-Yl)Thio)Acetamide (4)

Purification on pre-packed Silica gel column on ISCO using 0-10% MeOH in DCM (20 min). Yield: 30 mg (43%). $^1$H NMR (CDCl$_3$): δ 7.48 (d, J=6.8 Hz, 1H), 6.90 (s, 1H), 6.34 (d, J=6.8 Hz, 1H), 3.72 (s, 2H), 2.18-1.81 (m, 9H), 1.78-1.54 (m, 6H). HR-ESIMS: m/z 320.1433 [M+H]$^+$ calcd. for C$_{16}$H$_{22}$N$_3$O$_2$S, found 320.1429. HPLC purity: 97% (Retention Time=5.7 min).

iii. 4-((2-((Adamantan-1-Yl)Amino)-2-Oxoethyl)Thio)-6-Methyl-2-Oxo-1,2-Dihydropyrimidine-5-Carboxylic Acid (38)

Purification on pre-packed Silica gel column on ISCO using 0-10% MeOH in DCM (20 min). Yield: 23 mg (28%). $^1$H NMR (DMSO-d$_6$): δ 11.95 (s, 1H), 7.63 (s, 1H), 3.63 (s, 2H), 2.41 (s, 3H), 1.99-1.96 (m, 3H), 1.92-1.84 (m, 6H), 1.63-1.55 (m, 6H). ESIMS: m/z 378.1 [M+H]$^+$. HPLC purity: 96% (Retention Time=9.7 min).

iv. Butyl 6-((2-((-Adamantan-1-Yl)Amino)-2-Oxoethyl)Thio)-2-Oxo-2,3-Dihydropyrimidine-4-Carboxylate (39)

Purification on pre-packed Silica gel column on ISCO using 0-10% MeOH in DCM (20 min). Yield: 45 mg (49%). $^1$H NMR (CDCl$_3$): δ 6.81 (s, 1H), 4.45 (q, J=7.2 Hz, 2H), 3.73 (s, 2H), 2.09-2.01 (m, 3H), 1.98-1.94 (m, 9H), 1.69-1.61 (m, 6H), 1.60-1.50 (m, 2H), 1.41 (t, J=7.1 Hz, 3H). HPLC purity: 100% (Retention Time=12.3 min).

v. N-((Adamantan-1-Yl)Methyl)-2-((2-Oxo-1,2-Dihydropyrimidin-4-Yl)Thio)Acetamide (41)

Purification on pre-packed Silica gel column on ISCO using 0-10% MeOH in DCM (20 min). Yield: 77 mg (56%). $^1$H NMR (CDCl$_3$): δ 12.23 (s, 1H), 7.48 (d, J=6.7 Hz, 1H), 7.11 (s, 1H), 6.36 (d, J=6.7 Hz, 1H), 3.83 (s, 2H), 2.93 (d, J=6.1 Hz, 2H), 1.92-1.89 (m, 2H), 1.68-1.65 (m, 2H), 1.64-1.62 (m, 3H), 1.57-1.53 (m, 3H), 1.45-1.43 (m, 5H). HR-ESIMS: m/z 334.15837 [M+H]$^+$ calcd. for C$_{17}$H$_{24}$N$_3$O$_2$S, found 334.15825. HPLC purity: 100% (Retention Time=10.1 min).

c. Synthetic Procedure II

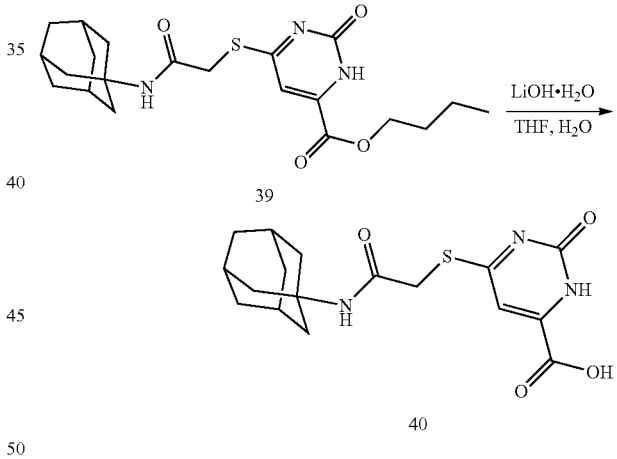

Synthesis of 6-((2-((adamantan-1-yl)amino)-2-oxoethyl)thio)-2-oxo-2,3-dihydropyrimidine-4-carboxylic acid (40): Lithium hydroxide monohydrate (0.008 g, 0.19 mmol) was added to a solution of butyl 6-((2-(((3s,5s,7s)-adamantan-1-yl)amino)-2-oxoethyl)thio)-2-oxo-2,3-dihydropyrimidine-4-carboxylate (39) (0.04 g, 0.10 mmol) in THF (1 mL) and H$_2$O (1 mL). The reaction mixture was then stirred at rt for 24 hrs. The solution was concentrated to dryness under reduced pressure, and the residue was neutralized with HCl (1N). A precipitate formed immediately. The solid was collected by filtration, and washed with H$_2$O to yield the product. Yield: 12 mg (35%). $^1$H NMR (DMSO-d$_6$) δ 7.73 (s, 1H), 6.61 (s, 1H), 3.78 (s, 2H), 2.01-1.93 (m, 3H), 1.92-1.84 (m, 6H), 1.59-1.57 (m, 6H). HR-ESIMS: m/z 364.13255 [M+H]$^+$ calcd. for C$_{17}$H$_{22}$N$_3$O$_4$S, found 364.13222. HPLC purity: 95% (Retention Time=9.7 min).

d. Synthetic Procedure III

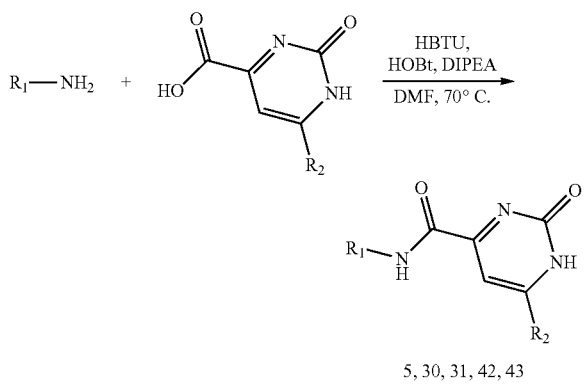

5, 30, 31, 42, 43

HBTU (1.5 mmol), HOBt (0.2 mmol) and DIPEA (3 mmol) were added to a solution of corresponding carboxylic acid (1 mmol) in anhydrous DMF (16 mL). After stirring for 10 min at room temperature, corresponding amine (1 mmol) was added. The reaction mixture was then stirred at 70° C. for 18 hrs. After cooling to room temperature, the reaction mixture was treated with $H_2O$ (100 mL) and extracted with DCM (3×50 mL). The organic layer was collected, dried over anhydrous $Na_2SO_4$, filtered and evaporated to dryness under reduced pressure to give a residue, which was purified on pre-packed Silica gel column to yield the product.

i. N-(2-(Adamantan-1-Yl)Ethyl)-6-Isobutyl-2-Oxo-1,2-Dihydropyrimidine-4-Carboxamide (5)

Purification on pre-packed Silica gel column on ISCO using 0-10% MeOH in DCM (20 min). Yield: 70 mg (42%). H NMR (CDCl$_3$): δ 7.88 (t, J=5.9 Hz, 1H), 7.13 (s, 1H), 3.48-3.34 (m, 2H), 2.83-2.78 (m, 2H), 2.61 (d, J=7.3 Hz, 2H), 2.20-2.10 (m, 1H), 1.97-1.95 (m, 2H), 1.73-1.70 (m, 2H), 1.66-1.64 (m, 2H), 1.62-1.61 (m, 2H), 1.58-1.57 (m, 2H), 1.54-1.53 (m, 3H), 1.39-1.36 (m, 2H), 1.00 (d, J=6.6 Hz, 6H). HR-ESIMS: m/z 358.2494 [M+H]$^+$ calcd. for $C_{21}H_{32}N_3O_2$, found 358.2483. HPLC purity: 96% (Retention Time=15.1 min).

ii. N-(4-(Tert.-Butyl)Phenyl)-2-Oxo-1,2-Dihydropyrimidine-4-Carboxamide (30)

Purification on pre-packed Silica gel column on ISCO using 0-10% MeOH in DCM (20 min). Yield: 10 mg (21%). $^1$H NMR (CDCl$_3$): δ 9.72 (s, 1H), 8.04 (d, J=6.3 Hz, 1H), 7.66 (d, J=8.4 Hz, 2H), 7.47-7.35 (m, 3H), 1.32 (s, 9H). HR-ESIMS: m/z 272.1399 [M+H]$^+$ calcd. for $C_{15}H_{18}N_3O_2$, found 272.1393. HPLC purity: 100% (Retention Time=15.5 min).

III. N-(4-(Tert.-Butyl)Phenyl)-6-Isobutyl-2-Oxo-1,2-Dihydropyrimidine-4-Carboxamide (31)

Purification on pre-packed Silica gel column on ISCO using 0-10% MeOH in DCM (20 min). Yield: 65 mg (43%). $^1$H NMR (CDCl$_3$): δ 9.75 (s, 1H), 7.68 (d, J=8.6 Hz, 2H), 7.41 (d, J=8.6 Hz, 2H), 7.28 (s, 1H), 2.69 (d, J=7.3 Hz, 2H), 2.27-2.17 (m, 1H), 1.33 (s, 9H), 1.05 (d, J=6.6 Hz, 6H). HR-ESIMS: m/z 328.2025 [M+H]$^+$ calcd. for $C_{19}H_{26}N_3O_2$, found 328.2024. HPLC purity: 98% (Retention Time=14 min).

IV. N-((Adamantan-1-Yl)-2-Oxo-1,2-Dihydropyrimidine-4-Carboxamide (42)

Purification on pre-packed Silica gel column on ISCO using 0-10% MeOH in DCM (20 min). Yield: 77 mg (56%). $^1$H NMR (CDCl$_3$): δ 12.23 (s, 1H), 7.48 (d, J=6.7 Hz, 1H), 7.11 (s, 1H), 6.36 (d, J=6.7 Hz, 1H), 3.83 (s, 2H), 2.93 (d, J=6.1 Hz, 2H), 1.92-1.89 (m, 2H), 1.68-1.65 (m, 2H), 1.64-1.62 (m, 3H), 1.57-1.53 (m, 3H), 1.45-1.43 (m, 5H). HR-ESIMS: m/z 334.15837 [M+H]$^+$ calcd. for $C_{17}H_{24}N_3O_2S$, found 334.15825. HPLC purity: 100% (Retention Time=10.1 min).

v. N-(Adamantan-1-Yl)-6-Isobutyl-2-Oxo-1,2-Dihydropyrimidine-4-Carboxamide (43)

Purification on pre-packed Silica gel column on ISCO using 0-10% MeOH in DCM (20 min). Yield: 32 mg (21%). $^1$H NMR (CDCl$_3$): δ 7.70 (s, 1H), 7.12 (s, 1H), 2.62 (d, J=7.3 Hz, 2H), 2.22-2.14 (m, 1H), 2.14-2.02 (m, 9H), 1.78-1.64 (m, 6H), 1.01 (d, J=6.6 Hz, 6H). HR-ESIMS: m/z 330.21760 [M+H]$^+$ calcd. for $C_{19}H_{28}N_3O_2$, found 330.21747. HPLC purity: 95% (Retention Time=13.8 min).

e. Synthetic Procedure IV

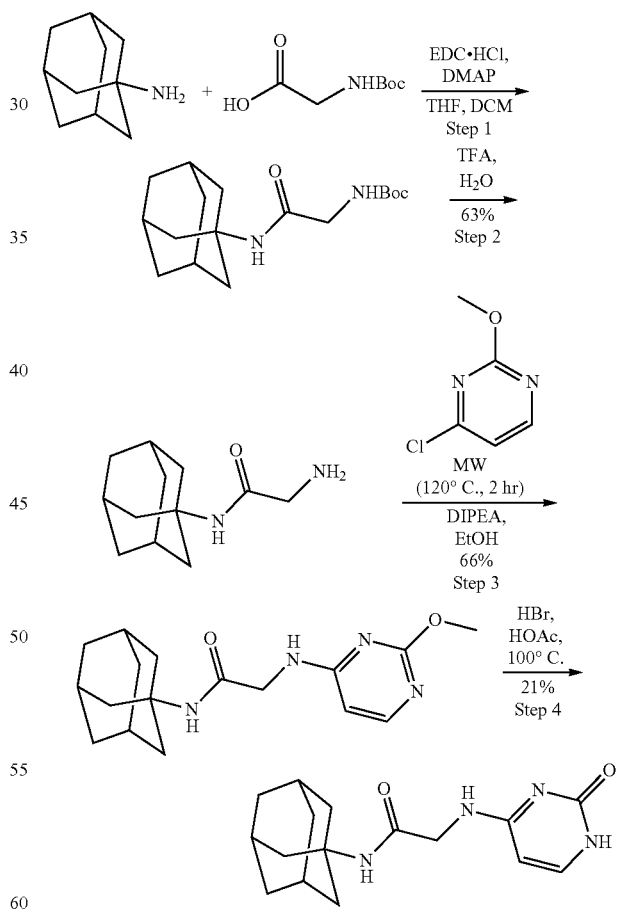

i. Step-1.

Synthesis of tert.-butyl (2-(adamantan-1-yl)amino)-2-oxoethyl)carbamate: 1-Adamantylamine (2.07 g, 13.70 mmol) was added to a solution of Boc-Gly-OH (2.00 g, 11.42 mmol), EDC hydrochloride (2.63 g, 13.70 mmol) and DMAP (0.35 g, 2.85 mmol) in anhydrous THF (25 mL) and DCM (25 mL). The reaction mixture was then stirred at room temperature for 48 hrs. The reaction mixture was quenched with saturated aqueous solution of NH₄Cl (100 mL) and extracted with DCM (3×100 mL). The organic layer was collected, dried over anhydrous Na₂SO₄, filtered and evaporated to dryness under reduced pressure to give a residue, which was used for the next step without further purification.

II. Step-2.

Synthesis of N-(adamantan-1-yl)-2-aminoacetamide: tert.-Butyl (2-(adamantan-1-yl)amino)-2-oxoethyl)carbamate (2.87 g, 9.31 mmol) from Step-1 was dissolved in TFA/H₂O mixture (22 mL, 1:1). The reaction mixture was then stirred at room temperature for 18 hrs. The reaction mixture was neutralized with 1N NaOH solution and extracted with EtOAc (3×50 mL). The organic layer was collected, dried over anhydrous Na₂SO₄, filtered and evaporated to dryness under reduced pressure to yield the product and used in next step. Yield: 1.23 g (63%). $^1$H NMR (CDCl₃) δ 3.22 (s, 2H), 2.09-2.06 (m, 3H), 2.03-2.01 (m, 6H), 1.70-1.67 (m, 6H). ESIMS: m/z 209 [M+H]$^+$.

III. Step-3.

Synthesis of N-(adamantan-1-yl)-2-((2-methoxypyrimidin-4-yl)amino)acetamide: DIPEA (0.36 mL, 2.08 mmol) was added to a solution of 4-chloro-2-methoxy-pyrimidine (0.10 g, 0.69 mmol) and N-(adamantan-1-yl)-2-aminoacetamide (0.17 g, 0.83 mmol) from Step-2 in anhydrous EtOH (3 mL). The reaction mixture was irradiated in microwave reactor at 120° C. for 2 hrs. After cooling to room temperature, the solvent was evaporated to give a residue, which was purified on pre-packed Silica gel column using 0-10% MeOH in DCM (20 min). Yield: 144 mg (66%). $^1$H NMR (CDCl₃) δ 7.98 (d, J=5.5 Hz, 1H), 6.07 (d, J=5.7 Hz, 1H), 5.80-5.55 (m, 2H), 3.98-3.93 (m, 2H), 3.92 (s, 3H), 2.07 (s, 3H), 2.02-1.87 (m, 6H), 1.72-1.63 (m, 6H). ESIMS: m/z 317.2 [M+H]$^+$.

iv. Step-4.

Synthesis of N-(adamantan-1-yl)-2-((2-oxo-1,2-dihydropyrimidin-4-yl)amino)acetamide (6): HBr (1 mL, 20% solution in EtOH) was added to a solution of N-(adamantan-1-yl)-2-((2-methoxypyrimidin-4-yl)amino)acetamide (0.054 g, 0.17 mmol) from Step-3 in glacial acetic acid (1 mL). The reaction mixture was then stirred at 100° C. for 18 hrs. After cooling to room temperature, the reaction mixture was treated with ice cold H₂O (5 mL), neutralized to pH~6 with 1N NaOH and extracted with EtOAc (3×5 mL). The organic layer was collected, dried over anhydrous Na₂SO₄, filtered and evaporated to dryness under reduced pressure to give a residue, which was purified on pre-packed Silica gel column using 0-10% MeOH in DCM (20 min). Yield: 11 mg (21%). $^1$H NMR (CD₃OD) δ 7.35 (d, J=7.1 Hz, 1H), 5.88 (d, J=7.1 Hz, 1H), 3.95 (s, 2H), 2.15-1.94 (m, 9H), 1.82-1.58 (m, 6H). HR-ESIMS: m/z 303.1821 [M+H]$^+$ calcd. for C₁₆H₂₃N₄O₂, found 303.1814. HPLC purity: 100% (Retention Time=6.9 min).

f. Synthetic Procedure V

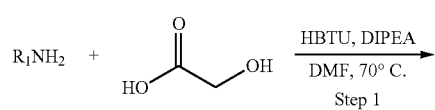

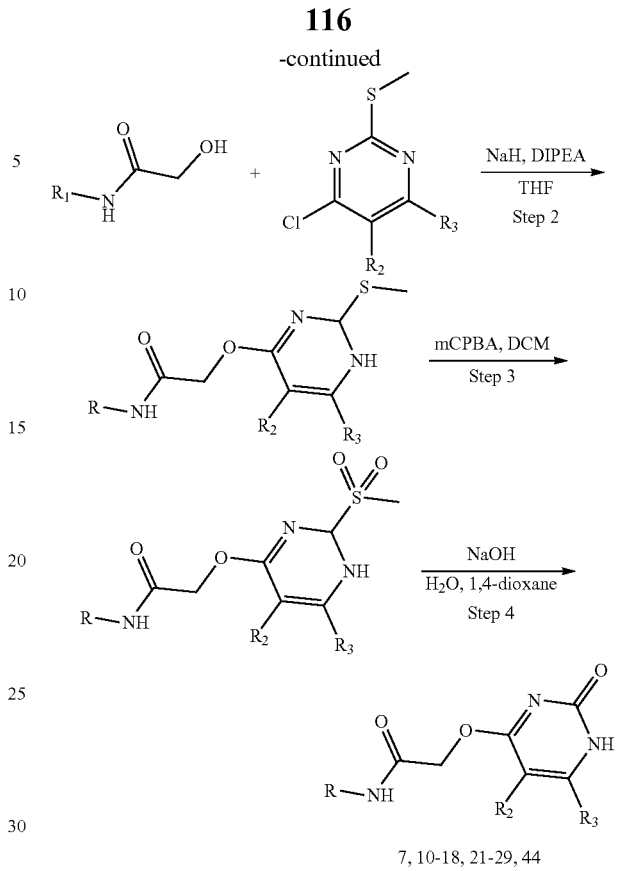

i. Step-1.

General Procedure: HBTU (1.1 mmol) and DIPEA (2 mmol) were added to a solution of corresponding amine (1 mmol) and 2-hydroxyacetic acid (1 mmol) in anhydrous DMF (6 mL) at room temperature. The reaction mixture was then stirred at 70° C. for 18 hrs. The reaction mixture was treated with saturated aqueous NaHCO₃ (15 mL) and extracted with EtOAc (3×10 mL). The organic layer was collected, dried over anhydrous Na₂SO₄, filtered and evaporated to dryness under reduced pressure to give a residue, which was used for the next step without further purification.

ii. Step-2.

General Procedure: Sodium hydride (1.5 mmol) was added to a solution of the product from Step-1 (1 mmol) in anhydrous THF (6 mL) at 0° C. After stirring for 30 min at room temperature, corresponding sulfanyl pyrimidine (1 mmol) and DIPEA (0.06 mmol) were added. The reaction mixture was then stirred at room temperature for 18 hrs. The reaction mixture was treated with saturated aqueous NH₄Cl (5 mL) and extracted with EtOAc (3×5 mL). The organic layer was collected, dried over anhydrous Na₂SO₄, filtered and evaporated to dryness under reduced pressure to give a residue, which was purified on pre-packed Silica gel column to yield the product.

(i) N-(Adamantan-1-Yl)-2-((2-(Methylthio)Pyrimidin-4-Yl)Oxy)Acetamide

Purification on pre-packed Silica gel column on ISCO using 0-70% EtOAc in Hexanes (30 min). Yield: 347 mg (40%). $^1$H NMR (CDCl₃) δ 8.30 (d, J=5.5 Hz, 1H), 6.48 (d, J=5.6 Hz, 1H), 5.86 (s, 1H), 4.74 (s, 2H), 2.54 (s, 3H), 2.09 (s, 3H), 2.07-1.99 (m, 6H), 1.76-1.62 (m, 6H). ESIMS: m/z 334.2 [M+H]$^+$.

(ii) N-(Adamantan-1-Yl)-2-((6-Isobutyl-2-(Methylthio)Pyrimidin-4-Yl)Oxy)Acetamide Purification on pre-packed Silica gel column on ISCO using 0-70% EtOAc in Hexanes (30 min). Yield: 41 mg (23%). $^1$H NMR (CDCl$_3$) δ 6.28 (s, 1H), 5.89 (s, 1H), 4.72 (s, 2H), 2.52 (s, 3H), 2.49 (d, J=7.2 Hz, 2H), 2.16-2.11 (m, 1H), 2.10-2.07 (m, 3H), 2.04-2.00 (m, 6H), 1.70-1.66 (m, 6H), 0.95-0.91 (m, 6H). ESIMS: m/z 390.2 [M+H]$^+$.

(III) N-(Adamantan-1-Yl)-2-((6-Cyclopropyl-2-(Methylthio)Pyrimidin-4-Yl)Oxy)Acetamide Purification on pre-packed Silica gel column on ISCO using 0-70% EtOAc in Hexanes (30 min). Yield: 68 mg (38%). $^1$H NMR (CDCl$_3$) δ 6.30 (s, 1H), 5.89 (s, 1H), 4.70 (s, 2H), 2.48 (s, 3H), 2.09 (s, 3H), 2.04-1.99 (m, 6H), 1.89 (tt, J=8.5, 4.4 Hz, 1H), 1.73-1.65 (m, 6H), 1.16-1.10 (m, 2H), 1.05-0.98 (m, 2H). ESIMS: m/z 374.1 [M+H]$^+$.

(IV) V-(Adamantan-1-Yl)-2-((6-Cyclobutyl-2-(Methylthio)Pyrimidin-4-Yl)Oxy)Acetamide Purification on pre-packed Silica gel column on ISCO using 0-70% EtOAc in Hexanes (30 min). Yield: 25 mg (24%). $^1$H NMR (CDCl$_3$) δ 6.35 (s, 1H), 5.85 (s, 1H), 4.73 (s, 2H), 3.64-3.53 (m, 1H), 2.56 (s, 3H), 2.38-2.23 (m, 4H), 2.10-2.01 (m, 11H), 1.70-1.68 (m, 6H). ESIMS: m/z 388.1 [M+H]$^+$.

(v) N-(Adamantan-1-Yl)-2-((6-Cyclopentyl-2-(Methylthio)Pyrimidin-4-Yl)Oxy)Acetamide Purification on pre-packed Silica gel column on ISCO using 0-70% EtOAc in Hexanes (30 min). Yield: 14 mg (24%). $^1$H NMR (CDCl$_3$) δ 6.32 (s, 1H), 5.91 (s, 1H), 4.71 (s, 2H), 3.01 (p, J=8.1 Hz, 1H), 2.52 (s, 3H), 2.08 (s, 3H), 2.04-1.99 (m, 8H), 1.82-1.72 (m, 5H), 1.70-1.67 (m, 7H). ESIMS: m/z 402.2 [M+H]$^+$.

(i) N-(Adamantan-1-Yl)-2-((6-(3,3-Difluorocyclobutyl)-2-(Methylthio)Pyrimidin-4-Yl)Oxy)Acetamide Purification on pre-packed Silica gel column on ISCO using 0-70% EtOAc in Hexanes (30 min). Yield: 185 mg (61%). $^1$H NMR (CDCl$_3$) δ 6.34 (s, 1H), 5.85 (s, 1H), 4.72 (s, 2H), 3.28 (tt, J=8.5, 4.2 Hz, 1H), 3.04-2.82 (m, 4H), 2.55 (s, 3H), 2.09 (s, 3H), 2.07-1.94 (m, 6H), 1.75-1.63 (m, 6H). ESIMS: m/z 424.2 [M+H]$^+$.

(vii) N-(Adamantan-1-Yl)-2-((2-(Methylthio)-6-Phenylpyrimidin-4-Yl)Oxy)Acetamide Purification on pre-packed Silica gel column on ISCO using 0-70% EtOAc in Hexanes (30 min). Yield: 42 mg (24%). $^1$H NMR (CDCl$_3$) δ 8.09-8.02 (m, 2H), 7.52-7.47 (m, 3H), 6.87 (s, 1H), 4.79 (s, 2H), 2.62 (s, 3H), 2.09 (s, 3H), 2.05-2.03 (m, 6H), 1.70-1.68 (m, 6H). ESIMS: m/z 410.1 [M+H]$^+$.

(viii) N-(Adamantan-1-Yl)-2-((2-(Methylthio)-6-(Trifluoromethyl)Pyrimidin-4-Yl)Oxy)Acetamide Purification on pre-packed Silica gel column on ISCO using 0-70% EtOAc in Hexanes (30 min). Yield: 34 mg (39%). $^1$H NMR (CDCl$_3$) δ 6.80 (s, 1H), 5.79 (s, 1H), 4.78 (s, 2H), 2.57 (s, 3H), 2.10 (s, 3H), 2.03-2.02 (m, 6H), 1.70-1.68 (m, 6H). ESIMS: m/z 402.1 [M+H]$^+$.

(ix) N-(Adamantan-1-Yl)-2-((6-(4-Cyanophenyl)-2-(Methylthio)Pyrimidin-4-Yl)Oxy)Acetamide Purification on pre-packed Silica gel column on ISCO using 0-70% EtOAc in Hexanes (30 min). Yield: 47 mg (28%). $^1$H NMR (CDCl$_3$) δ 8.15 (d, J=8.1 Hz, 2H), 7.77 (d, J=8.1 Hz, 2H), 6.90 (s, 1H), 5.88 (s, 1H), 4.80 (s, 2H), 2.61 (s, 3H), 2.10 (s, 3H), 2.04-2.02 (m, 6H), 1.70-1.68 (m, 6H). ESIMS: m/z 435.1 [M+H]$^+$.

(x) N-(Adamantan-1-Yl)-2-((6-Chloro-2-(Methylthio)Pyrimidin-4-Yl)Oxy)Acetamide Purification on pre-packed Silica gel column on ISCO using 0-70% EtOAc in Hexanes (30 min). Yield: 61 mg (35%). $^1$H NMR (CDCl$_3$) δ 6.52 (s, 1H), 5.79 (s, 1H), 4.73 (s, 2H), 2.53 (s, 3H), 2.09 (s, 3H), 2.04-1.98 (m, 6H), 1.72-1.65 (m, 6H). ESIMS: m/z 368.1 [M+H]$^+$.

(xi) N-(Adamantan-1-Yl)-2-((2-(Methylthio)-6,7-Dihydro-5H-Cyclopenta[D]Pyrimidin-4-Yl)Oxy)Acetamide Purification on pre-packed Silica gel column on ISCO using 0-70% EtOAc in Hexanes (30 min). Yield: 98 mg (26%). $^1$H NMR (CDCl$_3$) δ 5.83 (s, 1H), 4.77 (s, 2H), 2.99 (t, J=7.5 Hz, 2H), 2.84 (t, J=7.0 Hz, 2H), 2.55 (s, 3H), 2.21-2.13 (m, 2H), 2.09 (s, 3H), 2.02-2.00 (m, 6H), 1.70-1.68 (m, 6H). ESIMS: m/z 374.2 [M+H]$^+$.

(xii) N-(Adamantan-1-Yl)-2-((2-(Methylthio)-5,6,7,8-Tetrahydroquinazolin-4-Yl)Oxy)Acetamide Purification on pre-packed Silica gel column on ISCO using 0-70% EtOAc in Hexanes (30 min). Yield: 144 mg (40%). $^1$H NMR (CDCl$_3$) δ 5.90 (s, 1H), 4.73 (s, 2H), 2.75 (t, J=5.7 Hz, 2H), 2.55 (t, J=5.6 Hz, 2H), 2.51 (s, 3H), 2.09 (s, 3H), 2.03-1.98 (m, 6H), 1.86-1.77 (m, 4H), 1.72-1.65 (m, 6H). ESIMS: m/z 388.2 [M+H]$^+$.

(xiii) N-(Adamantan-1-Yl)-2-((2-(Methylthio)-7,8-Dihydro-5H-Pyrano[43-D]Pyrimidin-4-Yl)Oxy)Acetamide Purification on pre-packed Silica gel column on ISCO using 0-70% EtOAc in Hexanes (30 min). Yield: 97 mg (36%). $^1$H NMR (CDCl$_3$) δ 5.70 (s, 1H), 4.75 (s, 2H), 4.65 (s, 2H), 4.01 (t, J=5.6 Hz, 2H), 2.89 (t, J=5.4 Hz, 2H), 2.53 (s, 3H), 2.09 (s, 3H), 2.04-1.97 (m, 6H), 1.72-1.67 (m, 6H). ESIMS: m/z 390.2 [M+H]$^+$.

(xiv) N-(Adamantan-1-Yl)-2-((2-(Methylthio)Quinazolin-4-Yl)Oxy)Acetamide

Purification on pre-packed Silica gel column on ISCO using 0-70% EtOAc in Hexanes (30 min). Yield: 90 mg (49%). $^1$H NMR (CDCl$_3$) δ 8.04 (d, J=7.9 Hz, 1H), 7.87-7.77 (m, 2H), 7.53-7.43 (m, 1H), 5.94 (s, 1H), 4.95 (s, 2H), 2.65 (s, 3H), 2.09 (s, 3H), 2.05-2.01 (m, 6H), 1.72-1.66 (m, 6H). ESIMS: m/z 384.1 [M+H]$^+$.

(xv) N-(Adamantan-1-Yl)-2-((5-Methyl-2-(Methylthio)Pyrimidin-4-Yl)Oxy)Acetamide Purification on pre-packed Silica gel column on ISCO using 0-70% EtOAc in Hexanes (30 min). Yield: 134 mg (45%). H NMR (CDCl$_3$) δ 8.14 (s, 1H), 5.87 (s, 1H), 4.76 (s, 2H), 2.53 (s, 3H), 2.14 (s, 3H), 2.09 (s, 3H), 2.02-2.00 (m, 6H), 1.70-1.68 (m, 6H). ESIMS: m/z 348.1 [M+H]$^+$.

(xvi) N-(Adamantan-1-Yl)-2-((5-Fluoro-2-(Methylthio)Pyrimidin-4-Yl)Oxy)Acetamide Purification on pre-packed Silica gel column on ISCO using 0-70% EtOAc in Hexanes (30 min). Yield: 155 mg (39%). H NMR (CDCl$_3$) δ 8.23 (d, J=2.6 Hz, 1H), 5.94 (s, 1H), 4.79 (s, 2H), 2.53 (s, 3H), 2.10 (s, 3H), 2.06-1.98 (m, 6H), 1.75-1.65 (m, 6H). ESIMS: m/z 352.1 [M+H]$^+$.

(xvii) N-(Adamantan-2-Yl)-2-((5-Fluoro-2-(Methylthio)Pyrimidin-4-Yl)Oxy)Acetamide Purification on pre-packed Silica gel column on ISCO using 0-70% EtOAc in Hexanes (30 min). Yield: 80 mg (48%). $^1$H NMR (CDCl$_3$) δ 8.25 (d, J=2.5 Hz, 1H), 6.74 (s, 1H), 4.92 (s, 2H), 2.53 (s, 3H), 1.97-1.92 (m, 2H), 1.90-1.83 (m, 6H), 1.79-1.62 (m, 7H). ESIMS: m/z 352.1 [M+H]$^+$.

(xviii) N-(Adamantan-1-Yl)-2-((5-Chloro-2-(Methylthio)Pyrimidin-4-Yl)Oxy)Acetamide Purification on pre-packed Silica gel column on ISCO using 0-70% EtOAc in Hexanes (30 min). Yield: 150 mg (43%). $^1$H NMR (CDCl$_3$) δ 8.32 (s, 1H), 6.09 (s, 1H), 4.78 (s, 2H), 2.53 (s, 3H), 2.10 (s, 3H), 2.07-1.96 (m, 6H), 1.76-1.62 (m, 6H). ESIMS: m/z 368.1 [M+H]$^+$.

(xix) N-(Adamantan-1-Yl)-2-((5,6-Dimethyl-2-(Methylthio)Pyrimidin-4-Yl)Oxy)Acetamide Purification on pre-packed Silica gel column on ISCO using 0-70% EtOAc in Hexanes (30 min). Yield: 200 mg (52%). $^1$H NMR (CDCl$_3$) δ 5.87 (s, 1H), 4.73 (s, 2H), 2.51 (s, 3H), 2.41 (s, 3H), 2.11 (s, 3H), 2.09 (s, 3H), 2.06-1.95 (m, 6H), 1.73-1.63 (m, 6H). ESIMS: m/z 362.2 [M+H]$^+$.

(xx) Ethyl 4-((Adamantan-1-Yl)Carbamoyl)-2-(Methylthio)Pyrimidine-5-Carboxylate Purification on pre-packed Silica gel column on ISCO using 0-70% EtOAc in Hexanes (30 min). Yield: 74 mg (42%). $^1$H NMR (CDCl$_3$) δ 8.85 (s, 1H), 4.81 (s, 2H), 4.38 (q, J=7.1 Hz, 2H), 2.57 (s, 3H), 2.16-2.02 (m, 9H), 1.77-1.65 (m, 6H), 1.39 (t, J=7.1 Hz, 3H). ESIMS: m/z 406.1 [M+H]$^+$.

iii. Step-3.

General Procedure: mCPBA (2.2 mmol) was added to a solution of the product from Step-2 (1 mmol) in anhydrous DCM (20 mL) at 0° C. The reaction mixture was then stirred at room temperature for 18 hr. The reaction mixture was diluted with DCM (20 mL), washed with 5% aqueous Na$_2$S$_2$O$_3$ solution (3×20 mL) and 5% aqueous Na$_2$CO$_3$ solution (3×20 mL). The reaction mixture then washed repeatedly with H$_2$O until the aqueous washings had reached to pH 7. The undissolved solids were filtered off. The filtrate was dried over Na$_2$SO$_4$, filtered and evaporated to dryness under reduced pressure to give a residue, which was used for the next step without further purification.

iv. Step-4.

General Procedure: To a solution of the product from Step-3 (1 mmol) in anhydrous 1,4-dioxane (20 mL), 2N aqueous solution of Sodium hydroxide (2 mmol) was added and the reaction mixture was stirred at room temperature for 18 hr. The solvent was removed and the residue was dissolved in acetonitrile (10 mL), H$_2$O (10 mL) and 1N HCl (2 mL) and stirred for 10 min. The mixture was extracted with EtOAc (3×20 mL). The organic layer was collected, dried over Na$_2$SO$_4$, filtered and evaporated to dryness under reduced pressure to give a residue, which was purified on pre-packed Silica gel to yield the product.

(i) N-(Adamantan-1-Yl)-2-((2-Oxo-1,2-Dihydropyrimidin-4-Yl)Oxy)Acetamide (7)

Purification on pre-packed Silica gel column on ISCO using 0-10% MeOH in DCM (20 min). Yield: 1322 mg (50%). $^1$H NMR (CDCl$_3$): δ 7.61 (d, J=7.0 Hz, 1H), 6.05 (d, J=7.0 Hz, 1H), 5.84 (s, 1H), 4.76 (s, 2H), 2.09 (s, 3H), 2.04-2.02 (m, 6H), 1.70-1.68 (m, 6H). HR-ESIMS: m/z 304.1661 [M+H]$^+$ calcd. for C$_{16}$H$_{22}$N$_3$O$_3$, found 304.1661. HPLC purity: 100% (Retention Time=9.9 min).

(ii) N-(Adamantan-1-Yl)-2-((6-Isobutyl-2-Oxo-1,2-Dihydropyrimidin-4-Yl)Oxy)Acetamide (10)

Purification on pre-packed Silica gel column on ISCO using 0-10% MeOH in DCM (20 min). Yield: 15 mg (40%). H NMR (CDCl$_3$): δ 12.34 (s, 1H), 5.89 (s, 1H), 5.83 (s, 1H), 4.77 (s, 2H), 2.46 (d, J=7.3 Hz, 2H), 2.14-2.06 (m, 4H), 2.06-2.00 (m, 6H), 1.73-1.62 (m, 6H), 0.99 (d, J=6.7 Hz, 6H). HR-ESIMS: in/z 360.2287 [M+H]$^+$ calcd. for C$_{20}$H$_{30}$N$_3$O$_3$, found 360.2277. HPLC purity: 100% (Retention Time=12.7 min).

(iii) N-(Adamantan-1-Yl)-2-((6-Cyclopropyl-2-Oxo-1,2-Dihydropyrimidin-4-Yl)Oxy)Acetamide (11)

Purification on pre-packed Silica gel column on ISCO using 0-10% MeOH in DCM (20 min). Yield: 25 mg (49%). $^1$H NMR (CDCl$_3$): δ 5.85 (s, 1H), 5.52 (s, 1H), 4.73 (s, 2H), 2.08 (s, 3H), 2.04-1.99 (m, 6H), 1.95 (tt, J=8.3, 5.0 Hz, 1H), 1.73-1.60 (m, 6H), 1.19 (ddd, J=8.4, 7.2, 4.9 Hz, 2H), 1.00 (dt, J=7.3, 4.9 Hz, 2H). HR-ESIMS: m/z 344.1974 [M+H]$^+$ calcd. for C$_{19}$H$_{26}$N$_3$O$_3$, found 344.1971. HPLC purity: 100% (Retention Time=11.3 min).

(iv) N-(Adamantan-1-Yl)-2-((6-Cyclobutyl-2-Oxo-1,2-Dihydropyrimidin-4-Yl)Oxy)Acetamide (12)

Purification on pre-packed Silica gel column on ISCO using 0-10% MeOH in DCM (20 min). Yield: 16 mg (70%). H NMR (DMSO-d$_6$): δ 5.85 (s, 1H), 5.73 (s, 1H), 4.57 (s, 2H), 3.66-3.65 (m, 1H), 2.18-2.15 (m, 2H), 2.12-2.08 (m, 2H), 1.99 (s, 3H), 1.91-1.90 (m, 8H), 1.60-1.59 (m, 6H). HR-ESIMS: m/z 358.2131 [M+H]$^+$ calcd. for C$_{20}$H$_{28}$N$_3$O$_3$, found 358.2131. HPLC purity: 100% (Retention Time=11.9 min).

(v) N-(Adamantan-1-Yl)-2-((6-Cyclopentyl-2-Oxo-1,2-Dihydropyrimidin-4-Yl)Oxy)Acetamide (13)

Purification on pre-packed Silica gel column on ISCO using 0-10% MeOH in DCM (20 min). Yield: 6 mg (47%). H NMR (CDCl$_3$): δ 12.17 (s, 1H), 5.87 (s, 1H), 5.85 (s, 1H), 4.76 (s, 2H), 3.00 (p, J=8.3 Hz, 1H), 2.20-2.07 (m, 6H), 2.07-2.01 (m, 6H), 1.82-1.73 (m, 3H), 1.70-1.67 (m, 6H), 1.67-1.60 (m, 2H). HR-ESIMS: m/z 372.2287 [M+H]$^+$ calcd. for C$_{21}$H$_{30}$N$_3$O$_3$, found 372.2288. HPLC purity: 100% (Retention Time=13.1 min).

(vi) N-(Adamantan-1-Yl)-2-((6-(3,3-Difluorocyclobutyl)-2-Oxo-1,2-Dihydropyrimidin-4-Yl)Oxy)Acetamide (14)

Purification on pre-packed Silica gel column on ISCO using 0-10% MeOH in DCM (20 min). Yield: 58 mg (58%). H NMR (CDCl$_3$): δ 12.59 (s, 1H), 5.95 (s, 1H), 5.79 (s, 1H), 4.77 (s, 2H), 3.42-3.30 (m, 1H), 3.19-3.03 (m, 2H), 2.81-2.67 (m, 2H), 2.09 (s, 3H), 2.05-1.98 (m, 6H), 1.71-1.63 (m, 6H). HR-ESIMS: m/z 394.1942 [M+H]$^+$ calcd. for C$_{20}$H$_{26}$F$_2$N$_3$O$_3$, found 394.1937. HPLC purity: 97% (Retention Time=12.5 min).

(vii) N-(Adamantan-1-Yl)-2-((2-Oxo-6-Phenyl-1,2-Dihydropyrimidin-4-Yl)Oxy)Acetamide (15)

Purification on pre-packed Silica gel column on ISCO using 0-10% MeOH in DCM (20 min). Yield: 7 mg (41%). $^1$H NMR (CDCl$_3$): δ 7.80-7.75 (m, 2H), 7.60-7.55 (m, 3H), 6.26 (s, 1H), 5.89 (s, 1H), 4.81 (s, 2H), 2.09 (s, 3H), 2.06-2.03 (m, 6H), 1.70-1.67 (m, 6H). HR-ESIMS: m/z 380.1974 [M+H]$^+$ calcd. for C$_{22}$H$_{26}$N$_3$O$_3$, found 380.1976. HPLC purity: 100% (Retention Time=13.0 min).

(viii) N-(Adamantan-1-Yl)-2-((2-Oxo-6-(Trifluoromethyl)-1,2-Dihydropyrimidin-4-Yl)Oxy)Acetamide (16)

Purification on pre-packed Silica gel column on ISCO using 0-10% MeOH in DCM (20 min). Yield: 25 mg (81%). H NMR (CDCl$_3$): δ 6.42 (s, 1H), 5.70 (s, 1H), 4.81 (s, 2H), 2.09 (s, 3H), 2.05-2.00 (m, 6H), 1.71-1.67 (m, 6H). HR-ESIMS: m/z 372.1535 [M+H]$^+$ calcd. for C$_{17}$H$_{21}$F$_3$N$_3$O$_3$, found 372.1534. HPLC purity: 100% (Retention Time=12.5 min).

(ix) N-(Adamantan-1-Yl)-2-((6-(4-Cyanophenyl)-2-Oxo-1,2-Dihydropyrimidin-4-Yl)Oxy)Acetamide (17)

Purification on pre-packed Silica gel column on ISCO using 0-10% MeOH in DCM (20 min). Yield: 16 mg (37%). H NMR (CDCl$_3$): δ 7.91-7.85 (m, 4H), 6.31 (s, 1H), 5.74 (s, 1H), 4.82 (s, 2H), 2.10 (s, 3H), 2.05-2.03 (m, 6H), 1.70-1.68 (m, 6H). HR-ESIMS: m/z 405.1927 [M+H]$^+$ calcd. for C$_{23}$H$_{25}$N$_4$O$_3$, found 405.1922. HPLC purity: 95% (Retention Time=12.7 min).

(x) N-(Adamantan-1-Yl)-2-((6-Chloro-2-Oxo-1,2-Dihydropyrimidin-4-Yl)Oxy)Acetamide (18)

Purification on pre-packed Silica gel column on ISCO using 0-10% MeOH in DCM (20 min). Yield: 35 mg (63%). H NMR (CDCl$_3$): δ 7.64 (s, 1H), 4.78 (s, 2H), 2.10 (s, 3H), 2.07-1.97 (m, 6H), 1.74-1.66 (m, 6H). HR-ESIMS: m/z 338.1271 [M+H]$^+$ calcd. for C$_{16}$H$_{21}$ClN$_3$O$_3$, found 338.1261. HPLC purity: 100% (Retention Time=11.2 min).

(xi) N-(Adamantan-1-Yl)-2-((2-Oxo-2,5,6,7-Tetrahydro-1H-Cyclopenta[D]Pyrimidin-4-Yl)Oxy)Acetamide (21)

Purification on pre-packed Silica gel column on ISCO using 0-10% MeOH in DCM (20 min). Yield: 27 mg (30%). $^1$H NMR (CDCl$_3$): δ 5.87 (s, 1H), 4.79 (s, 2H), 2.92 (t, J=7.7 Hz, 2H), 2.75 (t, J=7.4 Hz, 2H), 2.18 (p, J=7.6 Hz, 2H), 2.09 (s, 3H), 2.04-2.01 (m, 6H), 1.70-1.67 (m, 6H). HR-ESIMS: m/z 344.1974 [M+H]$^+$ calcd. for C$_{19}$H$_{26}$N$_3$O$_3$, found 344.1973. HPLC purity: 100% (Retention Time=11.4 min).

(xii) N-(Adamantan-1-Yl)-2-((2-Oxo-1,2,5,6,7,8-Hexahydroquinazolin-4-Yl)Oxy)Acetamide (22)

Purification on pre-packed Silica gel column on ISCO using 0-10% MeOH in DCM (20 min). Yield: 66 mg (52%). $^1$H NMR (CDCl$_3$): δ 5.89 (s, 1H), 4.76 (s, 2H), 2.69-2.61 (m, 2H), 2.48-2.40 (m, 2H), 2.09 (s, 3H), 2.06-1.99 (m, 6H), 1.84-1.76 (m, 4H), 1.70-1.67 (m, 6H). HR-ESIMS: m/z 358.2131 [M+H]$^+$ calcd. for C$_{20}$H$_{28}$N$_3$O$_3$, found 358.2124. HPLC purity: 100% (Retention Time=12.3 min).

(xiii) N-(Adamantan-1-Yl)-2-((2-Oxo-1,5,7,8-Tetrahydro-2H-Pyrano[4,3-D]Pyrimidin-4-Yl)Oxy)Acetamide (23)

Purification on pre-packed Silica gel column on ISCO using 0-10% MeOH in DCM (20 min). Yield: 45 mg (54%). $^1$H NMR (CDCl$_3$): δ 5.70 (s, 1H), 4.78 (s, 2H), 4.53 (s, 2H), 3.96 (t, J=5.6 Hz, 2H), 2.74 (t, J=5.8 Hz, 2H), 2.09 (s, 3H), 2.05-1.97 (m, 6H), 1.70-1.67 (m, 6H). HR-ESIMS: m/z 360.1923 [M+H]$^+$ calcd. for C$_{19}$H$_{26}$N$_3$O$_4$, found 360.1919. HPLC purity: 100% (Retention Time=10.4 min).

(xiv) N-(Adamantan-1-Yl)-2-((2-Oxo-1,2-Dihydroquinazolin-4-Yl)Oxy)Acetamide (24)

Purification on pre-packed Silica gel column on ISCO using 0-10% MeOH in DCM (20 min). Yield: 8 mg (24%). $^1$H NMR (CDCl$_3$): δ 11.82 (s, 1H), 7.93 (d, J=8.1 Hz, 1H), 7.69 (ddd, J=8.5, 7.2, 1.4 Hz, 1H), 7.42 (d, J=8.3 Hz, 1H), 7.29 (d, J=7.1 Hz, 1H), 5.91 (s, 1H), 4.99 (s, 2H), 2.10 (s, 3H), 2.09-2.02 (m, 6H), 1.74-1.65 (m, 6H). HR-ESIMS: m/z 354.1818 [M+H]$^+$ calcd. for C$_{20}$H$_{24}$N$_3$O$_3$, found 354.1814. HPLC purity: 96% (Retention Time=3.2 min).

(xv) N-(Adamantan-1-Yl)-2-((5-Methyl-2-Oxo-1,2-Dihydropyrimidin-4-Yl)Oxy)Acetamide (25)

Purification on pre-packed Silica gel column on ISCO using 0-10% MeOH in DCM (20 min). Yield: 37 mg (30%). $^1$H NMR (CDCl$_3$): δ 7.39 (s, 1H), 5.88 (s, 1H), 4.78 (s, 2H), 2.09 (s, 3H), 2.05-2.01 (m, 9H), 1.70-1.68 (m, 6H). HR-ESIMS: m/z 318.1818 [M+H]$^+$ calcd. for C$_{17}$H$_{24}$N$_3$O$_3$, found 318.1818. HPLC purity: 100% (Retention Time=10.5 min).

(xvi) N-(ADAMANTAN-1-YL)-2-((5-FLUORO-2-OXO-1,2-DIHYDROPYRIMIDIN-4-YL)OXY)ACETAMIDE (26)

Purification on pre-packed Silica gel column on ISCO using 0-10% MeOH in DCM (20 min). Yield: 36 mg (27%). $^1$H NMR (CDCl$_3$): δ 7.56 (d, J=4.2 Hz, 1H), 5.89 (s, 1H), 4.80 (s, 2H), 2.10 (s, 3H), 2.07-1.98 (m, 6H), 1.73-1.64 (m, 6H). HR-ESIMS: m/z 322.1567 [M+H]$^+$ calcd. for C$_{16}$H$_{21}$FN$_3$O$_3$, found 322.1560. HPLC purity: 95% (Retention Time=10.2 min).

(xvii) N-(Adamantan-2-Yl)-2-((5-Fluoro-2-Oxo-1,2-Dihydropyrimidin-4-Yl)Oxy)Acetamide (27)

Purification on pre-packed Silica gel column on ISCO using 0-10% MeOH in DCM (20 min). Yield: 20 mg (27%). $^1$H NMR (DMSO-d$_6$): δ 8.01 (d, J=5.6 Hz, 1H), 7.96 (d, J=7.5 Hz, 1H), 4.85 (s, 2H), 1.99-1.90 (m, 2H), 1.85-1.61 (m, 11H), 1.53-1.44 (m, 2H). HR-ESIMS: m/z 322.1567 [M+H]$^+$ calcd. for $C_{16}H_{21}FN_3O_3$, found 322.1558. HPLC purity: 100% (Retention Time=10.2 min).

(xviii) N-(Adamantan-1-Yl)-2-((5-Chloro-2-Oxo-1,2-Dihydropyrimidin-4-Yl)Oxy)Acetamide (28)

Purification on pre-packed Silica gel column on ISCO using 0-10% MeOH in DCM (20 min). Yield: 40 mg (30%). $^1$H NMR (DMSO-d$_6$): δ 7.45 (s, 1H), 4.64 (s, 2H), 1.98 (s, 3H), 1.95-1.81 (m, 6H), 1.67-1.50 (m, 6H). HR-ESIMS: m/z 338.1271 [M+H]$^+$ calcd. for $C_{16}H_{21}ClN_3O_3$, found 338.1268. HPLC purity: 100% (Retention Time=11.1 min).

(xix) N-(Adamantan-1-Yl)-2-((5,6-Dimethyl-2-Oxo-1,2-Dihydropyrimidin-4-Yl)Oxy)Acetamide (29)

Purification on pre-packed Silica gel column on ISCO using 0-10% MeOH in DCM (20 min). Yield: 71 mg (40%). $^1$H NMR (CDCl$_3$): δ 12.81 (s, 1H), 5.89 (s, 1H), 4.77 (s, 2H), 2.34 (s, 3H), 2.09 (s, 3H), 2.05-2.00 (m, 6H), 1.99 (s, 3H), 1.71-1.66 (m, 6H). HR-ESIMS: m/z 332.1974 [M+H]$^+$ calcd. for $C_{18}H_{26}N_3O_3$, found 332.1971. HPLC purity: 96% (Retention Time=11.0 min).

(xx) Ethyl 4-((Adamantan-1-Yl)Carbamoyl)-2-Oxo-1,2-Dihydropyrimidine-5-Carboxylate (44)

Purification on pre-packed Silica gel column on ISCO using 0-10% MeOH in DCM (20 min). Yield: 12 mg (56%). $^1$H NMR (CDCl$_3$): δ 12.43 (s, 1H), 8.44 (s, 1H), 7.18 (s, 1H), 4.77 (s, 2H), 4.34 (q, J=7.1 Hz, 2H), 2.13-2.07 (m, 8H), 1.75-1.65 (m, 7H), 1.36 (t, J=7.1 Hz, 3H). HR-ESIMS: m/z 376.18670 [M+H]$^+$ calcd. for $C_{19}H_{26}N_3O_5$, found 376.18643. HPLC purity: 100% (Retention Time=12.4 min).

g. Synthetic Procedure VI

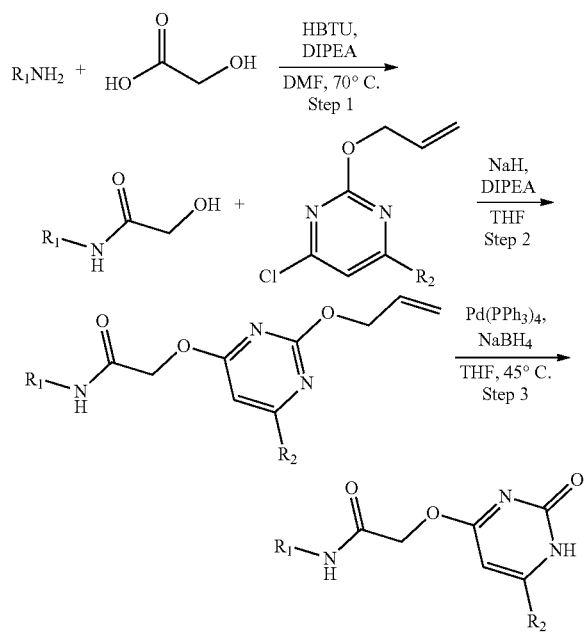

8, 9 i. Step-1.

General Procedure: HBTU (1.1 mmol) and DIPEA (2 mmol) were added to a solution of corresponding amine (1 mmol) and 2-hydroxyacetic acid (1 mmol) in anhydrous DMF (6 mL) at room temperature. The reaction mixture was then stirred at 70° C. for 18 hrs. The reaction mixture was treated with saturated aqueous NaHCO$_3$ (15 mL) and extracted with EtOAc (3×10 mL). The combined organic layer was collected, dried over anhydrous Na$_2$SO$_4$, filtered and evaporated to dryness under reduced pressure to give a residue, which was used for the next step without further purification.

ii. Step-2.

General Procedure: Sodium hydride (1.5 mmol) was added to a solution of the product from Step-1 (1 mmol) in anhydrous THF (6 mL) at 0° C. After stirring for 30 min at room temperature, corresponding pyrimidine (1 mmol) and DIPEA (0.06 mmol) were added. The reaction mixture was then stirred at room temperature for 18 hrs. The reaction mixture was treated with saturated aqueous NH$_4$Cl (5 mL) and extracted with EtOAc (3×5 mL). The organic layer was collected, dried over anhydrous Na$_2$SO$_4$, filtered and evaporated to dryness under reduced pressure to give a residue, which was purified on pre-packed Silica gel to yield the product.

(i) N-(Adamantan-2-Yl)-2-((2-(Allyloxy)Pyrimidin-4-Yl)Oxy)Acetamide

Purification on pre-packed Silica gel column on ISCO using 0-70% EtOAc in Hexanes (30 min). Yield: 60 mg (37%). $^1$H NMR (CDCl$_3$) δ 8.31 (d, J=5.6 Hz, 1H), 6.62 (s, 1H), 6.51 (d, J=5.6 Hz, 1H), 6.11-6.01 (m, 1H), 5.45-5.37 (m, 1H), 5.31-5.23 (m, 1H), 4.87 (s, 2H), 4.87-4.84 (m, 2H), 1.96-1.91 (m, 2H), 1.89-1.82 (m, 6H), 1.75-1.73 (m, 2H), 1.67-1.65 (m, 3H), 1.57-1.54 (m, 2H). ESIMS: m/z 344.2 [M+H]$^+$.

(ii) N-(Adamantan-1-Yl)-2-((2-(Allyloxy)-6-Methylpyrimidin-4-Yl)Oxy)Acetamide

Purification on pre-packed Silica gel column on ISCO using 0-70% EtOAc in Hexanes (30 min). Yield: 17 mg (10%). $^1$H NMR (CDCl$_3$) δ 6.31 (s, 1H), 6.05 (ddt, J=17.2, 10.5, 5.6 Hz, 1H), 5.88 (s, 1H), 5.41 (dq, J=17.3, 1.6 Hz, 1H), 5.25 (dq, J=10.5, 1.3 Hz, 1H), 4.84 (dt, J=5.6, 1.4 Hz, 2H), 4.70 (s, 2H), 2.39 (s, 3H), 2.08 (s, 3H), 2.05-1.99 (m, 6H), 1.70-1.66 (m, 6H). ESIMS: m/z 358.2 [M+H]$^+$.

iii. Step-3.

General Procedure: Sodium borohydride (4 mmol) was added to a solution of the product from Step-2 (1 mmol) and tetrakis(triphenylphosphine) palladium (0.05 mmol) in anhydrous THF (24 mL) at 0° C. The reaction mixture was then stirred at 45° C. for 1 hr. After cooling to room temperature, the reaction mixture was acidified to pH-5 with 1N HCl. H$_2$O (20 mL) was added to the mixture and extracted with EtOAc (3×20 mL). The organic layer was collected, dried over Na$_2$SO$_4$, filtered and evaporated to dryness under reduced pressure to give a residue, which was purified on pre-packed Silica gel to yield the product.

(i) N-(Adamantan-2-Yl)-2-((2-Oxo-1,2-Dihydropyrimidin-4-Yl)Oxy)Acetamide (8)

Purification on pre-packed Silica gel column on ISCO using 0-10% MeOH in DCM (20 min). Yield: 19 mg (36%). $^1$H NMR (CDCl$_3$): δ 11.87 (s, 1H), 7.63 (d, J=6.9 Hz, 1H), 6.58 (d, J=8.1 Hz, 1H), 6.08 (d, J=7.0 Hz, 1H), 4.90 (s, 2H), 1.98-1.92 (m, 2H), 1.87-1.84 (m, 4H), 1.77-1.63 (m, 6H), 1.61-1.55 (m, 3H). HR-ESIMS: m/z 304.1661 [M+H]$^+$ calcd. for $C_{16}H_{22}N_3O_3$, found 304.1661. HPLC purity: 100% (Retention Time=9.4 min).

(ii) N-(Adamantan-1-Yl)-2-((6-Methyl-2-Oxo-1,2-Dihydropyrimidin-4-Yl)Oxy)Acetamide (9)

Purification on pre-packed Silica gel column on ISCO using 0-10% MeOH in DCM (20 min). Yield: 6 mg (40%). $^1$H NMR (CDCl$_3$): δ 12.78 (s, 1H), 5.86 (s, 1H), 5.83 (s, 1H), 4.76 (s, 2H), 2.35 (s, 3H), 2.09 (s, 3H), 2.06-1.94 (m, 6H), 1.77-1.64 (m, 6H). HR-ESIMS: m/z 318.1818 [M+H]$^+$ calcd. for $C_{17}H_{24}N_3O_3$, found 318.1814. HPLC purity: 100% (Retention Time=10.2 min).

h. Synthetic Procedure VII

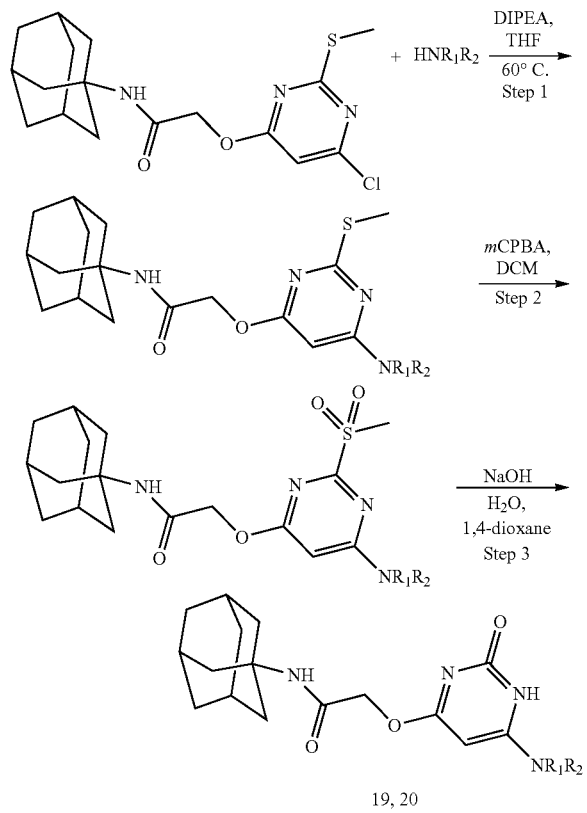

i. Step-1.

General Procedure: Corresponding amine (1.1 mmol) was added to a solution of N-(adamantan-1-yl)-2-((6-chloro-2-(methylthio)pyrimidin-4-yl)oxy)acetamide (1 mmol) and DIPEA (2.2 mmol) in anhydrous THF (7 mL) at room temperature. The reaction mixture was then stirred at 60° C. for 18 hrs. The reaction mixture was treated with H$_2$O (15 mL) and extracted with EtOAc (3×15 mL). The organic layer was collected, dried over anhydrous Na$_2$SO$_4$, filtered and evaporated to dryness under reduced pressure to give a residue, which was purified on pre-packed Silica gel to yield the product.

(i) N-(Adamantan-1-Yl)-2-((2-(Methylthio)-6-Morpholinopyrimidin-4-Yl)Oxy)Acetamide Purification on pre-packed Silica gel column on ISCO using 0-70% EtOAc in Hexanes (30 min). Yield: 57 mg (33%). $^1$H NMR (CDCl$_3$) δ 5.93 (s, 1H), 5.57 (s, 1H), 4.67 (s, 2H), 3.77-3.74 (m, 4H), 3.57 (t, J=4.8 Hz, 4H), 2.48 (s, 3H), 2.08 (s, 3H), 2.02-2.00 (m, 6H), 1.70-1.67 (m, 6H). ESIMS: m/z 419.2 [M+H]$^+$.

(ii) N-(Adamantan-1-Yl)-2-((6-(3,3-Difluoroazetidin-1-Yl)-2-(Methylthio)Pyrimidin-4-Yl)Oxy)Acetamide Purification on pre-packed Silica gel column on ISCO using 0-70% EtOAc in Hexanes (30 min). Yield: 51 mg (44%). $^1$H NMR (CDCl$_3$) δ 5.88 (s, 1H), 5.39 (s, 1H), 4.68 (s, 2H), 4.38 (t, J=11.9 Hz, 4H), 2.48 (s, 3H), 2.08 (s, 3H), 2.06-1.92 (m, 6H), 1.73-1.63 (m, 6H). ESIMS: m/z 425.2 [M+H]$^+$.

ii. Step-2.

General Procedure: mCPBA (2.2 mmol) was added to a solution of the product from Step-1 (1 mmol) in anhydrous DCM (20 mL) at 0° C. The reaction mixture was then stirred at room temperature for 18 hr. The reaction mixture was diluted with DCM (20 mL), washed with 5% aqueous Na$_2$S$_2$O$_3$ solution (3×20 mL) and 5% aqueous Na$_2$CO$_3$ solution (3×20 mL). The reaction mixture then washed repeatedly with H$_2$O until the aqueous washings had reached to pH~7. The undissolved solids were filtered off. The filtrate was dried over Na$_2$SO$_4$, filtered and evaporated to dryness under reduced pressure to give a residue, which was used for the next step without further purification.

iii. Step-3.

General Procedure: To a solution of the product from Step-2 (1 mmol) in anhydrous 1,4-dioxane (20 mL) was added 2N aqueous sodium hydroxide solution (2 mmol). The reaction mixture was then stirred at room temperature for 18 hr. The solvent was removed and the residue was dissolved in acetonitrile (10 mL), H$_2$O (10 mL) and 1N HCl (2 mL) and stirred for 10 min. The mixture was extracted with EtOAc (3×20 mL). The organic layer was collected, dried over Na$_2$SO$_4$, filtered and evaporated to dryness under reduced pressure to give a residue, which was purified on pre-packed Silica gel to yield the product.

(i) N-(Adamantan-1-Yl)-2-((6-Morpholino-2-Oxo-1,2-Dihydropyrimidin-4-Yl)Oxy)Acetamide (19)

Purification on pre-packed Silica gel column on ISCO using 0-10% MeOH in DCM (20 min). Yield: 42 mg (80%). 1H NMR (CDCl$_3$): δ 11.86 (s, 1H), 5.98 (s, 1H), 5.17 (s, 1H), 4.65 (s, 2H), 3.80 (t, J=4.9 Hz, 4H), 3.62-3.46 (m, 4H), 2.09 (s, 3H), 2.06-1.98 (m, 6H), 1.72-1.62 (m, 6H). HR-ESIMS: m/z 389.2189 [M+H]$^+$ calcd. for $C_{20}H_{29}N_4O_4$, found 389.2189. HPLC purity: 100% (Retention Time=9.2 min).

(ii) N-(Adamantan-1-Yl)-2-((6-(3,3-Difluoroazetidin-1-Yl)-2-Oxo-1,2-Dihydropyrimidin-4-Yl)Oxy)Acetamide (20)

Purification on pre-packed Silica gel column on ISCO using 0-10% MeOH in DCM (20 min). Yield: 20 mg (43%). $^1$H NMR (CDCl$_3$): δ 5.92 (s, 1H), 4.93 (s, 1H), 4.67 (s, 2H), 4.54 (t, J=11.5 Hz, 4H), 2.09 (s, 3H), 2.06-1.97 (m, 6H), 1.71-1.65 (m, 6H). HR-ESIMS: m/z 395.1895 [M+H]$^+$ calcd. for $C_{19}H_{25}F_2N_4O_3$, found 395.1894. HPLC purity: 100% (Retention Time=10.1 min).

i. Synthetic Protocol VIII

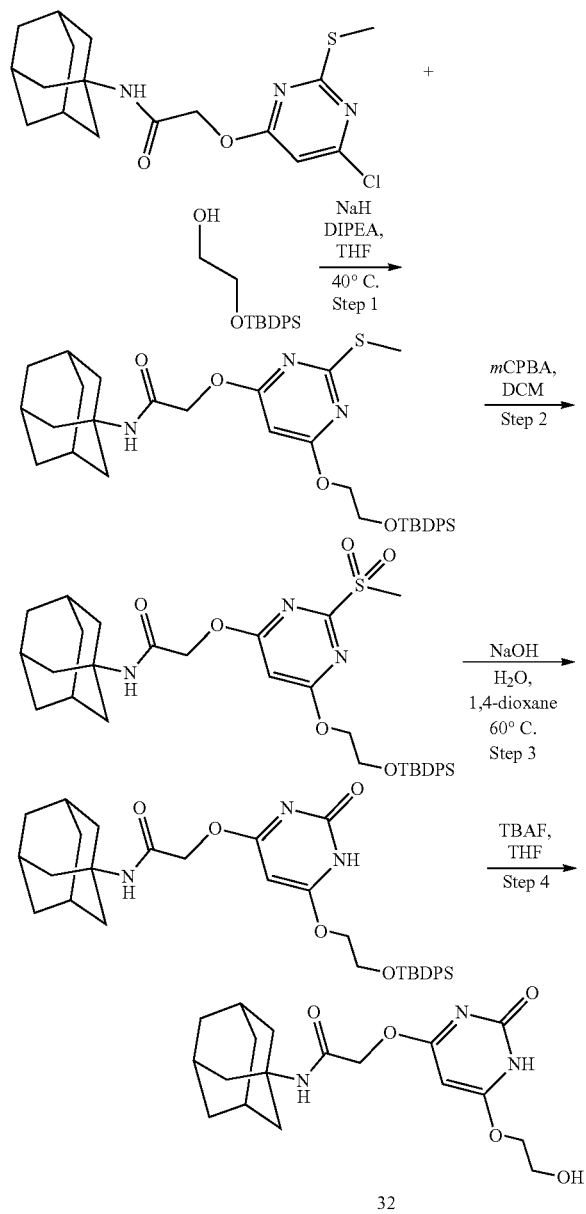

i. Step-1.

Synthesis of N-(adamantan-1-yl)-2-((6-(2-((tert.-butyldiphenylsilyl)oxy)ethoxy)-2-(methylthio)pyrimidin-4-yl)oxy)acetamide: Sodium hydride (0.14 g, 3.57 mmol) was added to a solution of 2-((tert.-butyldiphenylsilyl)oxy)ethan-1-ol (0.32 g, 1.07 mmol) in anhydrous THF (7 mL) at 0° C. After stirring for 30 min at room temperature, N-(adamantan-1-yl)-2-((6-chloro-2-(methylthio)pyrimidin-4-yl)oxy)acetamide (0.39 g, 1.07 mmol) and DIPEA (0.025 mL, 0.14 mmol) were added. The reaction mixture was then stirred at 40° C. for 18 hrs. The reaction mixture was treated with saturated aqueous NH₄Cl (10 mL) and extracted with EtOAc (3×20 mL). The organic layer was collected, dried over anhydrous Na₂SO₄, filtered and evaporated to dryness under reduced pressure to give a residue, which was purified on pre-packed Silica gel on ISCO column using 0-70% EtOAc in Hexanes (30 min). Yield: 213 mg (31%). ¹H NMR (CDCl₃) δ 7.69-7.64 (m, 4H), 7.44-7.35 (m, 6H), 5.92 (s, 1H), 5.77 (s, 1H), 4.69 (s, 2H), 4.51-4.43 (m, 2H), 3.99-3.92 (m, 2H), 2.48 (s, 3H), 2.08 (s, 3H), 2.03-2.01 (m, 6H), 1.70-1.67 (m, 6H), 1.04 (s, 9H). ESIMS: m/z 632.3 [M+H]⁺.

ii. Step-2.

Synthesis of N-(adamantan-1-yl)-2-((6-(2-((tert.-butyldiphenylsilyl)oxy)ethoxy)-2-(methylsulfonyl)pyrimidin-4-yl)oxy)acetamide: mCPBA (0.16 ng, 0.71 mmol) was added to a solution of N-(adamantan-1-yl)-2-((6-(2-((tert.-butyldiphenylsilyl)oxy)ethoxy)-2-(methylthio)pyrimidin-4-yl)oxy)acetamide (0.21 g, 0.34 mmol) in anhydrous DCM (9 mL) at 0° C. The reaction mixture was then stirred at room temperature for 18 hr. The reaction mixture was diluted with DCM (9 mL), washed with 5% aqueous Na₂S₂O₃ solution (3×9 mL) and 5% aqueous Na₂CO₃ (3×9 mL) solution. The reaction mixture then washed repeatedly with H₂O until the aqueous washings had reached to pH~7. The undissolved solids were filtered off. The filtrate was dried over Na₂SO₄, filtered and evaporated to dryness under reduced pressure to give a residue, which was used for the next step without further purification.

iii. Step-3.

Synthesis of N-(adamantan-1-yl)-2-((6-(2-((tert.-butyldiphenylsilyl)oxy)ethoxy)-2-oxo-1,2-dihydropyrimidin-4-yl)oxy)acetamide: To a solution of N-(adamantan-1-yl)-2-((6-(2-((tert.-butyldiphenylsilyl)oxy)ethoxy)-2-(methylsulfonyl)pyrimidin-4-yl)oxy)acetamide (0.22 g, 0.34 mmol) from Step-2 in anhydrous 1,4-dioxane (9 mL) was added 2N aqueous sodium hydroxide (0.34 mL, 0.67 mmol). The reaction mixture was then stirred at 60° C. for 18 hr. The solvent was removed and the residue was dissolved in acetonitrile (5 mL), H₂O (5 mL) and 1N HCl (0.9 mL) and stirred for 10 min. The mixture was extracted with EtOAc (3×10 mL). The organic layer was collected, dried over Na₂SO₄, filtered and evaporated to dryness under reduced pressure to give a residue, which was used for the next step without further purification.

iv. Step-4.

Synthesis of N-(adamantan-1-yl)-2-((6-(2-hydroxyethoxy)-2-oxo-1,2-dihydropyrimidin-4-yl)oxy)acetamide (32): TBAF (1M solution in THF) (0.23 mL, 0.23 mmol) was added to a solution of N-(adamantan-1-yl)-2-((6-(2-((tert-butyldiphenylsilyl)oxy)ethoxy)-2-oxo-1,2-dihydropyrimidin-4-yl)oxy)acetamide (0.07 g, 0.12 mmol) from Step-3 in anhydrous THF (4 mL) at 0° C. The reaction mixture was then stirred at room temperature for 18 hrs. The reaction mixture was concentrated and purified on pre-packed Silica gel using 0-10% MeOH in DCM (20 min). Yield: 20 mg (47%). ¹H NMR (DMSO-d₆): δ 7.35 (s, 1H), 5.73 (s, 1H), 4.55 (s, 2H), 4.26-4.08 (m, 2H), 3.72-3.59 (m, 2H), 1.99 (s, 3H), 1.94-1.82 (m, 6H), 1.70-1.48 (m, 6H). HR-ESIMS: m/z 364.1872 [M+H]⁺ calcd. for C₁₈H₂₆N₃O₅, found 364.1873. HPLC purity: 96% (Retention Time=9.1 min).

j. Synthetic Protocol IX

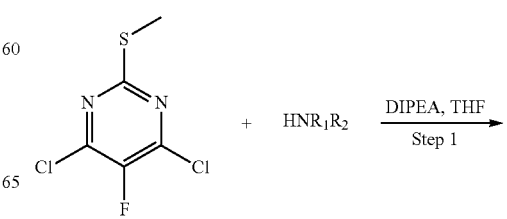

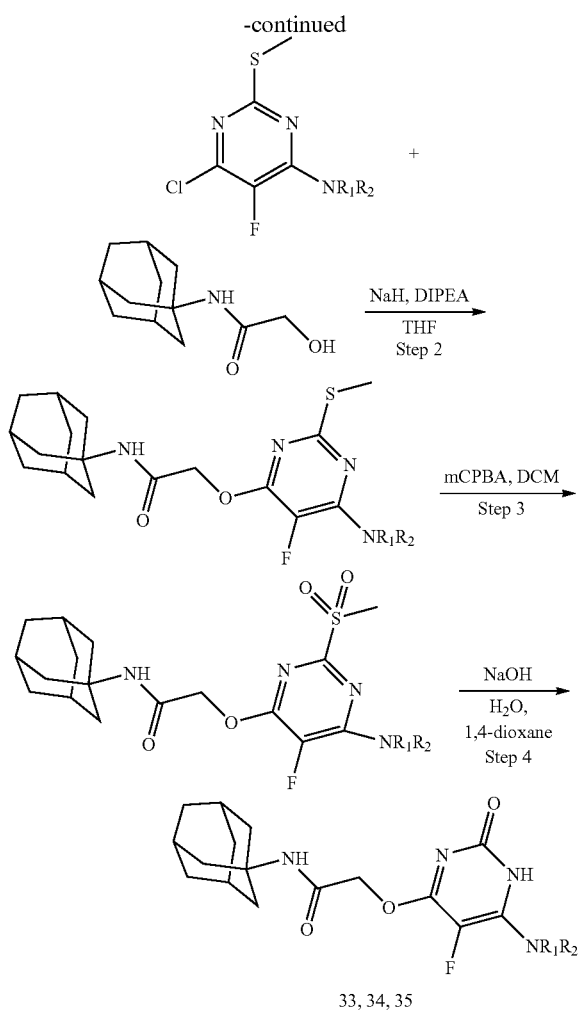

i. Step-1.

General Procedure: Corresponding amine (1 mmol) was added to a solution of 4,6-dichloro-5-fluoro-2-(methylthio) pyrimidine (1 mmol) and DIPEA (1.1 mmol) in anhydrous THF (4 mL) at rt. A precipitate is formed immediately. The reaction mixture was treated with $H_2O$, filtered and the solid was washed with $H_2O$, followed by drying under vacuum to yield the product.

(i) 4-(6-Chloro-5-Fluoro-2-(Methylthio)Pyrimidin-4-Yl)Morpholine

Yield: 188 mg (76%). $^1$H NMR (CDCl$_3$) δ 3.85-3.74 (m, 8H), 2.48 (s, 3H). ESIMS: m/z 264.0 [M+H]$^+$.

(ii) 8-(6-Chloro-5-Fluoro-2-(Methylthio)Pyrimidin-4-Yl)-3-Oxa-8-Azabicyclo[3.2.1]Octane Yield: 244 mg (90%). $^1$H NMR (CDCl$_3$) δ 4.78-4.62 (m, 2H), 3.79 (d, J=11.1 Hz, 2H), 3.64 (d, J=10.5 Hz, 2H), 2.47 (s, 3H), 2.17-2.08 (m, 2H), 2.07-1.98 (m, 2H). ESIMS: m/z 290.1 [M+H]$^+$.

(iii) 4-Chloro-6-(3,3-Difluoroazetidin-1-Yl)-5-Fluoro-2-(Methylthio)Pyrimidine

Yield: 209 mg (83%). $^1$H NMR (CDCl$_3$) δ 4.59 (td, J=11.9, 1.9 Hz, 4H), 2.48 (s, 3H). ESIMS: m/z 270.0 [M+H]$^+$.

ii. Step-2.

General Procedure: To a solution of N-(adamantan-1-yl)-2-hydroxyacetamide (1 mmol) from Step-1 in anhydrous THF (6 mL) was added sodium hydride (1.5 mmol) at 0° C. After stirring for 30 min at room temperature, the product DIPEA (0.06 mmol) was added. The reaction mixture was then stirred at room temperature for 18 hrs. The reaction mixture was treated with saturated NH$_4$Cl solution (5 mL) and extracted with EtOAc (3×5 mL). The organic layer was collected, dried over anhydrous Na$_2$SO$_4$, filtered and evaporated to dryness under reduced pressure to give a residue, which was purified on pre-packed Silica gel to yield the product.

(i) N-(Adamantan-1-Yl)-2-((5-Fluoro-2-(Methylthio)-6-Morpholinopyrimidin-4-Yl)Oxy)Acetamide Purification on pre-packed Silica gel column on ISCO using 0-70% EtOAc in Hexanes (30 min). Yield: 90 mg (29%). $^1$H NMR (CDCl$_3$) δ 6.01 (s, 1H), 4.71 (s, 2H), 3.76 (t, J=7.0 Hz, 8H), 2.45 (s, 3H), 2.08 (s, 3H), 2.04-1.95 (m, 6H), 1.74-1.61 (m, 6H). ESIMS: m/z 437.2 [M+H]$^+$.

(ii) 2-((6-(3-Oxa-8-Azabicyclo[3.2.1]Octan-8-Yl)-5-Fluoro-2-(Methylthio)Pyrimidin-4-Yl)Oxy)-N-(Adamantan-1-Yl)Acetamide Purification on pre-packed Silica gel column on ISCO using 0-70% EtOAc in Hexanes (30 min). Yield: 111 mg (28%). $^1$H NMR (CDCl$_3$) δ 6.03 (s, 1H), 4.71 (s, 2H), 4.68-4.58 (m, 2H), 3.80 (d, J=11.0 Hz, 2H), 3.61 (d, J=11.7 Hz, 2H), 2.45 (s, 3H), 2.14-2.06 (m, 5H), 2.06-1.97 (m, 8H), 1.73-1.65 (m, 6H). ESIMS: m/z 463.2 [M+H]$^+$.

(iii) N-(Adamantan-1-Yl)-2-((6-(3,3-Difluoroazetidin-1-Yl)-5-Fluoro-2-(Methylthio)Pyrimidin-4-Yl)Oxy)Acetamide Purification on pre-packed Silica gel column on ISCO using 0-70% EtOAc in Hexanes (30 min). Yield: 162 mg (47%). $^1$H NMR (CDCl$_3$) δ 5.95 (s, 1H), 4.71 (s, 2H), 4.54 (td, J=12.1, 1.9 Hz, 4H), 2.46 (s, 3H), 2.09 (s, 3H), 2.04-1.99 (m, 6H), 1.73-1.66 (m, 6H). ESIMS: m/z 443.1 [M+H]$^+$.

iii. Step-3.

General Procedure: mCPBA (2.2 mmol) was added to a solution of the product from Step-2 (1 mmol) in anhydrous DCM (20 mL) at 0° C. The reaction mixture was then stirred at room temperature for 18 hr. The reaction mixture was diluted with DCM (20 mL), washed with 5% aqueous Na$_2$S$_2$O$_3$ solution (3×20 mL) and 5% aqueous Na$_2$CO$_3$ solution (3×20 mL). The reaction mixture then washed repeatedly with H$_2$O until the aqueous washings had reached to pH~7. The undissolved solids were filtered off. The filtrate was dried over Na$_2$SO$_4$, filtered and evaporated to dryness under reduced pressure to give a residue, which was used for the next step without further purification.

iv. Step-4.

General Procedure: To a solution of the product from Step-3 (1 mmol) in anhydrous 1,4-dioxane (20 mL), 2N aqueous sodium hydroxide (2 mmol) was added. The reaction mixture was then stirred at room temperature for 18 hr. The solvent was removed and the residue was dissolved in acetonitrile (10 mL), H$_2$O (10 mL) and HCl (1N, 2 mL) and stirred for 10 min. The mixture was extracted with EtOAc (3×20 mL). The organic layer was collected, dried over Na$_2$SO$_4$, filtered and evaporated to dryness under reduced pressure to give a residue, which was purified on pre-packed Silica gel to yield the product.

(i) N-(Adamantan-1-Yl)-2-((5-Fluoro-6-Morpholino-2-Oxo-1,2-Dihydropyrimidin-4-Yl)Oxy)Acetamide (33)

Purification on pre-packed Silica gel column on ISCO using 0-10% MeOH in DCM (20 min). Yield: 39 mg (47%). $^1$H NMR (CD$_3$OD): δ 4.68 (s, 2H), 3.76-3.72 (m, 4H), 3.68-3.59 (m, 4H), 2.07-2.02 (m, 9H), 1.74-1.70 (m, 6H). HR-ESIMS: m/z 407.2095 [M+H]$^+$ calcd. for C$_{20}$H$_{28}$FN$_4$O$_4$, found 407.2089. HPLC purity: 95% (Retention Time=13.3 min).

(ii) 2-((6-(3-Oxa-8-Azabicyclo[3.2.1]Octan-8-Yl)-5-Fluoro-2-Oxo-1,2-Dihydropyrimidin-4-Yl)Oxy)-N-(Adamantan-1-Yl)Acetamide (34)

Purification on pre-packed Silica gel column on ISCO using 0-10% MeOH in DCM (20 min). Yield: 43 mg (45%). $^1$H NMR (CD$_3$OD): δ 4.69 (s, 2H), 4.58-4.54 (m, 2H), 3.79 (d, J=11.1 Hz, 2H), 3.59 (d, J=11.1 Hz, 2H), 2.09-2.02 (m, 13H), 1.74-1.70 (m, 6H). HR-ESIMS: m/z 433.2251 [M+H]$^+$ calcd. for C$_{22}$H$_{30}$FN$_4$O$_4$, found 433.2249. HPLC purity: 100% (Retention Time=12.9 min).

(iii) N-(Adamantan-1-Yl)-2-((6-(3,3-Difluoroazetidin-1-Yl)-5-Fluoro-2-Oxo-1,2-Dihydropyrimidin-4-Yl)Oxy)Acetamide (35)

Purification on pre-packed Silica gel column on ISCO using 0-10% MeOH in DCM (20 min). Yield: 26 mg (37%). $^1$H NMR (CD$_3$OD): δ 4.69 (s, 2H), 4.54 (td, J=12.2, 2.0 Hz, 4H), 2.10-1.98 (m, 9H), 1.75-1.67 (m, 6H). HR-ESIMS: m/z 413.1801 [M+H]$^+$ calcd. for C$_{19}$H$_{24}$F$_3$N$_4$O$_3$, found 413.1801. HPLC purity: 100% (Retention Time=13.7 min).

k. Synthetic Procedure X

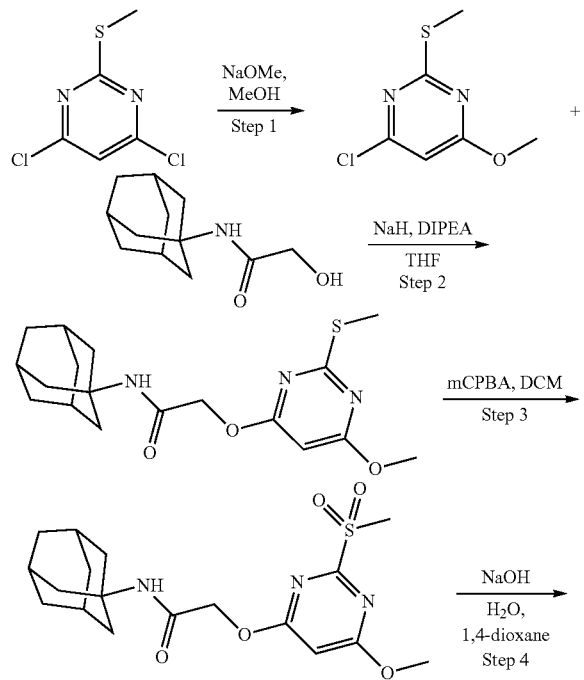

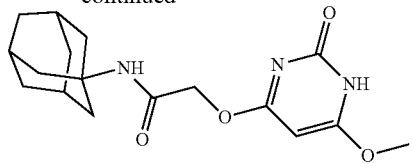

36 i. Step-1.

Synthesis of 4-chloro-6-methoxy-2-(methylthio)pyrimidine: Sodium methoxide (25% solution in MeOH) (1.29 mL, 5.64 mmol) was added to a solution of 4,6-dichloro-2-(methylthio)pyrimidine (1.00 g, 5.13 mmol) in anhydrous MeOH (18 mL). The reaction mixture was stirred at room temperature for 18 hrs. The solvent was evaporated and the residue was treated with H$_2$O and extracted with EtOAc (3×20 mL). The organic layers were collected, dried over anhydrous Na$_2$SO$_4$, filtered and evaporated to dryness under reduced pressure to yield the product. Yield: 849 mg (87%). $^1$H NMR (CDCl$_3$) δ 6.41 (s, 1H), 3.98 (s, 3H), 2.55 (s, 3H). ESIMS: m/z 191.0 [M+H]$^+$.

ii. Step-2.

Synthesis of N-(adamantan-1-yl)-2-((6-methoxy-2-(methylthio)pyrimidin-4-yl)oxy)acetamide: Sodium hydride (0.09 g, 2.36 mmol) was added to a solution of N-(1-adamantyl)-2-hydroxy-acetamide (0.33 g, 1.57 mmol) in anhydrous THF (10 mL) at 0° C. After stirring for 30 min at room temperature, 4-chloro-6-methoxy-2-(methylthio)pyrimidine (0.30 g, 1.57 mmol) and DIPEA (0.02 mL, 0.09 mmol) were added. The reaction mixture was further stirred at 40° C. for 18 hrs. The reaction mixture was treated with saturated aqueous NH$_4$Cl solution (10 mL) and extracted with EtOAc (3×20 mL). The organic layers were collected, dried over anhydrous Na$_2$SO$_4$, filtered and evaporated to dryness under reduced pressure to give a residue, which was purified on pre-packed Silica gel using 0-70% EtOAc in Hexanes (30 min). Yield: 154 mg (27%). $^1$H NMR (CDCl$_3$) δ 5.90 (s, 1H), 5.80 (s, 1H), 4.69 (s, 2H), 3.95 (s, 3H), 2.52 (s, 3H), 2.08 (s, 3H), 2.03-1.97 (m, 6H), 1.71-1.66 (m, 6H). ESIMS: m/z 364.2 [M+H]$^+$.

iii. Step-3.

Synthesis of N-(adamantan-1-yl)-2-((6-methoxy-2-(methylsulfonyl)pyrimidin-4-yl)oxy)acetamide: mCPBA (0.20 g, 0.89 mmol) was added to a solution of N-(adamantan-1-yl)-2-((6-methoxy-2-(methylthio)pyrimidin-4-yl)oxy)acetamide (0.15 g, 0.42 mmol) in anhydrous DCM (11 mL) at 0° C. The reaction mixture was then stirred at room temperature for 18 hr. The reaction mixture was diluted with DCM (11 mL), washed with 5% aqueous Na$_2$S$_2$O$_3$ solution (3×11 mL) and 5% aqueous Na$_2$CO$_3$ solution (3×11 mL). The reaction mixture then washed repeatedly with H$_2$O until the aqueous washings had reached to pH~ 7. The undissolved solids were filtered off. The filtrate was dried over Na$_2$SO$_4$, filtered and evaporated to dryness under reduced pressure to give a residue, which was used for the next step without further purification.

iv. Step-4.

Synthesis of N-(adamantan-1-yl)-2-((6-methoxy-2-oxo-1,2-dihydropyrimidin-4-yl)oxy)acetamide (36): Sodium hydroxide (2N aqueous solution) (0.42 mL, 0.84 mmol) was added to a solution of N-(adamantan-1-yl)-2-((6-methoxy-2-(methylsulfonyl)pyrimidin-4-yl)oxy)acetamide (0.17 g, 0.42 mmol) in anhydrous 1,4-dioxane (12 mL). The reaction mixture was then stirred at 60° C. for 18 hr. The solvent was removed and the residue was dissolved in acetonitrile (6 mL), H₂O (6 mL) and 1N HCl (1.2 mL) and stirred for 10 min. The mixture was extracted with EtOAc (3×10 mL). The organic layers were collected, dried over Na₂SO₄, filtered and evaporated to dryness under reduced pressure to give a residue, which was purified on pre-packed Silica gel column using 0-10% MeOH in DCM (20 min). Yield: 64 mg (45%). ¹H NMR (CD₃OD) δ 5.59 (s, 1H), 4.66 (s, 2H), 4.57 (s, 1H), 3.93 (s, 3H), 2.09-2.03 (m, 9H), 1.76-1.68 (m, 6H). HR-ESIMS: m/z 334.1767 [M+H]⁺ calcd. for C₁₇H₂₄N₃O₄, found 334.1754. HPLC purity: 96% (Retention Time=10.1 min).

l. Synthetic Procedure XI

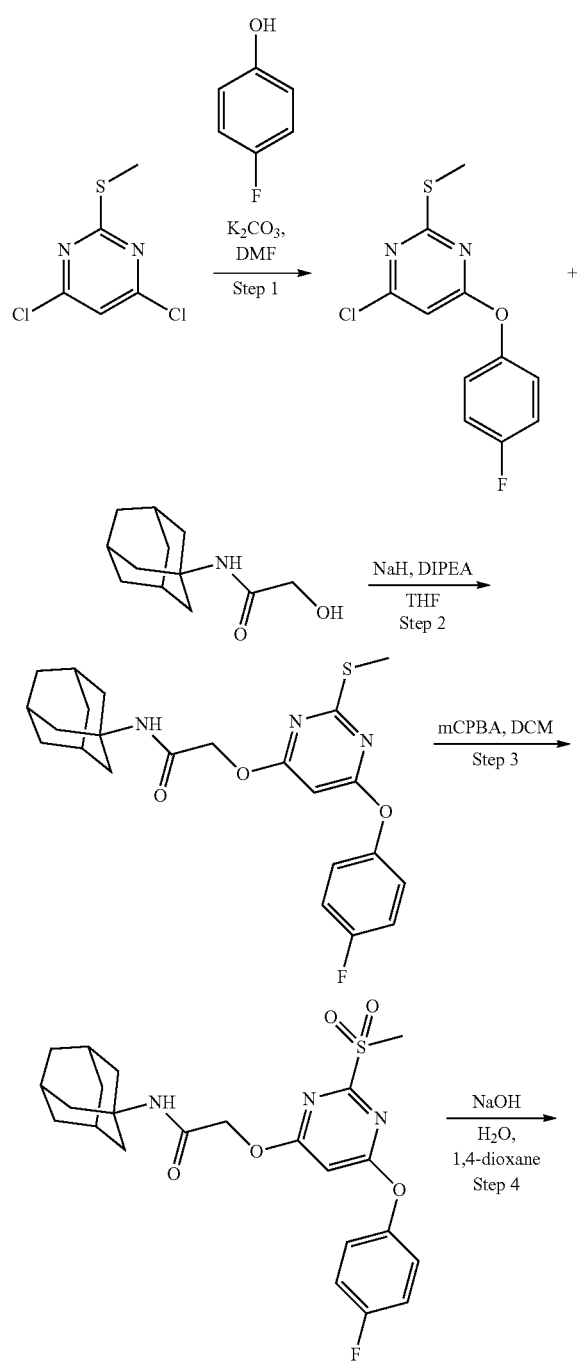

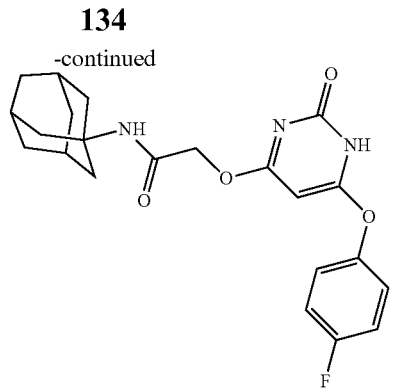

37 i. Step-1.

Synthesis of 4-chloro-6-(4-fluorophenoxy)-2-(methylthio)pyrimidine: 4-Fluoro-phenol (0.50 g, 4.46 mmol) and potassium carbonate (0.92 g, 6.69 mmol) were added at room temperature to a solution of 4,6-dichloro-2-(methylthio)pyrimidine (0.87 g, 4.46 mmol) in anhydrous DMF (8 mL). The reaction mixture was then stirred at 80° C. for 18 hrs. After cooling to room temperature, the reaction mixture was treated with H₂O (8 mL) and extracted with DCM (3×10 mL). The organic layers were collected, dried over anhydrous Na₂SO₄, filtered and evaporated to dryness under reduced pressure to give a residue, which was purified on pre-packed Silica gel using 0-70% EtOAc in Hexanes (30 min). Yield: 760 mg (63%). ¹H NMR (CDCl₃) δ 7.10 (d, J=6.3 Hz, 4H), 6.51 (s, 1H), 2.37 (s, 3H). ESIMS: m/z 271.0 [M+H]⁺.

ii. Step-2.

Synthesis of N-(adamantan-1-yl)-2-((6-(4-fluorophenoxy)-2-(methylthio)pyrimidin-4-yl)oxy)acetamide:

Sodium hydride (0.04 g, 1.11 mmol) was added to a solution of N-(1-adamantyl)-2-hydroxy-acetamide (0.15 g, 0.74 mmol) in anhydrous THF (5 mL) at 0° C. After stirring for 30 min at room temperature, 4-chloro-6-(4-fluorophenoxy)-2-(methylthio)pyrimidine (0.20 g, 0.74 mmol) and DIPEA (0.01 mL, 0.04 mmol) were added. The reaction mixture was then stirred at 40° C. for 18 hrs. The reaction mixture was treated with saturated aqueous NH₄Cl solution (10 mL) and extracted with EtOAc (3×20 mL). The organic layers were collected, dried over anhydrous Na₂SO₄, filtered and evaporated to dryness under reduced pressure to give a residue, which was purified on pre-packed Silica gel using 0-70% EtOAc in Hexanes (30 min). Yield: 91 mg (28%). ¹H NMR (CDCl₃) δ 7.10 (d, J=6.9 Hz, 4H), 5.85 (s, 1H), 5.83 (s, 1H), 4.71 (s, 2H), 2.40 (s, 3H), 2.09 (s, 3H), 2.02-2.00 (m, 6H), 1.69-1.67 (m, 6H). ESIMS: m/z 444.2 [M+H]⁺.

iii. Step-3.

Synthesis of N-(adamantan-1-yl)-2-((6-(4-fluorophenoxy)-2-(methylsulfonyl)pyrimidin-4-yl)oxy)acetamide:

mCPBA (0.10 g, 0.43 mmol) was added to a solution of N-(adamantan-1-yl)-2-((6-(4-fluorophenoxy)-2-(methylthio)pyrimidin-4-yl)oxy)acetamide (0.09 g, 0.21 mmol) in anhydrous DCM (5 mL) at 0° C. The reaction mixture was then stirred at room temperature for 18 hr. The reaction mixture was diluted with DCM (5 mL), washed with 5% aqueous Na₂S₂O₃ solution (3×5 mL) and 5% aqueous Na₂CO₃ solution (3×5 mL). The reaction mixture was then washed repeatedly with H₂O until the aqueous washings had reached to pH~7. The undissolved solids were filtered off. The filtrate was dried over Na₂SO₄, filtered and evaporated to dryness under reduced pressure to give a residue, which was used for the next step without further purification.

iv. Step-4.

Synthesis of N-(adamantan-1-yl)-2-((6-(4-fluorophenoxy)-2-oxo-1,2-dihydropyrimidin-4-yl)oxy)acetamide (37): Sodium hydroxide (2N aqueous solution) (0.20 mL, 0.41 mmol) was added to a solution of N-(adamantan-1-yl)-2-((6-(4-fluorophenoxy)-2-(methylsulfonyl)pyrimidin-4-yl)oxy)acetamide (0.10 g, 0.20 mmol) in anhydrous 1,4-dioxane (6 mL). The reaction mixture was then stirred at 60° C. for 18 hr. The solvent was removed and the residue was dissolved in acetonitrile (3 mL), H$_2$O (3 mL) and 1N HCl (0.6 mL) and stirred for 10 min. The mixture was extracted with EtOAc (3×10 mL). The organic layers were collected, dried over Na$_2$SO$_4$, filtered and evaporated to dryness under reduced pressure to give a residue, which was purified on pre-packed Silica gel column using 0-10% MeOH in DCM (20 min). Yield: 20 mg (24%). $^1$H NMR (CDCl$_3$) δ 7.14 (d, J=6.1 Hz, 4H), 5.77 (s, 1H), 5.09 (s, 1H), 4.69 (s, 2H), 2.06 (s, 3H), 2.02-1.96 (m, 6H), 1.69-1.64 (m, 6H). HR-ESIMS: m/z 414.1829 [M+H]$^+$ calcd. for C$_{22}$H$_{25}$FN$_3$O$_4$, found 414.1832. HPLC purity: 100% (Retention Time=13.4 min).

m. Synthetic Procedure XII

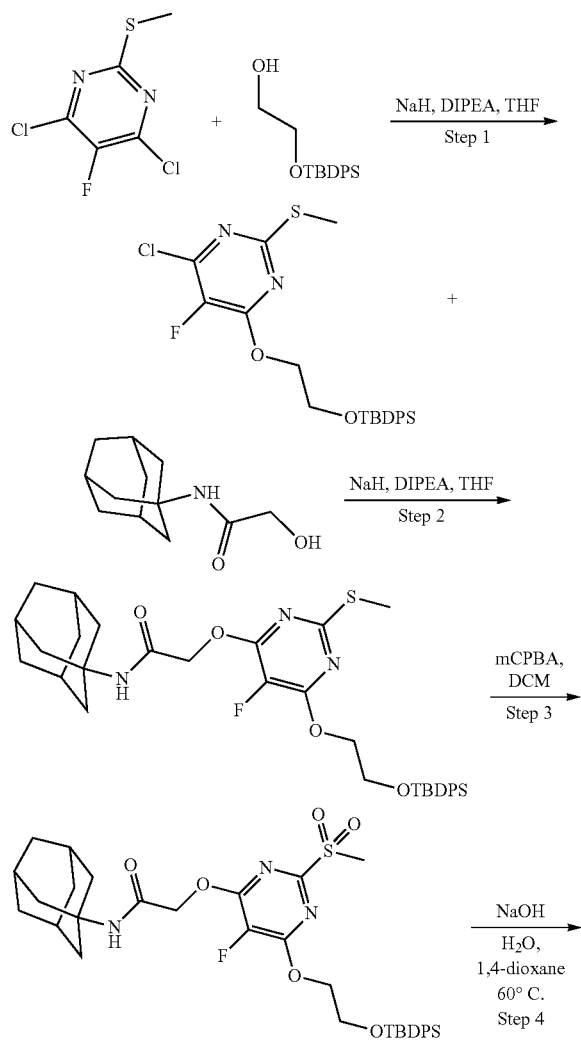

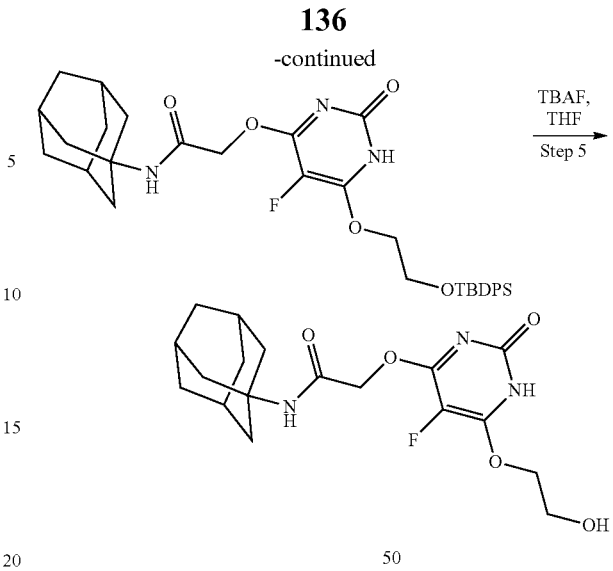

i. Step-1.

Synthesis of 4-(2-((tert-butyldiphenylsilyl)oxy)ethoxy)-6-chloro-5-fluoro-2-(methylthio)pyrimidine: Sodium hydride (0.08 g, 2.11 mmol) was added to a solution of 2-((tert-butyldiphenylsilyl)oxy)ethan-1-ol (0.42 g, 1.41 mmol) in anhydrous THF (7 mL) at 0° C. After stirring for 30 min at room temperature, 4,6-dichloro-5-fluoro-2-(methylthio)pyrimidine (0.30 g, 1.41 mmol) and DIPEA (0.01 mL, 0.08 mmol) were added. The reaction mixture was then stirred at rt for 18 hrs. The reaction mixture was treated with saturated aqueous NH$_4$Cl (10 mL) and extracted with EtOAc (3×20 mL). The organic layer was collected, dried over anhydrous Na$_2$SO$_4$, filtered and evaporated to dryness under reduced pressure to give a residue, which was purified on using 0-70% EtOAc in Hexanes (30 min). Yield: 441 mg (66%). $^1$H NMR (CDCl$_3$) δ 7.68-7.65 (m, 4H), 7.39-7.35 (m, 6H), 4.60-4.54 (m, 2H), 4.01-3.98 (m, 2H), 2.49 (s, 3H), 1.04 (s, 9H). ESIMS: m/z 478.0 [M+H]$^+$.

ii. Step-2.

Synthesis of N-(adamantan-1-yl)-2-((6-(2-((tert-butyldiphenylsilyl)oxy) ethoxy)-5-fluoro-2-(methylthio)pyrimidin-4-yl)oxy)acetamide: Sodium hydride (0.06 g, 1.39 mmol) was added to a solution of N-(adamantan-1-yl)-2-hydroxyacetamide (0.19 g, 0.92 mmol) in anhydrous THF (5 mL) at 0° C. After stirring for 30 min at room temperature, 4-(2-((tert-butyldiphenylsilyl)oxy)ethoxy)-6-chloro-5-fluoro-2-(methylthio)pyrimidine (0.44 g, 0.92 mmol) from Step-1 and DIPEA (0.01 mL, 0.06 mmol) were added. The reaction mixture was then stirred at rt for 18 hrs. The reaction mixture was treated with saturated aqueous NH$_4$Cl (10 mL) and extracted with EtOAc (3×20 mL). The organic layer was collected, dried over anhydrous Na$_2$SO$_4$, filtered and evaporated to dryness under reduced pressure to give a residue, which was purified on using 0-70% EtOAc in Hexanes (30 min). Yield: 212 mg (35%). $^1$H NMR (CDCl$_3$) δ 7.70-7.66 (m, 4H), 7.43-7.34 (m, 6H), 6.01 (s, 1H), 4.75 (s, 2H), 4.60-4.51 (m, 2H), 3.99 (t, J=4.9 Hz, 2H), 2.46 (s, 3H), 2.09 (s, 3H), 2.04-2.02 (m, 6H), 1.70-1.68 (m, 6H), 1.03 (s, 9H). ESIMS: m/z 649.9 [M+H]$^+$.

iii. Step-3.

Synthesis of N-(adamantan-1-yl)-2-((6-(2-((tert-butyldiphenylsilyl)oxy) ethoxy)-5-fluoro-2-(methylsulfonyl)pyrimidin-4-yl)oxy)acetamide: mCPBA (0.16 g, 0.72 mmol) was added to a solution of N-(adamantan-1-yl)-2-((6-(2-((tert-butyldiphenylsilyl)oxy) ethoxy)-5-fluoro-2-(methylthio)pyrimidin-4-yl)oxy)acetamide (0.21 g, 0.33 mmol) from Step-2 in anhydrous DCM (10 mL) at 0° C. The reaction mixture was then stirred at room temperature for 18 hr. The reaction mixture was diluted with DCM (10 mL), washed with 5% aqueous Na$_2$S$_2$O$_3$ solution (3×10 ml) and 5% aqueous Na$_2$CO$_3$ (3×10 mL) solution. The reaction mixture then washed repeatedly with H$_2$O until the aqueous washings had reached to pH~7. The undissolved solids were filtered off. The filtrate was dried over Na$_2$SO$_4$, filtered and evaporated to dryness under reduced pressure to give a residue, which was used for the next step without further purification.

iv. Step-4.

Synthesis of N-(adamantan-1-yl)-2-((6-(2-((tert-butyldiphenylsilyl)oxy) ethoxy)-5-fluoro-2-oxo-1,2-dihydropyrimidin-4-yl)oxy)acetamide: To a solution of N-(adamantan-1-yl)-2-((6-(2-((tert-butyldiphenylsilyl)oxy)ethoxy)-5-fluoro-2-(methylsulfonyl)pyrimidin-4-yl)oxy)acetamide (0.22 g, 0.32 mmol) from Step-3 in anhydrous 1,4-dioxane (7 mL) was added 2N aqueous sodium hydroxide (0.32 mL, 0.65 mmol). The reaction mixture was then stirred at 60° C. for 18 hr. The solvent was removed and the residue was dissolved in acetonitrile (4 mL), H$_2$O (4 mL) and 1N HCl (0.7 mL) and stirred for 10 min. The mixture was extracted with EtOAc (3×20 mL). The organic layer was collected, dried over Na$_2$SO$_4$, filtered and evaporated to dryness under reduced pressure to give a residue, which was purified on using 0-10% MeOH in DCM (20 min). Yield: 148 mg (74%). $^1$H NMR (CDCl$_3$) δ 7.72-7.65 (m, 4H), 7.46-7.33 (m, 6H), 6.02 (s, 1H), 4.71 (s, 2H), 4.53 (t, J=4.9 Hz, 2H), 4.02-3.95 (m, 2H), 2.09 (s, 3H), 2.03-2.01 (m, 6H), 1.69-1.68 (m, 6H), 1.04 (s, 9H). ESIMS: m/z 619.9 [M+H]$^+$.

v. Step-5.

Synthesis of N-(adamantan-1-yl)-2-((5-fluoro-6-(2-hydroxyethoxy)-2-oxo-1,2-dihydropyrimidin-4-yl)oxy)acetamide (50): TBAF (1M solution in THF) (0.48 mL, 0.48 mmol) was added to a solution of N-(adamantan-1-yl)-2-((6-(2-((tert-butyldiphenylsilyl)oxy)ethoxy)-5-fluoro-2-oxo-1,2-dihydropyrimidin-4-yl)oxy)acetamide (0.15 g, 0.24 mmol) from Step-4 in anhydrous THF (5 mL) at 0° C. The reaction mixture was then stirred at room temperature for 18 hrs. The reaction mixture was concentrated and purified on Silica gel using 0-10% MeOH in DCM (20 min). Yield: 35 mg (36%). $^1$H NMR (CDCl$_3$): δ 6.10 (s, 1H), 4.75 (s, 2H), 4.63-4.49 (m, 2H), 3.97 (t, J=4.4 Hz, 2H), 2.09 (s, 3H), 2.05-1.98 (m, 6H), 1.74-1.64 (m, 6H). HR-ESIMS: m/z 382.17728 [M+H]$^+$ calcd. for C$_{18}$H$_{25}$FN$_3$O$_5$, found 382.17700. HPLC purity: 95% (Retention Time=11.8 min).

n. Synthetic Procedure XIII

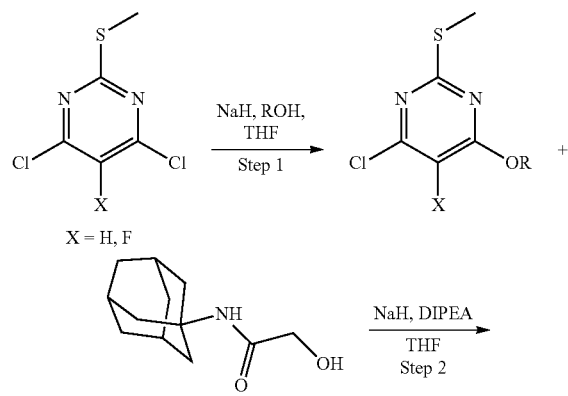

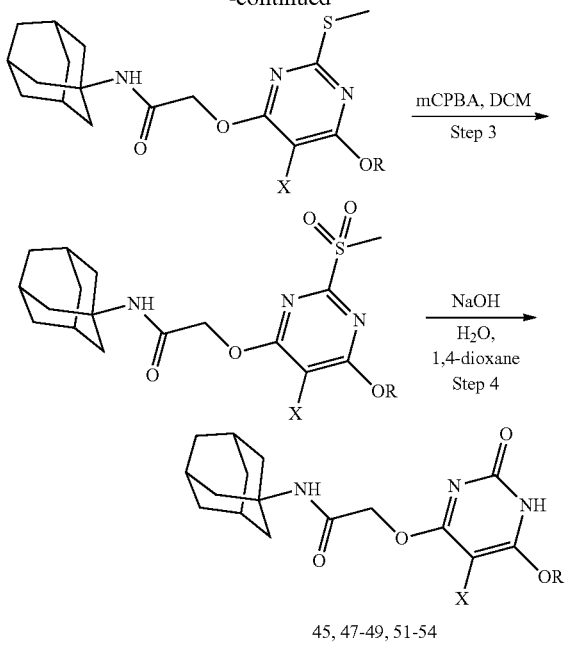

45, 47-49, 51-54 i. Step 1.

General Procedure: Sodium hydride (1.1 mmol) was added to a solution of corresponding alcohol (1 mmol) in anhydrous THF (2 mL) at rt. After stirring for 30 min at rt, corresponding methylthio-pyrimidine (1 mmol) was added. The reaction mixture was then stirred at rt for 18 hrs. The solvent is evaporated and the residue was treated with H$_2$O (5 mL) and extracted with EtOAc (3×5 mL). The organic layer was collected, dried over anhydrous Na$_2$SO$_4$, filtered and evaporated to dryness under reduced pressure to give a residue, which was purified on ISCO to yield the product.

(i) 4-Chloro-6-Isopropoxy-2-(Methylthio)Pyrimidine

Purification on pre-packed Silica gel column on ISCO using 0-70% EtOAc in Hexanes (30 min). Yield: 478 mg (85%). H NMR (CDCl$_3$) δ 6.34 (s, 1H), 5.37 (dt, J=12.8, 6.2 Hz, 1H), 2.53 (s, 3H), 1.34 (d, J=6.2 Hz, 6H). ESIMS: in/z 219.0 [M+H]$^+$.

(ii) 4-Chloro-6-(3,3-Difluorocyclobutoxy)-2-(Methylthio)Pyrimidine

Purification on pre-packed Silica gel column on ISCO using 0-70% EtOAc in Hexanes (30 min). Yield: 641 mg (94%). H NMR (CDCl$_3$) δ 6.44 (s, 1H), 5.22-5.12 (m, 1H), 3.17-3.06 (m, 2H), 2.82-2.68 (m, 2H), 2.53 (s, 3H). ESIMS: m/z 267.0 [M+H]$^+$.

(iii) 4-Chloro-6-Cyclopropoxy-2-(Methylthio)Pyrimidine

Purification on pre-packed Silica gel column on ISCO using 0-70% EtOAc in Hexanes (30 min). Yield: 529 mg (95%). $^1$H NMR (CDCl$_3$) δ 6.44 (s, 1H), 4.33-4.23 (m, 1H), 2.55 (s, 3H), 0.83-0.79 (m, 4H). ESIMS: m/z 216.9 [M+H]$^+$.

(iv) 4-Chloro-6-(2-Methoxyethoxy)-2-(Methylthio) Pyrimidine

Purification on pre-packed Silica gel column on ISCO using 0-70% EtOAc in Hexanes (30 min). Yield: 321 mg (53%). ¹H NMR (CDCl₃) δ 6.46 (s, 1H), 4.57-4.48 (m, 2H), 3.76-3.67 (m, 2H), 3.41 (s, 3H), 2.53 (s, 3H). ESIMS: m/z 234.9 [M+H]⁺.

(v) 4-Chloro-2-(Methylthio)-6-(Neopentyloxy)Pyrimidine

Purification on pre-packed Silica gel column on ISCO using 0-70% EtOAc in Hexanes (30 min). Yield: 559 mg (88%). ¹H NMR (CDCl₃) δ 6.43 (s, 1H), 4.03 (s, 2H), 2.54 (s, 3H), 1.00 (s, 9H). ESIMS: m/z 246.9 [M+H]⁺.

(vi) 3-((6-Chloro-2-(Methylthio)Pyrimidin-4-Yl)Oxy)-2,2-Dimethylpropanenitrile Purification on pre-packed Silica gel column on ISCO using 0-70% EtOAc in Hexanes (30 min). Yield: 300 mg (45%). ¹H NMR (CDCl₃) δ 6.54 (s, 1H), 4.32 (s, 2H), 2.55 (s, 3H), 1.46 (s, 6H). ESIMS: m/z 258.0 [M+H]⁺.

(vii) 4-Chloro-2-(Methylthio)-6-(Oxetan-3-Yloxy)Pyrimidine

Purification on pre-packed Silica gel column on ISCO using 0-70% EtOAc in Hexanes (30 min). Yield: 315 mg (53%). H NMR (CDCl₃) δ 6.48 (s, 1H), 5.70-5.60 (m, 1H), 4.99-4.91 (m, 2H), 4.72 (dd, J=8.6, 5.3 Hz, 2H), 2.50 (s, 3H). ESIMS: m/z 232.9 [M+H]⁺.

(viii) 4-Chloro-5-Fluoro-6-Isopropoxy-2-(Methylthio)Pyrimidine

Purification on pre-packed Silica gel column on ISCO using 0-70% EtOAc in Hexanes (30 min). Yield: 193 mg (87%). H NMR (CDCl₃) δ 5.46-5.37 (m, 1H), 2.52 (s, 3H), 1.40 (d, J=6.2 Hz, 6H). ESIMS: m/z 237.0 [M+H]⁺.

ii. STEP 2.

General Procedure: Sodium hydride (1.5 mmol) was added to a solution of N-(adamantan-1-yl)-2-hydroxyacetamide (1.5 mmol) in anhydrous THF (4 mL) at 0° C. After stirring for 30 min at rt, the product from Step-1 (1 mmol) and DIPEA (0.06 mmol) were added. The reaction mixture was then stirred at rt for 18 hrs. The reaction mixture was treated with NH₄Cl (10 mL, saturated solution in H₂O) and extracted with EtOAc (3×10 mL). The organic layer was collected, dried over anhydrous Na₂SO₄, filtered and evaporated to dryness under reduced pressure to give a residue, which was purified on ISCO to yield the product.

(i) N-(Adamantan-1-Yl)-2-((6-Isopropoxy-2-(Methylthio)Pyrimidin-4-Yl)Oxy)Acetamide Purification on pre-packed Silica gel column on ISCO using 0-70% EtOAc in Hexanes (30 min). Yield: 171 mg (38%). ¹H NMR (CDCl₃) δ 5.93 (s, 1H), 5.74 (s, 1H), 5.42-5.26 (m, 1H), 4.68 (s, 2H), 2.51 (s, 3H), 2.08 (s, 3H), 2.04-1.98 (m, 6H), 1.70-1.65 (m, 6H), 1.33 (d, J=6.2 Hz, 6H). ESIMS: m/z 392.1 [M+H]⁺.

(ii) N-(Adamantan-1-Yl)-2-((6-(3,3-Difluorocyclobutoxy)-2-(Methylthio)Pyrimidin-4-Yl)Oxy)Acetamide Purification on pre-packed Silica gel column on ISCO using 0-70% EtOAc in Hexanes (30 min). Yield: 180 mg (27%). ¹H NMR (CDCl₃) δ 5.88 (s, 1H), 5.82 (s, 1H), 5.23-5.08 (m, 1H), 4.69 (s, 2H), 3.15-3.04 (m, 2H), 2.81-2.67 (m, 2H), 2.50 (s, 3H), 2.08 (s, 3H), 2.02-2.00 (m, 6H), 1.70-1.67 (m, 6H). ESIMS: m/z 440.0 [M+H]⁺.

(iii) N-(Adamantan-1-Yl)-2-((6-Cyclopropoxy-2-(Methylthio)Pyrimidin-4-Yl)Oxy)Acetamide Purification on pre-packed Silica gel column on ISCO using 0-70% EtOAc in Hexanes (30 min). Yield: 231 mg (43%). ¹H NMR (CDCl₃) δ 5.91 (s, 1H), 4.70 (s, 2H), 4.17 (p, J=5.0 Hz, 1H), 2.52 (s, 3H), 2.09 (s, 3H), 2.03-1.99 (m, 6H), 1.70-1.67 (m, 6H), 0.84-0.76 (m, 4H). ESIMS: m/z 390.0 [M+H]⁺.

(iv) N-(Adamantan-1-Yl)-2-((6-(2-Methoxyethoxy)-2-(Methylthio)Pyrimidin-4-Yl)Oxy)Acetamide Purification on pre-packed Silica gel column on ISCO using 0-70% EtOAc in Hexanes (30 min). Yield: 239 mg (43%). ¹H NMR (CDCl₃) δ 5.90 (s, 1H), 5.86 (s, 1H), 4.69 (s, 2H), 4.53-4.48 (m, 2H), 3.74-3.67 (m, 2H), 3.42 (s, 3H), 2.51 (s, 3H), 2.08 (s, 3H), 2.02-1.98 (m, 6H), 1.69-1.66 (m, 6H). ESIMS: m/z 408.0 [M+H]⁺.

(v) N-(Adamantan-1-Yl)-2-((2-(Methylthio)-6-(Neopentyloxy)Pyrimidin-4-Yl)Oxy)Acetamide Purification on pre-packed Silica gel column on ISCO using 0-70% EtOAc in Hexanes (30 min). Yield: 235 mg (46%). ¹H NMR (CDCl₃) δ 5.83 (s, 1H), 4.69 (s, 2H), 4.02 (s, 2H), 2.53 (s, 3H), 2.09 (s, 3H), 2.04-2.02 (m, 6H), 1.69-1.68 (m, 6H), 1.00 (s, 9H). ESIMS: m/z 420.0 [M+H]⁺.

(vi) N-(Adamantan-1-Yl)-2-((6-(2-Cyano-2-Methylpropoxy)-2-(Methylthio)Pyrimidin-4-Yl)Oxy)Acetamide Purification on pre-packed Silica gel column on ISCO using 0-70% EtOAc in Hexanes (30 min). Yield: 203 mg (41%). ¹H NMR (CDCl₃) δ 5.93 (s, 1H), 5.91 (s, 1H), 4.72 (s, 2H), 4.31 (s, 2H), 2.52 (s, 3H), 2.09 (s, 3H), 2.02-1.99 (m, 6H), 1.70-1.68 (m, 6H), 1.45 (s, 6H). ESIMS: m/z 431.0 [M+H]⁺.

(vii) N-(Adamantan-1-Yl)-2-((2-(Methylthio)-6-(Oxetan-3-Yloxy)Pyrimidin-4-Yl)Oxy)Acetamide Purification on pre-packed Silica gel column on ISCO using 0-70% EtOAc in Hexanes (30 min). Yield: 272 mg (50%). ¹H NMR (CD₃OD) δ 5.97 (s, 1H), 5.62 (p, J=5.8 Hz, 1H), 4.98-4.92 (m, 2H), 4.70-4.65 (m, 4H), 2.47 (s, 3H), 2.08-2.02 (m, 9H), 1.73-1.69 (m, 6H). ESIMS: m/z 406.0 [M+H]⁺.

(viii) N-(Adamantan-1-Yl)-2-((5-Fluoro-6-Isopropoxy-2-(Methylthio)Pyrimidin-4-Yl)Oxy)Acetamide Purification on pre-packed Silica gel column on ISCO using 0-70% EtOAc in Hexanes (30 min). Yield: 216 mg (65%). ¹H NMR (CDCl₃) δ 6.00 (s, 1H), 5.45-5.34 (m, 1H), 4.74 (s, 2H), 2.48 (s, 3H), 2.09 (s, 3H), 2.03-2.02 (m, 6H), 1.70-1.68 (m, 6H), 1.39 (d, J=6.2 Hz, 6H). ESIMS: m/z 410.2 [M+H]⁺.

iii. Step 3.

General Procedure: mCPBA (2.2 mmol) was added to a solution of the product from Step-2 (1 mmol) in anhydrous DCM (20 mL) at 0° C. The reaction mixture was then stirred at rt for 18 hr. The reaction mixture was diluted with DCM (20 mL), washed with $Na_2S_2O_3$ (5% solution in $H_2O$, 3×20 mL) and $Na_2CO_3$ (5% solution in $H_2O$, 3×20 mL). The reaction mixture then washed repeatedly with $H_2O$ until the aqueous washings had reached to pH~7. The undissolved solids were filtered off. The filtrate was dried over $Na_2SO_4$, filtered and evaporated to dryness under reduced pressure to give a residue, which was used for the next step without further purification.

iv. Step 4.

General Procedure: Sodium hydroxide (2 N solution in water) (2 mmol) was added to a solution of the product from Step-3 (1 mmol) in anhydrous 1,4-dioxane (20 mL). The reaction mixture was then stirred at rt for 18 hr. The solvent was removed and the residue was dissolved in acetonitrile (10 mL), $H_2O$ (10 ml) and HCl (1N, 2 mL) and stirred for 10 min. The mixture was extracted with EtOAc (3×20 mL). The organic layer was collected, dried over $Na_2SO_4$, filtered and evaporated to dryness under reduced pressure to give a residue, which was purified on ISCO to yield the product.

(i) N-(Adamantan-1-Yl)-2-((6-Isopropoxy-2-Oxo-1,2-Dihydropyrimidin-4-Yl)Oxy)Acetamide (45)

Purification on pre-packed Silica gel column on ISCO using 0-10% MeOH in DCM (20 min). Yield: 86 mg (53%). 1H NMR ($CDCl_3$): δ 5.96 (s, 1H), 5.32 (s, 1H), 4.94-4.83 (m, 1H), 4.66 (s, 2H), 2.09 (s, 3H), 2.05-2.02 (m, 6H), 1.70-1.67 (m, 6H), 1.39 (d, J=6.0 Hz, 6H). HR-ESIMS: m/z 362.20743 $[M+H]^+$ calcd. for $C_{19}H_{28}N_3O_4$, found 362.20710. HPLC purity: 97% (Retention Time=11.7 min).

(ii) N-(Adamantan-1-Yl)-2-((6-(3,3-Difluorocyclobutoxy)-2-Oxo-1,2-Dihydropyrimidin-4-Yl)Oxy)Acetamide (47)

Purification on pre-packed Silica gel column on ISCO using 0-10% MeOH in DCM (20 min). Yield: 35 mg (40%). $^1$H NMR (DMSO-$d_6$): δ 7.38 (s, 1H), 5.51 (s, 1H), 5.18-4.82 (m, 1H), 4.56 (s, 2H), 3.21-3.06 (m, 2H), 2.77-2.62 (m, 2H), 1.99 (s, 3H), 1.92-1.87 (m, 6H), 1.64-1.55 (m, 6H). HR-ESIMS: m/z 410.18859 $[M+H]^+$ calcd. for $C_{20}H_{26}F_2N_3O_4$, found 410.18760. HPLC purity: 100% (Retention Time=12.6 min).

(iii) N-(Adamantan-1-Yl)-2-((6-Cyclopropoxy-2-Oxo-1,2-Dihydropyrimidin-4-Yl)Oxy)Acetamide (48)

Purification on pre-packed Silica gel column on ISCO using 0-10% MeOH in DCM (20 min). Yield: 106 mg (50%). $^1$H NMR ($CDCl_3$): δ 5.93 (s, 1H), 5.66 (s, 1H), 4.74 (s, 2H), 4.04-3.92 (m, 1H), 2.09 (s, 3H), 2.05-2.02 (m, 6H), 1.70-1.67 (m, 6H), 0.94-0.85 (m, 4H). HR-ESIMS: m/z 360.19178 $[M+H]^+$ calcd. for $C_{19}H_{26}N_3O_4$, found 360.19196. HPLC purity: 100% (Retention Time=11.6 min).

(iv) N-(Adamantan-1-Yl)-2-((6-(2-Methoxyethoxy)-2-Oxo-1,2-Dihydropyrimidin-4-Yl)Oxy)Acetamide (49)

Purification on pre-packed Silica gel column on ISCO using 0-10% MeOH in DCM (20 min). Yield: 24 mg (28%). $^1$H NMR ($CDCl_3$): δ 6.05 (s, 1H), 5.40 (s, 1H), 4.58 (s, 2H), 4.46-4.32 (m, 2H), 3.78-3.62 (m, 2H), 3.41 (s, 3H), 2.08 (s, 3H), 2.06-1.96 (m, 6H), 1.77-1.60 (m, 6H). HR-ESIMS: m/z 378.20235 $[M+H]^+$ calcd. for $C_{19}H_{28}N_3O_5$, found 378.20258. HPLC purity: 100% (Retention Time=10.6 min).

(v) N-(Adamantan-1-Yl)-2-((6-(Neopentyloxy)-2-Oxo-1,2-Dihydropyrimidin-4-Yl)Oxy)Acetamide (51)

Purification on pre-packed Silica gel column on ISCO using 0-10% MeOH in DCM (20 min). Yield: 46 mg (21%). $^1$H NMR ($CD_3OD$): δ 5.60 (s, 1H), 4.67 (s, 2H), 4.56 (s, 1H), 3.86 (s, 2H), 2.07-2.03 (m, 9H), 1.73-1.70 (m, 6H), 1.03 (s, 9H). HR-ESIMS: m/z 390.23873 $[M+H]^+$ calcd. for $C_{21}H_{32}N_3O_4$, found 390.23888. HPLC purity: 98% (Retention Time=13.7 min).

(vi) N-(Adamantan-1-Yl)-2-((6-(2-Cyano-2-Methylpropoxy)-2-Oxo-1,2-Dihydropyrimidin-4-Yl)Oxy)Acetamide (52)

Purification on pre-packed Silica gel column on ISCO using 0-10% MeOH in DCM (20 min). Yield: 75 mg (41%). H NMR ($CD_3OD$): δ 5.66 (s, 1H), 4.65 (s, 2H), 4.56 (s, 1H), 4.25 (s, 2H), 2.07-2.03 (m, 9H), 1.73-1.71 (m, 6H), 1.45 (s, 6H). HR-ESIMS: in/z 401.21833 $[M+H]^+$ calcd. for $C_{21}H_{29}N_4O_4$, found 401.21812. HPLC purity: 100% (Retention Time=12.0 min).

(vii) N-(Adamantan-1-Yl)-2-((6-(Oxetan-3-Yloxy)-2-Oxo-1,2-Dihydropyrimidin-4-Yl)Oxy)Acetamide (53)

Purification on pre-packed Silica gel column on ISCO using 0-10% MeOH in DCM (20 min). Yield: 15 mg (35%). H NMR ($CD_3OD$): δ 5.60-5.42 (m, 2H), 5.00-4.93 (m, 2H), 4.67 (dd, J=7.8, 4.9 Hz, 2H), 4.64 (s, 2H), 2.16-1.92 (m, 9H), 1.79-1.63 (m, 6H). HR-ESIMS: m/z 376.18670 $[M+H]^+$ calcd. for $C_{19}H_{26}N_3O_5$, found 376.18604. HPLC purity: 100% (Retention Time=10.8 min).

(viii) N-(Adamantan-1-Yl)-2-((5-Fluoro-6-Isopropoxy-2-Oxo-1,2-Dihydropyrimidin-4-Yl)Oxy)Acetamide (54)

Purification on pre-packed Silica gel column on ISCO using 0-10% MeOH in DCM (20 min). Yield: 10 mg (22%). 1H NMR ($CD_3OD$): δ 5.35-5.27 (m, 1H), 4.70 (s, 2H), 2.05-2.02 (m, 9H), 1.72-1.71 (m, 6H), 1.35 (d, J=6.2 Hz, 6H). HR-ESIMS: m/z 380.19801 $[M+H]^+$ calcd. for $C_{19}H_{27}FN_3O_4$, found 380.19757. HPLC purity: 95% (Retention Time=15.1 min).

o. Synthetic Procedure XIV

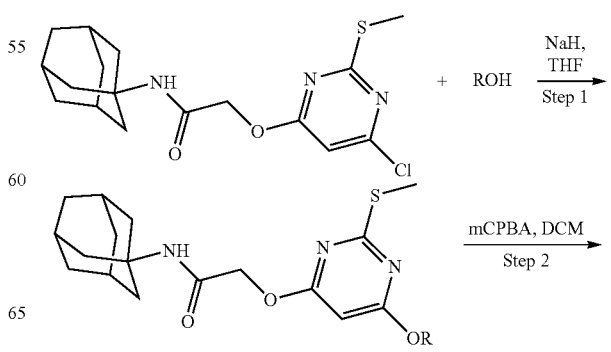

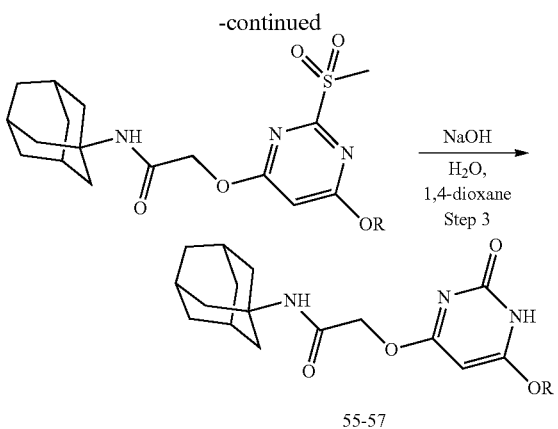

i. Step-1.

General Procedure: Sodium hydride (1.1 mmol) was added to a solution of corresponding alcohol (1 mmol) in anhydrous THF (2 mL) at rt. After stirring for 30 min at rt, N-(adamantan-1-yl)-2-((6-chloro-2-(methylthio)pyrimidin-4-yl)oxy)acetamide (1 mmol) was added. The reaction mixture was then stirred at rt for 18 hrs. The solvent is evaporated and the residue was treated with $H_2O$ (5 mL) and extracted with EtOAc (3×5 mL). The organic layer was collected, dried over anhydrous $Na_2SO_4$, filtered and evaporated to dryness under reduced pressure to give a residue, which was purified on ISCO to yield the product.

(i) N-((Adamantan-1-Yl)-2-((6-Ethoxy-2-(Methylthio)Pyrimidin-4-Yl)Oxy)Acetamide

Purification on pre-packed Silica gel column on ISCO using 0-70% EtOAc in Hexanes (30 min). Yield: 127 mg (62%). $^1H$ NMR ($CDCl_3$) δ 5.98 (s, 1H), 5.78 (s, 1H), 4.68 (s, 2H), 4.40 (q, J=7.1 Hz, 2H), 2.52 (s, 3H), 2.09 (s, 3H), 2.03-2.01 (m, 6H), 1.69-1.68 (m, 6H), 1.38 (t, J=7.1 Hz, 3H). ESIMS: m/z 378.2 $[M+H]^+$.

(ii) N-(Adamantan-1-Yl)-2-((6-(Sec-Butoxy)-2-(Methylthio)Pyrimidin-4-Yl)Oxy)Acetamide Purification on pre-packed Silica gel column on ISCO using 0-70% EtOAc in Hexanes (30 min). Yield: 45 mg (20%). $^1H$ NMR ($CDCl_3$) δ 6.18 (s, 1H), 5.76 (s, 1H), 4.75 (s, 2H), 4.69-4.60 (m, 1H), 2.49 (s, 3H), 2.09 (s, 3H), 2.04-2.02 (m, 6H), 1.70-1.68 (m, 6H), 1.35 (d, J=6.3 Hz, 3H), 1.33-1.27 (m, 2H), 0.96 (t, J=7.4 Hz, 3H). ESIMS: m/z 406.2 $[M+H]^+$.

(iii) N-(Adamantan-1-Yl)-2-((2-(Methylthio)-6-(2,2,2-Trifluoroethoxy)Pyrimidin-4-Yl)Oxy)Ace Tamide Purification on pre-packed Silica gel column on ISCO using 0-70% EtOAc in Hexanes (30 min). Yield: 82 mg (35%). $^1H$ NMR ($CDCl_3$) δ 5.95 (s, 1H), 4.78-4.75 (m, 2H), 4.72 (s, 2H), 2.52 (s, 3H), 2.09 (s, 3H), 2.02-2.00 (m, 6H), 1.69-1.68 (m, 6H). ESIMS: m/z 432.1 $[M+H]^+$.

ii. Step-2.

General Procedure: mCPBA (2.2 mmol) was added to a solution of the product from Step-1 (1 mmol) in anhydrous DCM (20 mL) at 0° C. The reaction mixture was then stirred at rt for 18 hr. The reaction mixture was diluted with DCM (20 mL), washed with $Na_2S_2O_3$ (5% solution in $H_2O$, 3×20 mL) and $Na_2CO_3$ (5% solution in $H_2O$, 3×20 mL). The reaction mixture then washed repeatedly with $H_2O$ until the aqueous washings had reached to pH 7. The undissolved solids were filtered off. The filtrate was dried over $Na_2SO_4$, filtered and evaporated to dryness under reduced pressure to give a residue, which was used for the next step without further purification.

iii. Step-3.

General Procedure: Sodium hydroxide (2 N solution in water) (2 mmol) was added to a solution of the product from Step-2 (1 mmol) in anhydrous 1,4-dioxane (20 mL). The reaction mixture was then stirred at rt for 18 hr. The solvent was removed and the residue was dissolved in acetonitrile (10 mL), $H_2O$ (10 ml) and HCl (1N, 2 mL) and stirred for 10 min. The mixture was extracted with EtOAc (3×20 mL). The organic layer was collected, dried over $Na_2SO_4$, filtered and evaporated to dryness under reduced pressure to give a residue, which was purified on ISCO to yield the product.

(i) N-(Adamantan-1-Yl)-2-((6-Ethoxy-2-Oxo-1,2-Dihydropyrimidin-4-Yl)Oxy)Acetamide (55)

Purification on pre-packed Silica gel column on ISCO using 0-10% MeOH in DCM (20 min). Yield: 68 mg (62%). 1H NMR ($CD_3OD$): δ 5.58 (s, 1H), 4.66 (s, 2H), 4.25 (q, J=7.1 Hz, 2H), 2.14-1.98 (m, 9H), 1.78-1.68 (m, 6H), 1.40 (t, J=7.0 Hz, 3H). HR-ESIMS: m/z 348.19178 $[M+H]^+$ calcd. for $C_{18}H_{26}N_3O_4$, found 348.19191. HPLC purity: 100% (Retention Time=11.4 min).

(ii) N-(adamantan-1-yl)-2-((6-(sec-butoxy)-2-oxo-1,2-dihydropyrimidin-4-yl)oxy)acetamide (56)

Purification on pre-packed Silica gel column on ISCO using 0-10% MeOH in DCM (20 min). Yield: 21 mg (51%). 1H NMR ($CD_3OD$): δ 5.59 (s, 1H), 4.76-4.54 (m, 3H), 2.08-2.03 (m, 9H), 1.77-1.68 (m, 8H), 1.34 (d, J=6.1 Hz, 3H), 0.97 (t, J=7.4 Hz, 3H). HR-ESIMS: m/z 376.22308 $[M+H]^+$ calcd. for $C_{20}H_{30}N_3O_4$, found 376.22322. HPLC purity: 100% (Retention Time=12.9 min).

(iii) N-(adamantan-1-yl)-2-((2-oxo-6-(2,2,2-trifluoroethoxy)-1,2-dihydropyrimidin-4-yl)oxy)acetamide (57)

Purification on pre-packed Silica gel column on ISCO using 0-10% MeOH in DCM (20 min). Yield: 46 mg (60%). $^1H$ NMR ($CDCl_3$): δ 6.01 (s, 1H), 5.59 (s, 1H), 4.78-4.70 (m, 2H), 4.54 (s, 2H), 2.09 (s, 3H), 2.04-2.02 (m, 6H), 1.70-1.68 (m, 6H). HR-ESIMS: m/z 402.16352 $[M+H]^+$ calcd. for $C_{18}H_{23}F_3N_3O_4$, found 402.16295. HPLC purity: 100% (Retention Time=13.1 min).

p. Synthetic Procedure XV

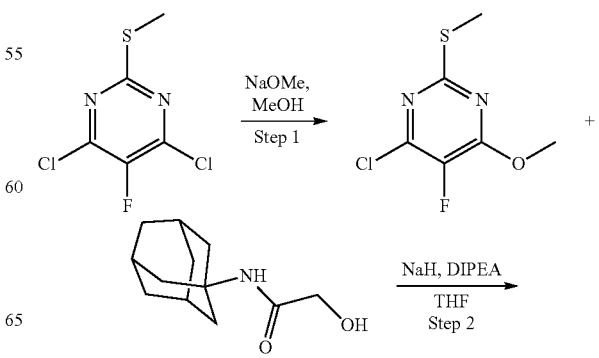

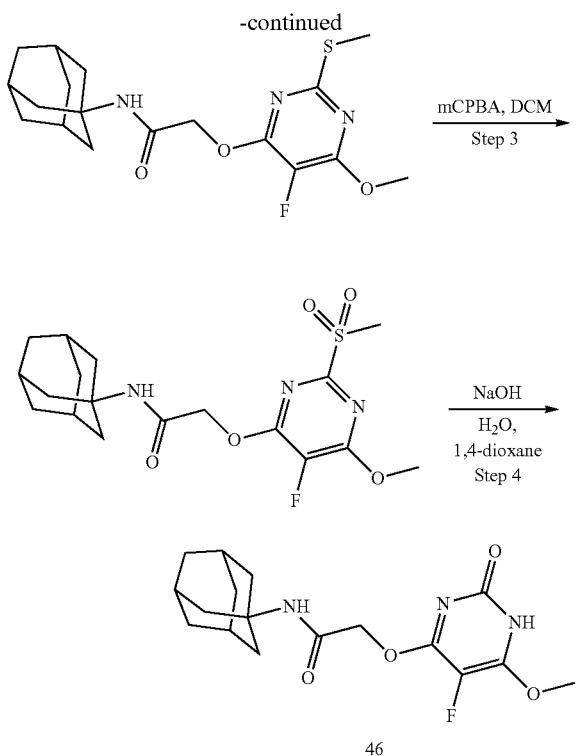

46 i. Step-1.

Synthesis of 4-chloro-5-fluoro-6-methoxy-2-(methylthio) pyrimidine: Sodium methoxide (0.5M solution in MeOH) (3.10 mL, 1.55 mmol) was added to a solution of 4,6-dichloro-5-fluoro-2-(methylthio)pyrimidine (0.30 g, 1.41 mmol) in anhydrous MeOH (5 mL). The reaction mixture was then stirred at rt for 18 hrs. The solvent is evaporated and the residue was treated with H$_2$O and extracted with EtOAc (3×20 mL). The organic layer was collected, dried over anhydrous Na$_2$SO$_4$, filtered and evaporated to dryness under reduced pressure to yield the product. Yield: 245 mg (83%). $^1$H NMR (CDCl$_3$) δ 4.07 (s, 3H), 2.54 (s, 3H). ESIMS: m/z 209.0 [M+H]$^+$.

ii. Step-2.

Synthesis of N-(adamantan-1-yl)-2-((5-fluoro-6-methoxy-2-(methylthio)pyrimidin-4-yl)oxy)acetamide: Sodium hydride (0.07 g, 1.76 mmol) was added to a solution of N-(1-adamantyl)-2-hydroxy-acetamide (0.25 g, 1.17 mmol) in anhydrous THF (5 mL) at 0° C. After stirring for 30 min at rt, 4-chloro-5-fluoro-6-methoxy-2-(methylthio) pyrimidine (0.25 g, 1.17 mmol) from Step-1 and DIPEA (0.01 mL, 0.07 mmol) were added. The reaction mixture was then stirred at rt for 18 hrs. The reaction mixture was treated with NH$_4$Cl (10 mL, saturated solution in H$_2$O) and extracted with EtOAc (3×20 mL). The organic layer was collected, dried over anhydrous Na$_2$SO$_4$, filtered and evaporated to dryness under reduced pressure to give a residue, which was purified on pre-packed Silica gel using 0-70% EtOAc in Hexanes (30 min). Yield: 193 mg (43%). $^1$H NMR (CDCl$_3$) δ 5.98 (s, 1H), 4.75 (s, 2H), 4.04 (s, 3H), 2.50 (s, 3H), 2.09 (s, 3H), 2.05-1.98 (m, 6H), 1.73-1.64 (m, 6H). ESIMS: m/z 381.9 [M+H]$^+$.

iii. Step-3.

Synthesis of N-(adamantan-1-yl)-2-((5-fluoro-6-methoxy-2-(methylsulfonyl)pyrimidin-4-yl)oxy)acetamide: mCPBA (0.24 g, 1.06 mmol) was added to a solution of N-(adamantan-1-yl)-2-((5-fluoro-6-methoxy-2-(methylthio) pyrimidin-4-yl)oxy)acetamide (0.19 g, 0.51 mmol) from Step-2 in anhydrous DCM (13 mL) at 0° C. The reaction mixture was then stirred at rt for 18 hr. The reaction mixture was diluted with DCM (13 mL), washed with Na$_2$S$_2$O$_3$ (5% solution in H$_2$O, 3×13 mL) and Na$_2$CO$_3$ (5% solution in H$_2$O, 3×13 mL). The reaction mixture then washed repeatedly with H$_2$O until the aqueous washings had reached to pH~7. The undissolved solids were filtered off. The filtrate was dried over Na$_2$SO$_4$, filtered and evaporated to dryness under reduced pressure to give a residue, which was used for the next step without further purification.

iv. Step-4.

Synthesis of N-(adamantan-1-yl)-2-((5-fluoro-6-methoxy-2-oxo-1,2-dihydropyrimidin-4-yl)oxy)acetamide (46): Sodium hydroxide (2N solution in water) (0.004 mL, 0.097 mmol) was added to a solution of N-(adamantan-1-yl)-2-((5-fluoro-6-methoxy-2-(methylsulfonyl)pyrimidin-4-yl)oxy)acetamide (0.02 g, 0.05 mmol) from Step-3 in anhydrous 1,4-dioxane (1 mL). The reaction mixture was then stirred at 60° C. for 18 hr. The solvent was removed and the residue was dissolved in acetonitrile (0.5 mL), H$_2$O (0.5 ml) and HCl (1N, 0.1 mL) and stirred for 10 min. The mixture was extracted with EtOAc (3×20 mL). The organic layer was collected, dried over Na$_2$SO$_4$, filtered and evaporated to dryness under reduced pressure to give a residue, which was purified on pre-packed Silica gel column using 0-10% MeOH in DCM (20 min). Yield: 10 mg (59%). $^1$H NMR (CDCl$_3$) δ 6.13 (s, 1H), 4.76 (s, 2H), 4.03 (s, 3H), 2.09 (s, 3H), 2.04-2.01 (m, 6H), 1.70-1.66 (m, 6H). HR-ESIMS: m/z 352.16671 [M+H]$^+$ calcd. for C$_7$H$_{23}$FN$_3$O$_4$, found 352.16645. HPLC purity: 100% (Retention Time=13.8 min).

2. Characterization of Antiviral Agents

A list of compounds evaluated for antiviral activity is shown in Table 1 below.

TABLE 1

| No. | Structure | CHIKV$^a$ VTR (logs) | CHIKV$^a$ EC$_{90}$ (μM) | CHIKV$^a$ EC$_{50}$ (μM) | VEEV$^b$ VTR (logs) | VEEV$^c$ EC$_{90}$ (μM) | VEEV$^d$ EC$_{50}$ (μM) | CC$_{50}$$^e$ (μM) |
|---|---|---|---|---|---|---|---|---|
| 1 | 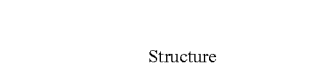 | 6.9 | 0.089 | 0.66 | ND | 1.9 | 4.33 | >127 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 2 | 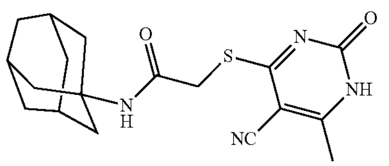 [SMILES: Cc1[nH]c(=O)nc(SCC(=O)NC23CC4CC(CC(C4)C2)C3)c1C#N] | 1.25 | ND | 22.9 | 1.1 | ND | >40 | >40 |
| 3 | 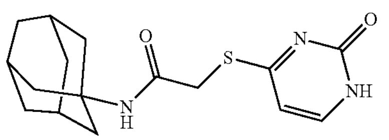 | 7.44 | 0.31 | 0.50 | 4.49 | 0.31 | 2.50 | >40 |
| 4 | 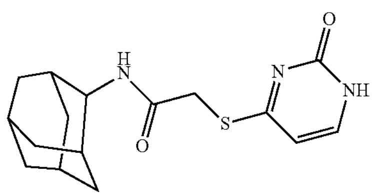 [SMILES: O=C(CSc1cc[nH]c(=O)n1)NC1C2CC3CC(C2)CC1C3] | 7.30 | 0.61 | 0.437 | 5.88 | ND | 1.68 | >40 |
| 5 | 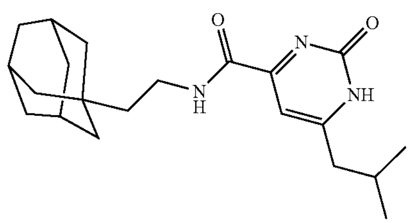 [SMILES: CC(C)Cc1cc(C(=O)NCCC23CC4CC(CC(C4)C2)C3)nc(=O)[nH]1] | ND | ND | 35.19 | ND | ND | >40 | >40 |
| 6 | 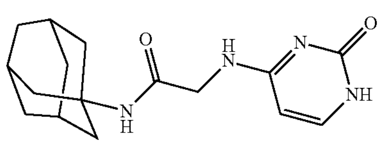 [SMILES: O=C(CNc1cc[nH]c(=O)n1)NC12CC3CC(CC(C3)C1)C2] | ND | ND | 11.8 | ND | ND | >40 | >40 |
| 7 | 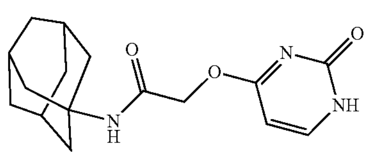 [SMILES: O=C(COc1cc[nH]c(=O)n1)NC12CC3CC(CC(C3)C1)C2] | 3.68 | 0.70 | 3.2 | 1.79 | 1.10 | 38.75 | >40 |
| 8 | 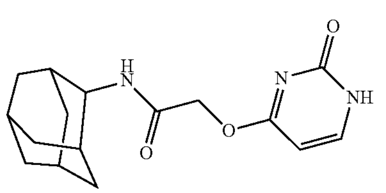 [SMILES: O=C(COc1cc[nH]c(=O)n1)NC1C2CC3CC(C2)CC1C3] | 1.05 | 0.21 | >40 | 1.94 | 0.08 | >40 | >40 |
| 9 | 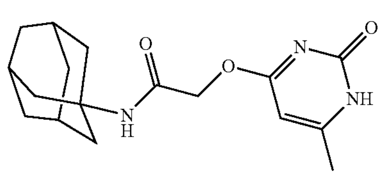 [SMILES: Cc1cc(OCC(=O)NC23CC4CC(CC(C4)C2)C3)nc(=O)[nH]1] | 1.81 | 3.50 | 1.2 | 1.37 | 1.10 | 20.01 | >40 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 10 | 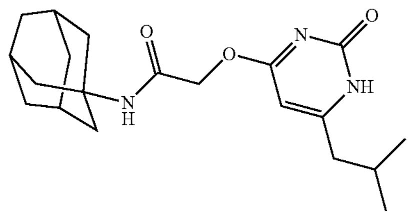 [SMILES: CC(C)Cc1cc(OCC(=O)NC23CC4CC(CC(C4)C2)C3)nc(=O)[nH]1] | 8.16 | 0.31 | 1.15 | 2.74 | 1.20 | 19.69 | >40 |
| 11 | 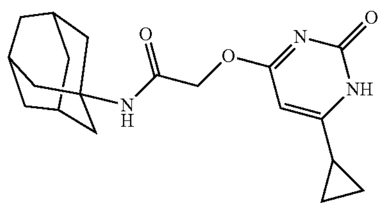 [SMILES: O=C(COc1cc(C2CC2)[nH]c(=O)n1)NC12CC3CC(CC(C3)C1)C2] | 1.05 | 0.56 | 0.24 | 2.97 | 1.10 | 20.55 | >40 |
| 12 | 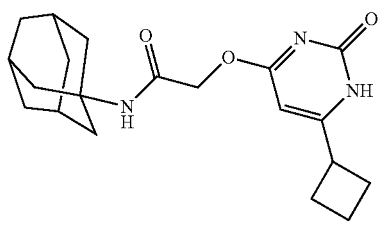 [SMILES: O=C(COc1cc(C2CCC2)[nH]c(=O)n1)NC12CC3CC(CC(C3)C1)C2] | 3.31 | 0.10 | 0.11 | 3.1 | 0.10 | 1.88 | >40 |
| 13 | 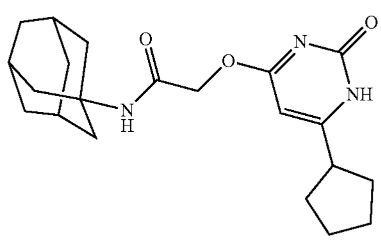 [SMILES: O=C(COc1cc(C2CCCC2)[nH]c(=O)n1)NC12CC3CC(CC(C3)C1)C2] | 5.93 | 0.04 | 1.24 | 1.94 | 4.5 | 17.45 | >40 |
| 14 | 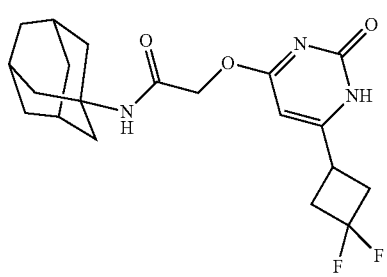 [SMILES: O=C(COc1cc(C2CC(F)(F)C2)[nH]c(=O)n1)NC12CC3CC(CC(C3)C1)C2] | 3.17 | 0.07 | <0.078 | 8.19 | 0.03 | 0.83 | >40 |
| 15 | 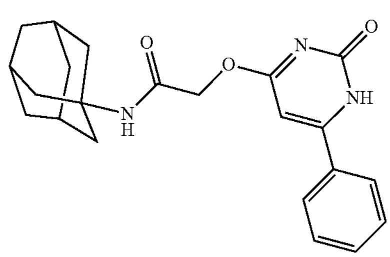 [SMILES: O=C(COc1cc(-c2ccccc2)[nH]c(=O)n1)NC12CC3CC(CC(C3)C1)C2] | 8.93 | 2.7 | 1.47 | 3.25 | 2.02 | 20.84 | >40 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 16 | 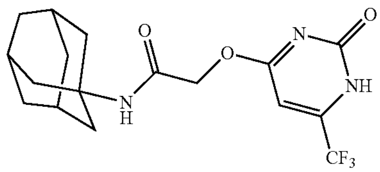 [SMILES: O=C(COc1cc(C(F)(F)F)[nH]c(=O)n1)NC12CC3CC(CC(C3)C1)C2] | 1.09 | 15 | >40 | 0 | >10 | >40 | >40 |
| 17 | 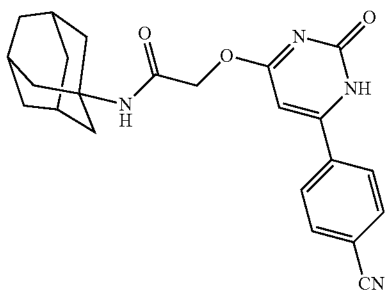 [SMILES: N#Cc1ccc(-c2cc(OCC(=O)NC34CC5CC(CC(C5)C3)C4)nc(=O)[nH]2)cc1] | 1.59 | >40 | >40 | 3.69 | 9.80 | >40 | >40 |
| 18 | 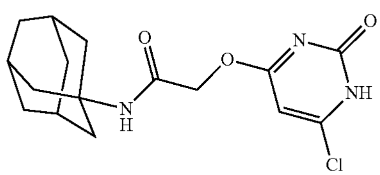 [SMILES: O=C(COc1cc(Cl)[nH]c(=O)n1)NC12CC3CC(CC(C3)C1)C2] | 5.19 | 0.51 | 0.81 | 1.0 | 5.65 | 16.14 | >40 |
| 19 | 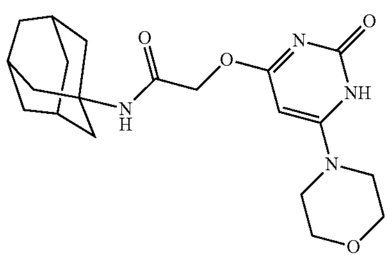 [SMILES: O=C(COc1cc(N2CCOCC2)[nH]c(=O)n1)NC12CC3CC(CC(C3)C1)C2] | 4.84 | 0.74 | 2.38 | 4.4 | 3.2 | 33.31 | >40 |
| 20 | 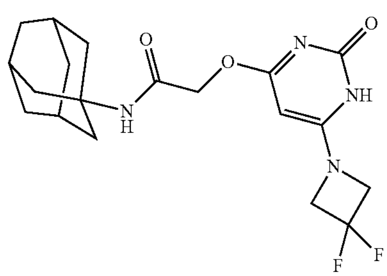 [SMILES: O=C(COc1cc(N2CC(F)(F)C2)[nH]c(=O)n1)NC12CC3CC(CC(C3)C1)C2] | 3.49 | 0.067 | <0.078 | 6.63 | 0.40 | 2.01 | >40 |
| 21 | 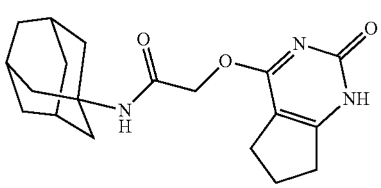 [SMILES: O=C(COc1nc(=O)[nH]c2c1CCC2)NC12CC3CC(CC(C3)C1)C2] | 4.26 | 0.30 | 0.53 | 5.20 | 1.0 | 15.73 | >40 |
| 22 | 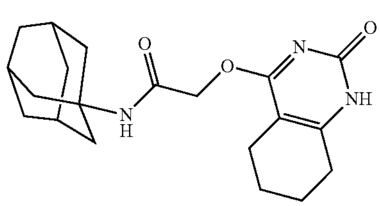 [SMILES: O=C(COc1nc(=O)[nH]c2c1CCCC2)NC12CC3CC(CC(C3)C1)C2] | 4.94 | 0.045 | 0.64 | 7.02 | 1.44 | 8.70 | >40 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 23 | 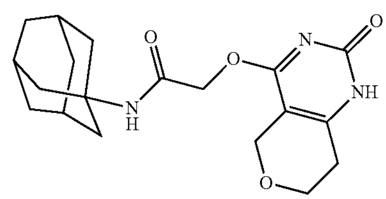 [SMILES: O=C(COc1nc(=O)[nH]c2c1COCC2)NC12CC3CC(CC(C3)C1)C2] | 5.85 | 0.20 | 1.11 | 6.4 | 2.1 | 11.07 | >40 |
| 24 | 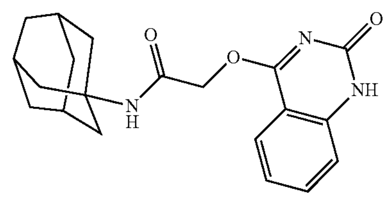 [SMILES: O=C(COc1nc(=O)[nH]c2ccccc12)NC12CC3CC(CC(C3)C1)C2] | 6.28 | 0.30 | 0.47 | 1 | 3.2 | >40 | >40 |
| 25 | 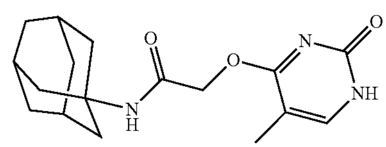 [SMILES: Cc1c[nH]c(=O)nc1OCC(=O)NC12CC3CC(CC(C3)C1)C2] | 4.91 | 2.10 | 1.97 | 3.04 | 2.83 | 16.09 | >40 |
| 26 | 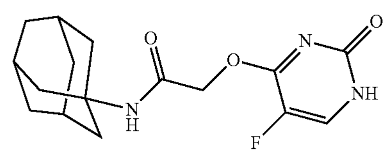 [SMILES: O=C(COc1nc(=O)[nH]cc1F)NC12CC3CC(CC(C3)C1)C2] | 5.19 | 0.30 | 3.15 | 3.22 | 0.10 | >40 | >40 |
| 27 | 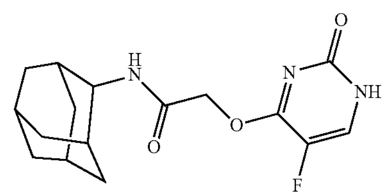 [SMILES: O=C(COc1nc(=O)[nH]cc1F)NC1C2CC3CC(C2)CC1C3] | 1.31 | 8.75 | 32.53 | 0 | 10 | >40 | >40 |
| 28 | 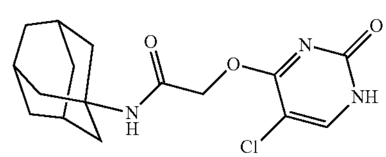 [SMILES: O=C(COc1nc(=O)[nH]cc1Cl)NC12CC3CC(CC(C3)C1)C2] | 1.6 | 10 | 33.37 | 0.71 | >10 | >40 | >40 |
| 29 | 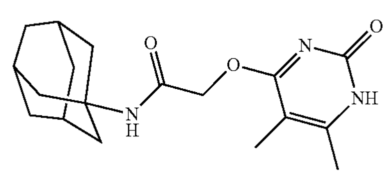 [SMILES: Cc1[nH]c(=O)nc(OCC(=O)NC23CC4CC(CC(C4)C2)C3)c1C] | 4.24 | 0.40 | 2.29 | 2.91 | 2.97 | >40 | >40 |
| 30 | 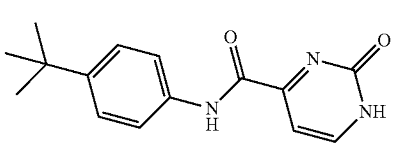 [SMILES: CC(C)(C)c1ccc(NC(=O)c2cc[nH]c(=O)n2)cc1] | ND | ND | 26.38 | ND | ND | >40 | >40 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 31 | 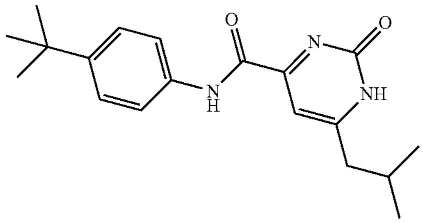 [SMILES: CC(C)Cc1cc(C(=O)Nc2ccc(C(C)(C)C)cc2)nc(=O)[nH]1] | ND | ND | 13.08 | ND | ND | >40 | >40 |
| 32 | 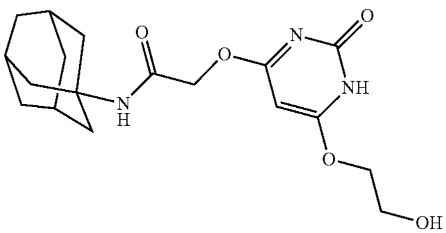 [SMILES: O=C(COc1cc(OCCO)[nH]c(=O)n1)NC12CC3CC(CC(C3)C1)C2] | 3.45 | 0.61 | 4.69 | Pend | Pend | >40 | >40 |
| 33 | 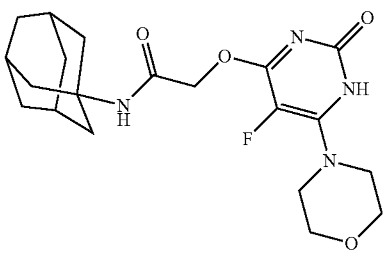 [SMILES: O=C(COc1nc(=O)[nH]c(N2CCOCC2)c1F)NC12CC3CC(CC(C3)C1)C2] | 6.08 | 0.15 | 1.80 | Pend | Pend | 23.95 | >40 |
| 34 | 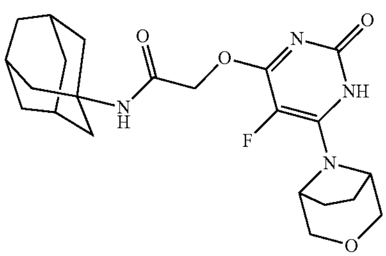 [SMILES: O=C(COc1nc(=O)[nH]c(N2C3CCC2COC3)c1F)NC12CC3CC(CC(C3)C1)C2] | 6.13 | 0.19 | 1.02 | 1.97 | 5 | 22.51 | >40 |
| 35 | 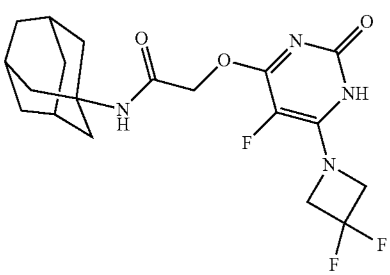 [SMILES: O=C(COc1nc(=O)[nH]c(N2CC(F)(F)C2)c1F)NC12CC3CC(CC(C3)C1)C2] | 4 | 0.051 | 0.70 | 3.35 | 1.5 | 5.19 | >40 |
| 36 | 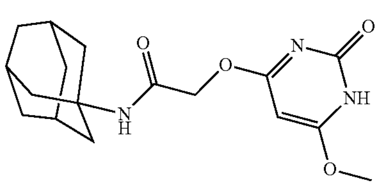 [SMILES: COc1cc(OCC(=O)NC23CC4CC(CC(C4)C2)C3)nc(=O)[nH]1] | 4.56 | 0.23 | 1.14 | 0.63 | >10 | >40 | >40 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 37 | 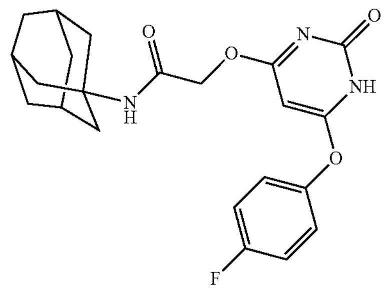 [SMILES: O=C(COc1cc(Oc2ccc(F)cc2)[nH]c(=O)n1)NC12CC3CC(CC(C3)C1)C2] | 0 | >10 | >40 | 0.8 | >10 | >40 | >40 |
| 38 | 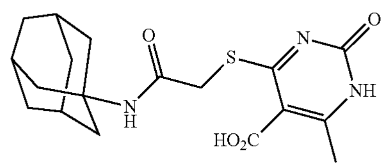 [SMILES: Cc1[nH]c(=O)nc(SCC(=O)NC23CC4CC(CC(C4)C2)C3)c1C(=O)O] | 1.19 | ND | >40 | 0.23 | ND | >40 | >40 |
| 39 | 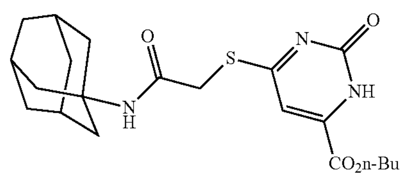 | ND | ND | >40 | ND | ND | >40 | >40 |
| 40 | 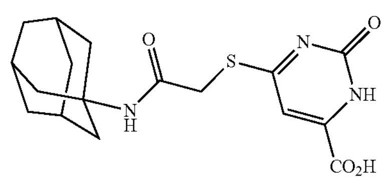 [SMILES: O=C(CSc1cc(C(=O)O)[nH]c(=O)n1)NC12CC3CC(CC(C3)C1)C2] | ND | ND | >40 | ND | ND | >40 | >40 |
| 41 | 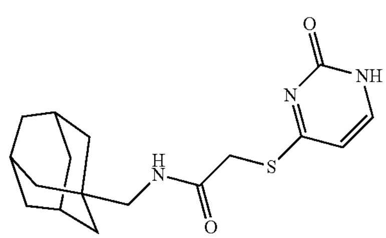 [SMILES: O=C(CSc1cc[nH]c(=O)n1)NCC12CC3CC(CC(C3)C1)C2] | ND | ND | >40 | ND | ND | >40 | >40 |
| 42 | 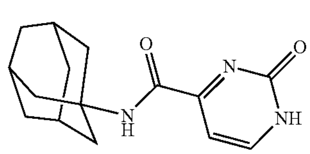 [SMILES: O=C(NC12CC3CC(CC(C3)C1)C2)c1cc[nH]c(=O)n1] | ND | ND | >40 | ND | ND | >40 | >40 |
| 43 | 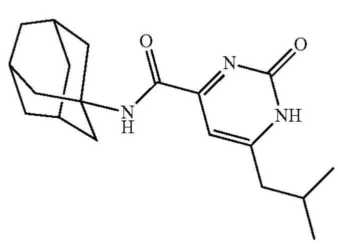 [SMILES: CC(C)Cc1cc(C(=O)NC23CC4CC(CC(C4)C2)C3)nc(=O)[nH]1] | ND | ND | >40 | ND | ND | >40 | >40 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 44 | *structure* | 0.78 | >10 | >40 | 0 | >10 | >40 | >40 |
| 45 | *structure* | 5.58 | 0.08 | 0.429 | 2.62 | 0.98 | 8.945 | >40 |
| 46 | *structure* | 0.42 | >10 | >40 | 0 | >10 | >40 | >40 |
| 47 | *structure* | 5.66 | 0.8 | 6.775 | 0.28 | >10 | >40 | >40 |
| 48 | *structure* | 5.51 | 0.06 | 0.283 | 3.28 | 0.65 | 3.769 | >40 |
| 49 | *structure* | 3.73 | 1.3 | 3.081 | 0 | >10 | 38.628 | >40 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 50 | 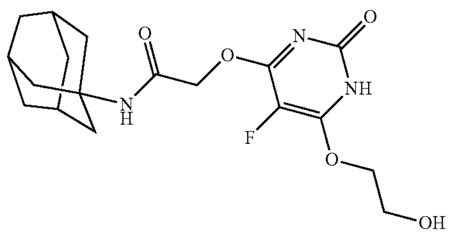 [SMILES: O=C(COc1nc(=O)[nH]c(OCCO)c1F)NC12CC3CC(CC(C3)C1)C2] | 0 | >10 | 25.378 | 0.5 | >10 | >40 | >40 |
| 51 | 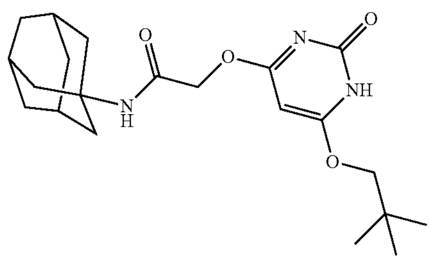 [SMILES: CC(C)(C)COc1cc(OCC(=O)NC23CC4CC(CC(C4)C2)C3)nc(=O)[nH]1] | 3.77 | 0.75 | 7.428 | 3.85 | 0.1 | >40 | >40 |
| 52 | 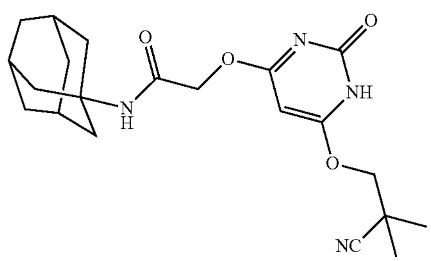 [SMILES: CC(C)(C#N)COc1cc(OCC(=O)NC23CC4CC(CC(C4)C2)C3)nc(=O)[nH]1] | 2.42 | 2.5 | 13.709 | 2.5 | 2.5 | >40 | >40 |
| 53 | 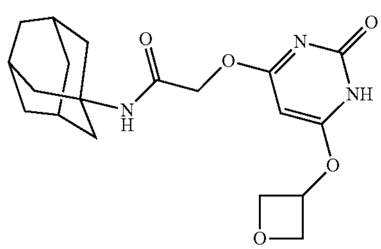 [SMILES: O=C(COc1cc(OC2COC2)[nH]c(=O)n1)NC12CC3CC(CC(C3)C1)C2] | Pend | Pend | 27.932 | Pend | Pend | >40 | >40 |
| 54 | 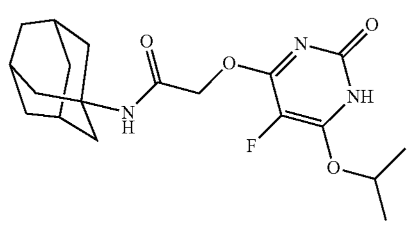 [SMILES: CC(C)Oc1[nH]c(=O)nc(OCC(=O)NC23CC4CC(CC(C4)C2)C3)c1F] | Pend | Pend | 21.543 | Pend | Pend | >40 | >40 |
| 55 | 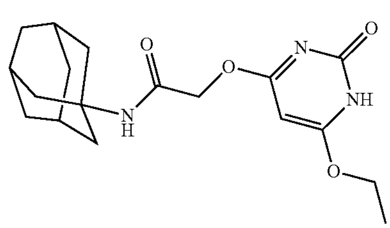 [SMILES: CCOc1cc(OCC(=O)NC23CC4CC(CC(C4)C2)C3)nc(=O)[nH]1] | 4 | 0.14 | 0.179 | 0.05 | >10 | 2.781 | >40 |

TABLE 1-continued

| No. | Structure | CHIKV[a] VTR (logs) | CHIKV[a] EC$_{90}$ (μM) | CHIKV[a] EC$_{50}$ (μM) | VEEV[b] VTR (logs) | VEEV[c] EC$_{90}$ (μM) | VEEV[d] EC$_{50}$ (μM) | CC$_{50}$[e] (μM) |
|---|---|---|---|---|---|---|---|---|
| 56 | (structure) | 6.6 | 0.17 | 0.701 | 0 | >10 | 16.203 | >40 |
| 57 | (structure) | 7.79 | 0.3 | 2.971 | Pend | Pend | >40 | >40 |

[a]VTR = CHIKV titer reduction at 10 μM; EC$_{90}$ = effective concentration of 90% inhibition of virus in a VTR assay using normal human dermal fibroblasts (NHDF) cells
[b]EC$_{50}$ = Effective concentration of 50% cells in Cytopathic Effect Assay (CPE) assay using CHIKV linked NanoLuc luciferase reporter in a telomerized human foreskin fibroblast cells that lack IRF3 (THFF-ΔIRF3).
[c]VTR = VEEV titer reduction at 10 μM; EC$_{90}$ = effective concentration of 90% inhibition of virus in a VTR assay using normal human dermal fibroblasts (NHDF) cells
[d]EC$_{50}$: = Effective concentration of 50% cells in Cytopathic Effect Assay (CPE) assay using VEEV (TC-83) in THFF-ΔIRF3 cells.
[e]CC$_{50}$ = Effective toxicity concentration of THFF-ΔIRF3 cells 50% inhibition.
Pend = pending

3. In Vivo Characterization of Antiviral Agents a. Compound No. 7 Reduces Chikungunya Virus Disease and Viremia in Mice wherein each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —OCy², —OAr¹, —O(C1-C4 alkyl)OR¹⁰, —O(C1-C4 alkyl)Ar¹, —CO₂R¹⁰, and Cy²;

wherein each occurrence of $R^{10}$, when present, is independently selected from hydrogen and C1-C4 alkyl;

wherein each occurrence of $Ar^1$, when present, is independently selected from C2-C5 heteroaryl and C6-C12 aryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl;

or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein $Cy^1$ is selected from C2-C9 heteroaryl, C6 aryl, and adamantyl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl;

provided that when $Cy^1$ is C2-C9 heteroaryl, then either (i) p is 1 and A is O or (ii) n is 1 or 2 and each of $R^{3a}$ and $R^{3b}$ are not hydrogen;

provided that when $Cy^1$ is C6 aryl, then p is 1 and either (i) A is O or (ii) each of $R^{2a}$ and $R^{2b}$ is hydrogen and at least one of $R^{3a}$ and $R^{3b}$ is not hydrogen; and provided that when $Cy^1$ is

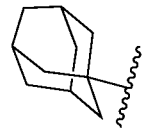 [SMILES: *C12CC3CC(CC(C3)C1)C2]

and p is 0, then n is 0 or 2, or a pharmaceutically acceptable salt thereof.

2. The compound of claim 1, wherein n is 0.

3. The compound of claim 1, wherein p is 1.

4. The compound of claim 1, wherein A is O.

5. The compound of claim 1, wherein each of $R^{2a}$ and $R^{2b}$ is independently selected from hydrogen, halogen, C1-C6 alkyl, C1-C4 haloalkyl, C1-C4 alkoxy, —OAr¹, —O(C1-C4 alkyl)OR¹⁰, —O(C1-C4 alkyl)Ar¹, —CO₂R¹⁰, and Cy².

6. The compound of claim 1, wherein each of $R^{2a}$ and $R^{2b}$ is hydrogen.

7. The compound of claim 1, wherein $Cy^1$ is adamantyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl.

8. The compound of claim 1, wherein $Cy^1$ is unsubstituted adamantyl.

9. The compound of claim 1, wherein $Cy^1$ is a structure:

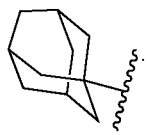 [SMILES: *C12CC3CC(CC(C3)C1)C2]

10. The compound of claim 1, wherein the compound has a structure represented by a formula:

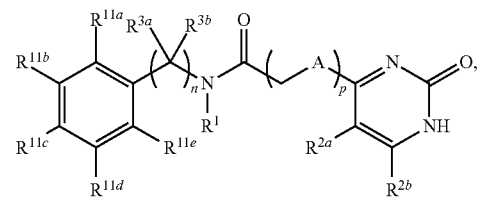

wherein each of $R^{11a}$, $R^{11b}$, $R^{11c}$, $R^{11d}$, and $R^{11e}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl, provided that at least two of $R^{11a}$, $R^{11b}$, $R^{11c}$, $R^{11d}$, and $R^{11e}$ are hydrogen.

11. The compound of claim 10, wherein the compound has a structure represented by a formula:

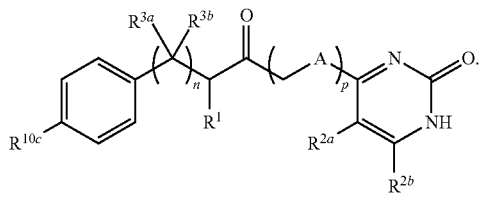

12. The compound of claim 1, wherein the compound has a structure represented by a formula selected from:

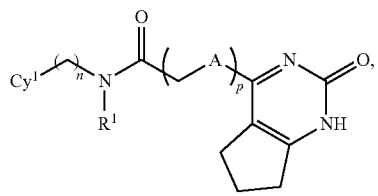

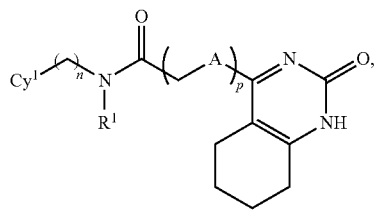

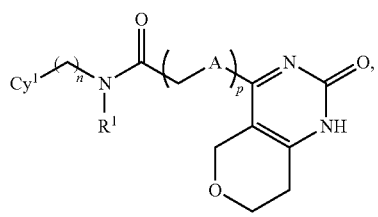

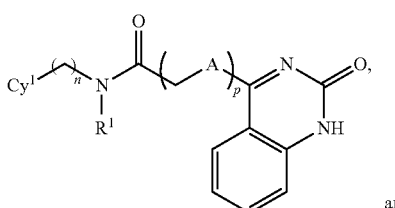

and

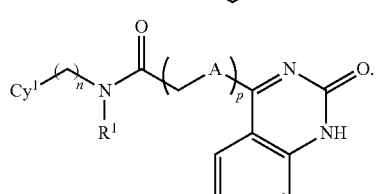

13. The compound of claim 1, wherein the compound has a structure represented by a formula:

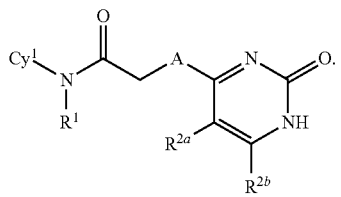

14. The compound of claim 1, wherein the compound has a structure represented by a formula:

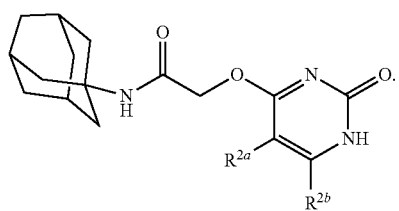

15. The compound of claim 1, wherein the compound is selected from:

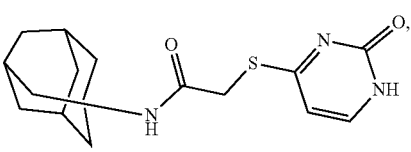

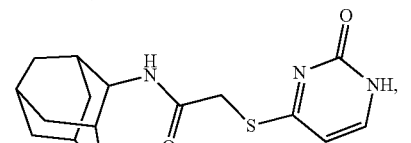

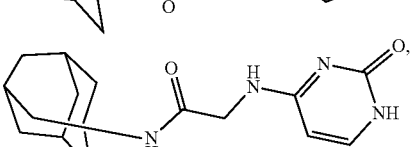

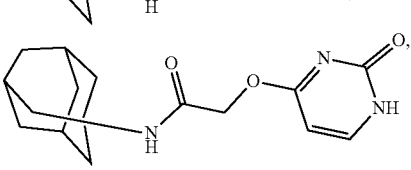

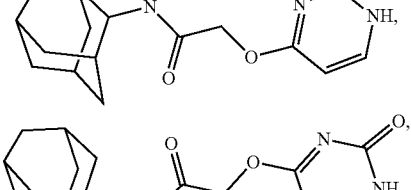

169
-continued
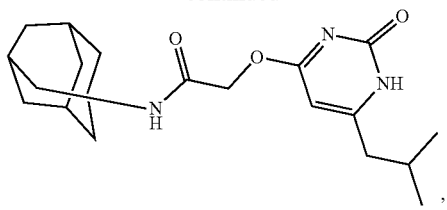
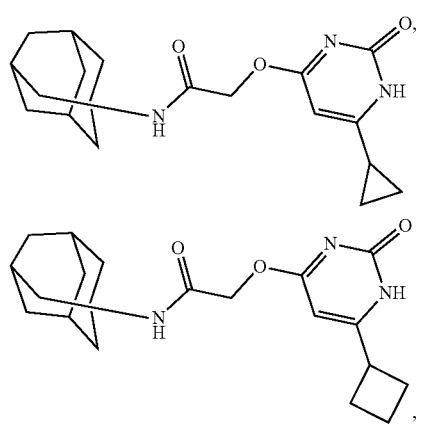
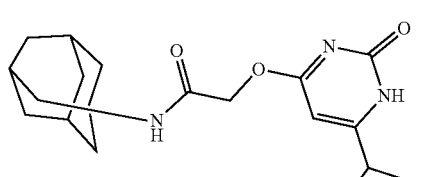
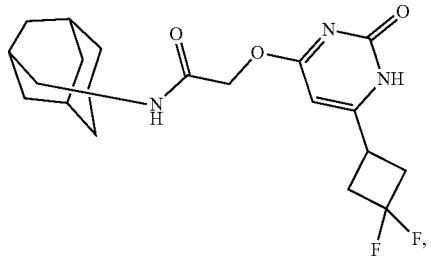
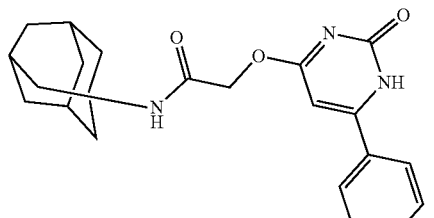
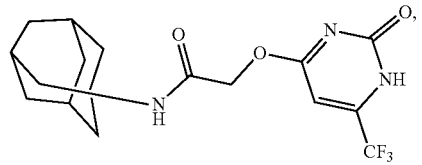
170
-continued
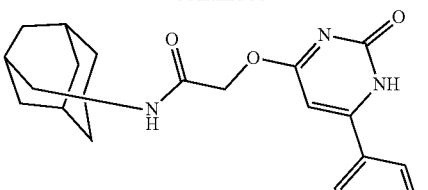
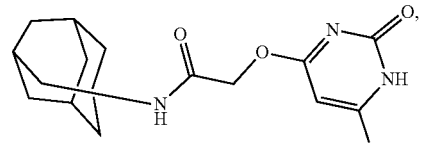
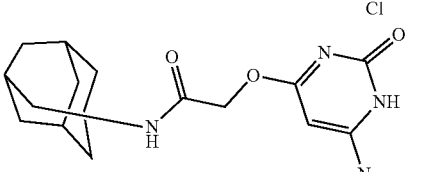
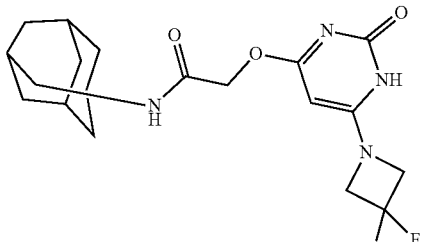
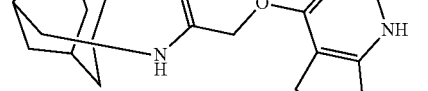
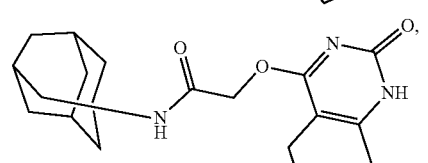
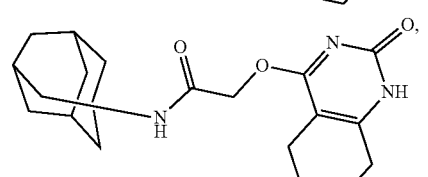
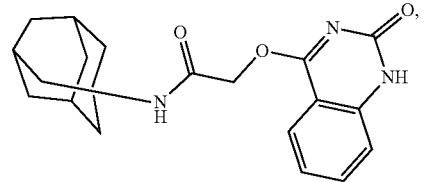

-continued
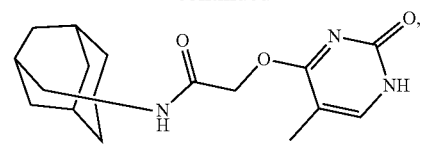
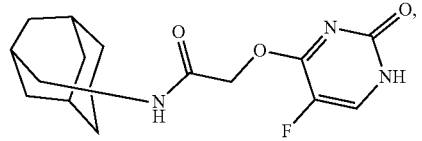
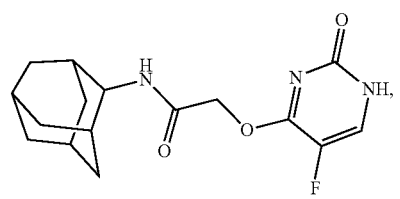
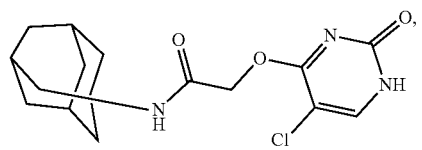
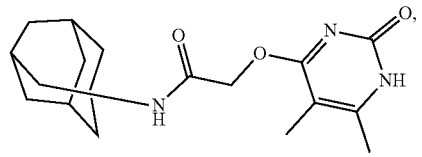
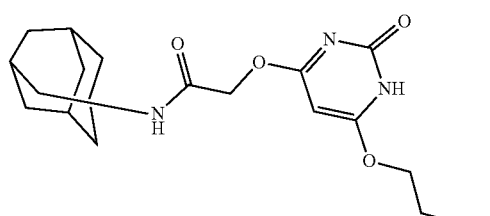
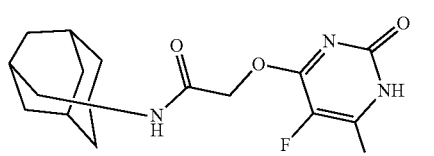
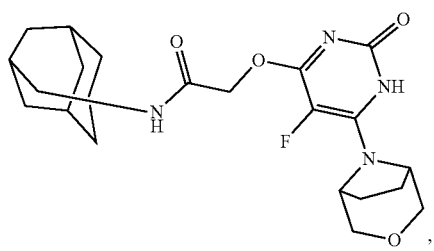
-continued
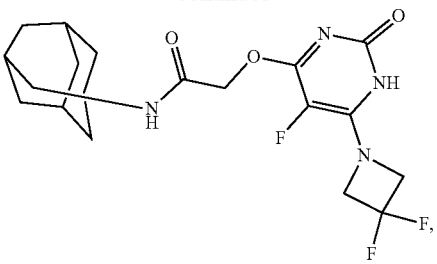
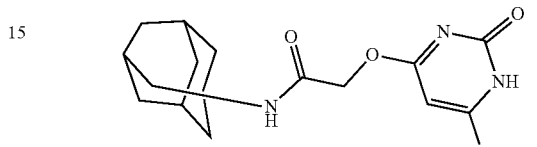
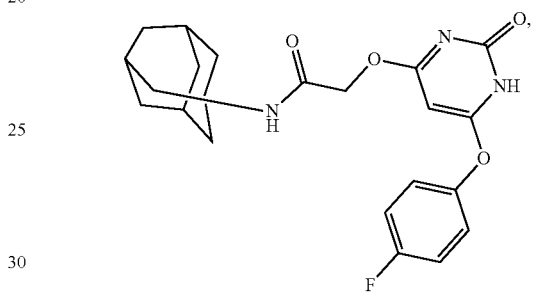
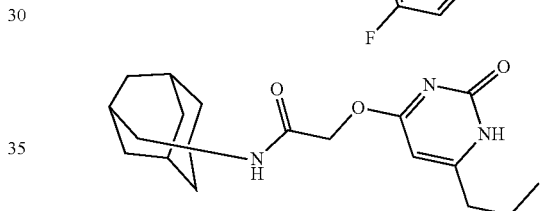
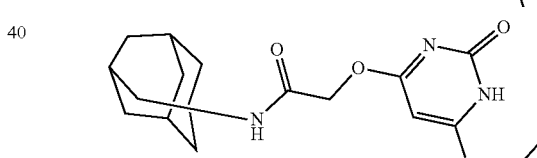
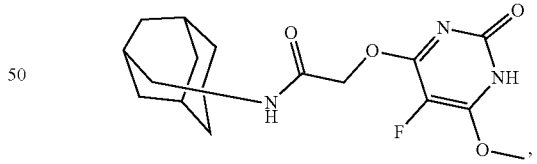
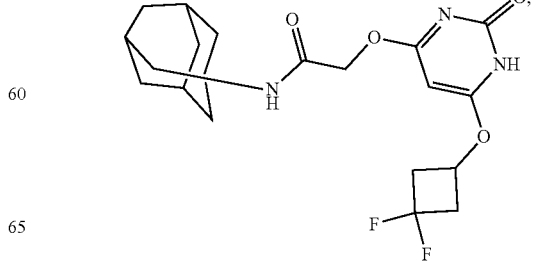

-continued

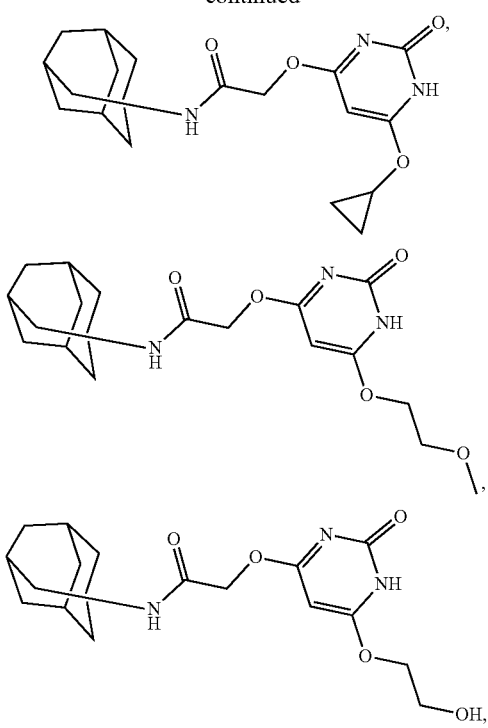

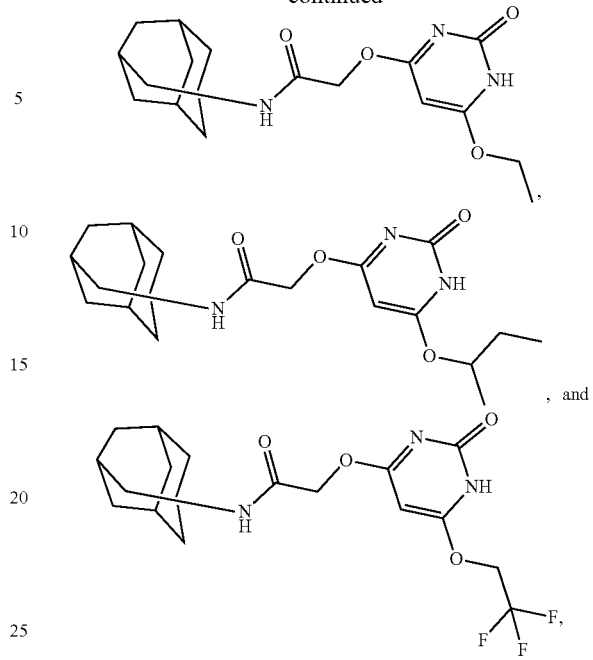

16. The compound of claim 1, wherein the compound is:

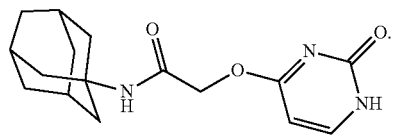 [SMILES: O=C(COc1cc[nH]c(=O)n1)NC12CC3CC(CC(C3)C1)C2]

17. A pharmaceutical composition comprising a therapeutically effective amount of the compound of claim 1, and a pharmaceutically acceptable carrier.

18. A method for treating a viral infection in a subject, the method comprising administering to the subject an effective amount of a compound having a structure represented by a formula:

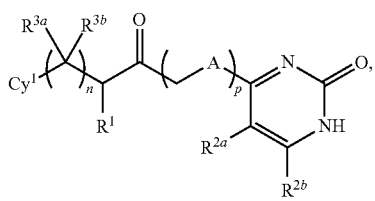

wherein n is 0, 1, or 2;
wherein p is 0 or 1;
wherein A is O, S, or NH;
wherein $R^1$ is selected from hydrogen and C1-C4 alkyl;
wherein each of $R^{2a}$ and $R^{2b}$ is independently selected from hydrogen, halogen, C1-C6 alkyl, C1-C4 haloalkyl, C1-C8 alkoxy, C1-C8 haloalkoxy, C1-C8 cyanoalkoxy, —OCy², —OAr¹, —O(C1-C4 alkyl)OR¹⁰, —O(C1-C4 alkyl)Ar¹, —CO₂R¹⁰, and Cy²;
wherein each occurrence of $R^{10}$, when present, is independently selected from hydrogen and C1-C4 alkyl;

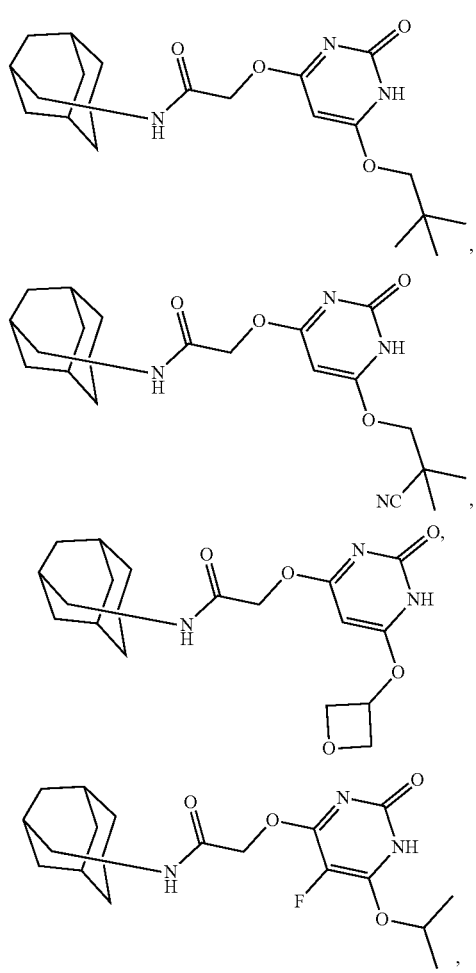

wherein each occurrence of $Ar^1$, when present, is independently selected from C2-C5 heteroaryl and C6-C12 aryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each occurrence of $Cy^2$, when present, is independently selected from C3-C6 cycloalkyl, C3-C6 heterocycloalkyl, and phenyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

or wherein $R^{2a}$ and $R^{2b}$ are covalently bonded and, together with the intermediate atoms, comprise a C5-C6 cycloalkyl, a C2-C5 heterocycloalkyl, a C6 aryl or a C2-C5 heteroaryl, and are substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$ and $R^{3b}$, when present, is independently selected from hydrogen, halogen, C1-C4 alkyl, and C1-C4 haloalkyl;

or wherein $R^{3a}$ and $R^{3b}$, when present, are covalently bonded and, together with the intermediate atoms, comprise a C3-C4 cycloalkyl substituted with 0, 1, 2, or 3 groups independently selected from selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein $Cy^1$ is selected from C2-C9 heteroaryl, C6 aryl, and adamantyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, and C3-C6 cycloalkyl;

provided that when p is 1, A is S, and $Cy^1$ is C6 aryl, then $Cy^1$ is not substituted with a halogen group, or a pharmaceutically acceptable salt thereof, wherein the viral infection is due to an Alphavirus, thereby treating the viral infection.

19. The method of claim 18, wherein the Alphavirus is selected from Chikungunya virus (CHIKV), Ross River virus, Venezuelan equine encephalitis (VEEV), Eastern equine encephalitis (EEEV), and Western equine encephalitis (WEEV).

20. The method of claim 18, wherein the Alphavirus is selected from CHIKV, WEEV, EEEV, and VEEV.

* * * * *